(12) United States Patent
McGowan et al.

(10) Patent No.: US 10,221,178 B2
(45) Date of Patent: Mar. 5, 2019

(54) PURINE INHIBITORS OF HUMAN PHOSPHATIDYLINOSITOL 3-KINASE DELTA

(71) Applicant: MERCK SHARP & DOHME CORP., Rahway, NJ (US)

(72) Inventors: Meredeth Ann McGowan, Boston, MA (US); Hua Zhou, Acton, MA (US); Jason D. Katz, Newton Highlands, MA (US); Lihu Yang, Edison, NJ (US); Joey L. Methot, Westwood, MA (US); Kathryn Ann Lipford, Boston, MA (US); Shimin Xu, Beijing (CN); Ning Fu, Beijing (CN); Guoquan Xu, Beijing (CN); Deqian Bian, Beijing (CN); Jianmin Fu, Beijing (CN); Yabin Li, Beijing (CN); Kin Chiu Fong, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/736,510

(22) PCT Filed: Jun. 24, 2016

(86) PCT No.: PCT/US2016/039147
§ 371 (c)(1),
(2) Date: Dec. 14, 2017

(87) PCT Pub. No.: WO2017/003836
PCT Pub. Date: Jan. 5, 2017

(65) Prior Publication Data
US 2018/0141947 A1 May 24, 2018

(30) Foreign Application Priority Data
Jun. 29, 2015 (CN) ................ PCT/CN2015/082673

(51) Int. Cl.
| | | |
|---|---|---|
| *C07D 473/30* | (2006.01) |
| *C07D 473/34* | (2006.01) |
| *C07D 471/04* | (2006.01) |
| *C07D 519/00* | (2006.01) |
| *A61K 45/06* | (2006.01) |
| *A61P 37/00* | (2006.01) |
| *A61P 17/06* | (2006.01) |
| *A61P 11/06* | (2006.01) |
| *A61P 11/08* | (2006.01) |
| *A61P 11/00* | (2006.01) |
| *A61P 35/00* | (2006.01) |

(52) U.S. Cl.
CPC ............ *C07D 473/30* (2013.01); *A61K 45/06* (2013.01); *A61P 11/06* (2018.01); *A61P 11/08* (2018.01); *A61P 17/06* (2018.01); *A61P 35/00* (2018.01); *A61P 37/00* (2018.01); *C07D 471/04* (2013.01); *C07D 473/34* (2013.01); *C07D 519/00* (2013.01)

(58) Field of Classification Search
CPC .......... A61K 45/06; A61P 11/00; A61P 11/06; A61P 11/08; A61P 17/06; A61P 19/02; A61P 35/00; A61P 37/00; C07D 471/04; C07D 473/30; C07D 473/34; C07D 519/00
See application file for complete search history.

(56) References Cited

U.S. PATENT DOCUMENTS

| | | |
|---|---|---|
| 7,776,859 B2 | 8/2010 | Balog et al. |
| 2013/0109665 A1 | 5/2013 | Bissantz et al. |
| 2015/0005286 A1 | 1/2015 | Smith et al. |

FOREIGN PATENT DOCUMENTS

| | | | |
|---|---|---|---|
| CN | 102838600 A | 11/2012 | |
| CN | 102838600 A | 12/2012 | |
| WO | 200204474 | 1/2002 | |
| WO | 2010123931 | 10/2010 | |
| WO | 2010132757 A2 | 11/2010 | |
| WO | 2011075630 A1 | 6/2011 | |
| WO | 2011075643 A1 | 6/2011 | |
| WO | 2012037226 A1 | 3/2012 | |
| WO | 2014075393 | 5/2014 | |
| WO | WO 2014/075393 | * 5/2014 | ........... C07D 473/34 |

OTHER PUBLICATIONS

ASC RN 1206081-50-6 Registry on STN 11, Feb. 2010.
International Search Report and Written Opinion for PCT/CN2015/082673, dated Mar. 25, 2016, 17 pages.
International Search Report and Written Opinion for PCT/US2016/039147, dated Sep. 1, 2016, 10 pages.

* cited by examiner

*Primary Examiner* — Erich A Leeser
(74) *Attorney, Agent, or Firm* — Patricia A. Shatynski; John C. Todaro

(57) ABSTRACT

The instant invention provides compounds of formula I which are PI3K-delta inhibitors, and as such are useful for the treatment of PI3K-delta-mediated diseases such as inflammation, asthma, COPD and cancer.

15 Claims, No Drawings

PURINE INHIBITORS OF HUMAN PHOSPHATIDYLINOSITOL 3-KINASE DELTA

CROSS REFERENCE TO RELATED APPLICATIONS

This application is a U.S. National Phase application under 35 U.S.C. § 371 of PCT Application No. PCT/US2016/039147, filed Jun. 24, 2016 which claims priority from international application no., PCT/CN2015/082673, filed Jun. 29, 2015.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinositide 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

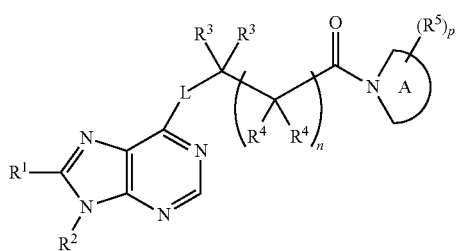

L is O or NH;
$R^1$ is $C_{1-6}$alkyl, $C_{1-6}$haloalkyl, or a 5- to 6-membered heteroaryl ring, wherein the 5- to 6-membered heteroaryl ring is substituted by 0, 1, 2, or 3 groups independently selected from fluoro, chloro, $C_{1-6}$alkyl, and $C_{1-6}$haloalkyl;
$R^2$ is hydrogen or $C_{1-6}$alkyl;
$R^3$ is each independently selected from hydrogen, $C_{1-10}$alkyl, aryl$C_{0-10}$ alkyl, $C_{3-8}$ cycloalkyl$C_{0-10}$ alkyl, —($C_{1-10}$ alkyl)OH, $C_{1-10}$ alkoxy$C_{0-10}$ alkyl, and ($C_{0-10}$ alkyl)$_{1-2}$ amino$C_{0-10}$ alkyl, and $C_{0-10}$ alkylcarbonylamino$C_{0-10}$ alkyl, wherein two $R^3$ may join together with the carbon to which they are attached to form a 3- to 8-membered ring;
$R^4$ is each independently selected from hydrogen and $C_{1-10}$alkyl, wherein two $R^4$ may join together with the carbon to which they are attached to form a 3- to 8-membered ring;
n is 0, 1, 2, 3, or 4;
p is 0, 1, 2, 3, or 4;
$R^5$ is each independently selected from hydrogen, halogen, $C_{1-10}$alkyl, oxo, cyano, $C_{1-10}$ alkoxy$C_{0-10}$ alkyl(oxy)$_{0-1}$, $C_{1-6}$alkylcarbonyl, $C_{1-6}$haloalkyl, cycloalkyl$C_{0-10}$ alkyl, and —($C_{1-10}$ alkyl)OH;
wherein the group

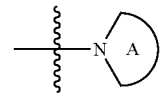

is selected from
1) $C_{3-12}$heterocycloalkyl having at least one nitrogen, wherein the $C_{3-12}$heterocycloalkyl is bonded to the illustrated carbonyl via a nitrogen atom; and
2) spiroheterocyclic ring having at least one nitrogen, wherein the spiroheterocyclic ring is bonded to the illustrated carbonyl via a nitrogen atom.

Representative compounds of the instant invention include, but are not limited to, the following compounds and their pharmaceutically acceptable salts and their stereoisomers thereof:

8-(1-ethyl-5-methyl-1H-pyrazol-4-yl)-9-methyl-6-[1-(morpholin-4-ylcarbonyl)propoxy]-9H-purine;
R-8-(1-ethyl-5-methyl-1H-pyrazol-4-yl)-9-methyl-6-[1-(morpholin-4-ylcarbonyl)propoxy]-9H-purine;
S-8-(1-ethyl-5-methyl-1H-pyrazol-4-yl)-9-methyl-6-[1-(morpholin-4-ylcarbonyl)propoxy]-9H-purine;
8-(1-ethyl-5-methyl-1H-pyrazol-4-yl)-9-methyl-6-[1-(piperidin-1-ylcarbonyl)propoxy]-9H-purine;
R-8-(1-ethyl-5-methyl-1H-pyrazol-4-yl)-9-methyl-6-[1-(piperidin-1-ylcarbonyl)propoxy]-9H-purine;
S-8-(1-ethyl-5-methyl-1H-pyrazol-4-yl)-9-methyl-6-[1-(piperidin-1-ylcarbonyl)propoxy]-9H-purine;
N-[1-(azetidin-1-ylcarbonyl)propyl]-8-(l-ethyl-5-methyl-1H-pyrazol-4-yl)-9-methyl-9H-purin-6-amine;
R—N-[1-(azetidin-1-ylcarbonyl)propyl]-8-(1-ethyl-5-methyl-1H-pyrazol-4-yl)-9-methyl-9H-purin-6-amine;
S—N-[1-(azetidin-1-ylcarbonyl)propyl]-8-(1-ethyl-5-methyl-1H-pyrazol-4-yl)-9-methyl-9H-purin-6-amine;
N-(1-{[2,6-dimethylmorpholin-4-yl]carbonyl}propyl)-8-(1-ethyl-5-methyl-1H-pyrazol-4-yl)-9-methyl-9H-purin-6-amine;
R—N-(1-{[(cis)-2,6-dimethylmorpholin-4-yl]carbonyl}propyl)-8-(1-ethyl-5-methyl-1H-pyrazol-4-yl)-9-methyl-9H-purin-6-amine;
S—N-(1-{[(cis)-2,6-dimethylmorpholin-4-yl]carbonyl}propyl)-8-(1-ethyl-5-methyl-1H-pyrazol-4-yl)-9-methyl-9H-purin-6-amine;
N-{1-[(4,4-difluoropiperidin-1-yl)carbonyl]propyl}-8-(1-ethyl-5-methyl-1H-pyrazol-4-yl)-9-methyl-9H-purin-6-amine;
R—N-{1-[(4,4-difluoropiperidin-1-yl)carbonyl]propyl}-8-(1-ethyl-5-methyl-1H-pyrazol-4-yl)-9-methyl-9H-purin-6-amine;

S—N-{1-[(4,4-difluoropiperidin-1-yl)carbonyl]propyl}-8-(1-ethyl-5-methyl-1H-pyrazol-4-yl)-9-methyl-9H-purin-6-amine;
8-(1-ethyl-5-methyl-1H-pyrazol-4-yl)-9-methyl-N-[1-(morpholin-4-ylcarbonyl)propyl]-9H-purin-6-amine;
R-8-(1-ethyl-5-methyl-1H-pyrazol-4-yl)-9-methyl-N-[1-(morpholin-4-ylcarbonyl)propyl]-9H-purin-6-amine;
S-8-(1-ethyl-5-methyl-1H-pyrazol-4-yl)-9-methyl-N-[1-(morpholin-4-ylcarbonyl)propyl]-9H-purin-6-amine;
8-(1-ethyl-5-methyl-1H-pyrazol-4-yl)-9-methyl-N-(1-methyl-2-morpholin-4-yl-2-oxoethyl)-9H-purin-6-amine;
R-8-(1-ethyl-5-methyl-1H-pyrazol-4-yl)-9-methyl-N-(1-methyl-2-morpholin-4-yl-2-oxoethyl)-9H-purin-6-amine;
S-8-(1-ethyl-5-methyl-1H-pyrazol-4-yl)-9-methyl-N-(1-methyl-2-morpholin-4-yl-2-oxoethyl)-9H-purin-6-amine;
9-ethyl-8-(2-methylpyrimidin-5-yl)-N-[1-(morpholin-4-ylcarbonyl)propyl]-9H-purin-6-amine;
R-9-ethyl-8-(2-methylpyrimidin-5-yl)-N-[1-(morpholin-4-ylcarbonyl)propyl]-9H-purin-6-amine;
S-9-ethyl-8-(2-methylpyrimidin-5-yl)-N-[1-(morpholin-4-ylcarbonyl)propyl]-9H-purin-6-amine;
N-[1-benzyl-2-morpholin-4-yl-2-oxoethyl]-8-(1-ethyl-5-methyl-1H-pyrazol-4-yl)-9-methyl-9H-purin-6-amine;
N-[(1R)-1-benzyl-2-morpholin-4-yl-2-oxoethyl]-8-(1-ethyl-5-methyl-1H-pyrazol-4-yl)-9-methyl-9H-purin-6-amine;
N-[(1S)-1-benzyl-2-morpholin-4-yl-2-oxoethyl]-8-(1-ethyl-5-methyl-1H-pyrazol-4-yl)-9-methyl-9H-purin-6-amine;
N-{1-[(4,4-difluoropiperidin-1-yl)carbonyl]cyclopropyl}-9-ethyl-8-(2-methylpyrimidin-5-yl)-9H-purin-6-amine;
8-(difluoromethyl)-N-[1-{[2,6-dimethylmorpholin-4-yl]carbonyl}propyl]-9-ethyl-9H-purin-6-amine;
8-(difluoromethyl)-N-[(1S)-1-{[(cis)-2,6-dimethylmorpholin-4-yl]carbonyl}propyl]-9-ethyl-9H-purin-6-amine;
8-(difluoromethyl)-N-[(1R)-1-{[(cis)-2,6-dimethylmorpholin-4-yl]carbonyl}propyl]-9-ethyl-9H-purin-6-amine;
8-(difluoromethyl)-N-{2-[2,6-dimethylmorpholin-4-yl]-1-methyl-2-oxoethyl}-9-ethyl-9H-purin-6-amine;
8-(difluoromethyl)-N-{(1S)-2-[(cis)-2,6-dimethylmorpholin-4-yl]-1-methyl-2-oxoethyl}-9-ethyl-9H-purin-6-amine;
8-(difluoromethyl)-N-{(1R)-2-[(cis)-2,6-dimethylmorpholin-4-yl]-1-methyl-2-oxoethyl}-9-ethyl-9H-purin-6-amine;
N-[1-{[2,6-dimethylmorpholin-4-yl]carbonyl}propyl]-9-ethyl-8-(2-methylpyrimidin-5-yl)-9H-purin-6-amine;
N-[(1S)-1-{[(cis)-2,6-dimethylmorpholin-4-yl]carbonyl}propyl]-9-ethyl-8-(2-methylpyrimidin-5-yl)-9H-purin-6-amine;
N-[(1R)-1-{[(cis)-2,6-dimethylmorpholin-4-yl]carbonyl}propyl]-9-ethyl-8-(2-methylpyrimidin-5-yl)-9H-purin-6-amine;
N-[1-{[2,6-dimethylmorpholin-4-yl]carbonyl}propyl]-9-ethyl-8-[6-(trifluoromethyl)pyridin-3-yl]-9H-purin-6-amine;
N-[(1S)-1-{[(cis)-2,6-dimethylmorpholin-4-yl]carbonyl}propyl]-9-ethyl-8-[6-(trifluoromethyl)pyridin-3-yl]-9H-purin-6-amine;
N-[(1R)-1-{[(cis)-2,6-dimethylmorpholin-4-yl]carbonyl}propyl]-9-ethyl-8-[6-(trifluoromethyl)pyridin-3-yl]-9H-purin-6-amine;
N-{1-[(1,1-dioxidothiomorpholin-4-yl)carbonyl]propyl}-9-ethyl-8-(2-methylpyrimidin-5-yl)-9H-purin-6-amine;
N-{(1S)-1-[(1,1-dioxidothiomorpholin-4-yl)carbonyl]propyl}-9-ethyl-8-(2-methylpyrimidin-5-yl)-9H-purin-6-amine;
N-{(1R)-1-[(1,1-dioxidothiomorpholin-4-yl)carbonyl]propyl}-9-ethyl-8-(2-methylpyrimidin-5-yl)-9H-purin-6-amine;
9-ethyl-N-{1-[(4-methoxyazepan-1-yl)carbonyl]propyl}-8-(2-methylpyrimidin-5-yl)-9H-purin-6-amine;
9-ethyl-N-{(1S)-1-[(4-methoxyazepan-1-yl)carbonyl]propyl}-8-((R)-2-methylpyrimidin-5-yl)-9H-purin-6-amine;
9-ethyl-N-{(1S)-1-[(4-methoxyazepan-1-yl)carbonyl]propyl}-8-((S)-2-methylpyrimidin-5-yl)-9H-purin-6-amine;
9-ethyl-N-{(1R)-1-[(4-methoxyazepan-1-yl)carbonyl]propyl}-8-((R)-2-methylpyrimidin-5-yl)-9H-purin-6-amine;
9-ethyl-N-{(1R)-1-[(4-methoxyazepan-1-yl)carbonyl]propyl}-8-((S)-2-methylpyrimidin-5-yl)-9H-purin-6-amine;
9-ethyl-N-[1-{[4-(2-methoxyethoxy)piperidin-1-yl]carbonyl}propyl]-8-(2-methylpyrimidin-5-yl)-9H-purin-6-amine;
9-ethyl-N-[(1S)-1-{[4-(2-methoxyethoxy)piperidin-1-yl]carbonyl}propyl]-8-(2-methylpyrimidin-5-yl)-9H-purin-6-amine;
9-ethyl-N-[(1R)-1-{[4-(2-methoxyethoxy)piperidin-1-yl]carbonyl}propyl]-8-(2-methylpyrimidin-5-yl)-9H-purin-6-amine;
N-[1-{[3-(difluoromethyl)azetidin-1-yl]carbonyl}propyl]-9-ethyl-8-(2-methylpyrimidin-5-yl)-9H-purin-6-amine;
N-[(1S)-1-{[3-(difluoromethyl)azetidin-1-yl]carbonyl}propyl]-9-ethyl-8-(2-methylpyrimidin-5-yl)-9H-purin-6-amine;
N-[(1R)-1-{[3-(difluoromethyl)azetidin-1-yl]carbonyl}propyl]-9-ethyl-8-(2-methylpyrimidin-5-yl)-9H-purin-6-amine;
N-{1-[(3,3-difluoropiperidin-1-yl)carbonyl]propyl}-9-ethyl-8-(2-methylpyrimidin-5-yl)-9H-purin-6-amine;
N-{(1S)-1-[(3,3-difluoropiperidin-1-yl)carbonyl]propyl}-9-ethyl-8-(2-methylpyrimidin-5-yl)-9H-purin-6-amine;
N-{(1R)-1-[(3,3-difluoropiperidin-1-yl)carbonyl]propyl}-9-ethyl-8-(2-methylpyrimidin-5-yl)-9H-purin-6-amine;
1-[2-{9-ethyl-8-(2-methylpyrimidin-5-yl)-9H-purin-6-yl]amino}butanoyl]piperidine-4-carbonitrile;
1-[(2S)-2-{[9-ethyl-8-(2-methylpyrimidin-5-yl)-9H-purin-6-yl]amino}butanoyl]piperidine-4-carbonitrile;
1-[(2R)-2-{[9-ethyl-8-(2-methylpyrimidin-5-yl)-9H-purin-6-yl]amino}butanoyl]piperidine-4-carbonitrile;
N-{1-[(1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aR,6aR-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aR,6aS-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aS,6aR-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aS,6aS-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1R)-1-[((3aS,6aR)-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1R)-1-[((3aR,6aS)-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1R)-1-[((3aS,6aS)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

N-{(1R)-1-[((3aR,6aR)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

9-ethyl-N-[1-{[3-fluoropyrrolidin-1-yl]carbonyl}propyl]-8-(2-methylpyrimidin-5-yl)-9H-purin-6-amine;

9-ethyl-N-[(1S)-1-{[(3S)-3-fluoropyrrolidin-1-yl]carbonyl}propyl]-8-(2-methylpyrimidin-5-yl)-9H-purin-6-amine;

9-ethyl-N-[(1S)-1-{[(3R)-3-fluoropyrrolidin-1-yl]carbonyl}propyl]-8-(2-methylpyrimidin-5-yl)-9H-purin-6-amine;

9-ethyl-N-[(1R)-1-{[(3S)-3-fluoropyrrolidin-1-yl]carbonyl}propyl]-8-(2-methylpyrimidin-5-yl)-9H-purin-6-amine;

9-ethyl-N-[(1R)-1-{[(3R)-3-fluoropyrrolidin-1-yl]carbonyl}propyl]-8-(2-methylpyrimidin-5-yl)-9H-purin-6-amine;

9-ethyl-N-{1-[(3-methoxyazetidin-1-yl)carbonyl]propyl}-8-(2-methylpyrimidin-5-yl)-9H-purin-6-amine;

9-ethyl-N-{(1S)-1-[(3-methoxyazetidin-1-yl)carbonyl]propyl}-8-(2-methylpyrimidin-5-yl)-9H-purin-6-amine;

9-ethyl-N-{(1R)-1-[(3-methoxyazetidin-1-yl)carbonyl]propyl}-8-(2-methylpyrimidin-5-yl)-9H-purin-6-amine;

9-ethyl-8-(2-methylpyrimidin-5-yl)-N-{1-[(3-methylpyrrolidin-1-yl)carbonyl]propyl}-9H-purin-6-amine;

9-ethyl-8-(2-methylpyrimidin-5-yl)-N-{(1S)-1-[(S-3-methylpyrrolidin-1-yl)carbonyl]propyl}-9H-purin-6-amine;

9-ethyl-8-(2-methylpyrimidin-5-yl)-N-{(1S)-1-[(R-3-methylpyrrolidin-1-yl)carbonyl]propyl}-9H-purin-6-amine;

9-ethyl-8-(2-methylpyrimidin-5-yl)-N-{(1R)-1-[(S-3-methylpyrrolidin-1-yl)carbonyl]propyl}-9H-purin-6-amine;

9-ethyl-8-(2-methylpyrimidin-5-yl)-N-{(1R)-1-[(R-3-methylpyrrolidin-1-yl)carbonyl]propyl}-9H-purin-6-amine;

9-ethyl-N-{1-[(3-methoxypyrrolidin-1-yl)carbonyl]propyl}-8-(2-methylpyrimidin-5-yl)-9H-purin-6-amine;

9-ethyl-N-{(1S)-1-[(S-3-methoxypyrrolidin-1-yl)carbonyl]propyl}-8-(2-methylpyrimidin-5-yl)-9H-purin-6-amine;

9-ethyl-N-{(1S)-1-[(R-3-methoxypyrrolidin-1-yl)carbonyl]propyl}-8-(2-methylpyrimidin-5-yl)-9H-purin-6-amine;

9-ethyl-N-{(1R)-1-[(S-3-methoxypyrrolidin-1-yl)carbonyl]propyl}-8-(2-methylpyrimidin-5-yl)-9H-purin-6-amine;

9-ethyl-N-{(1R)-1-[(R-3-methoxypyrrolidin-1-yl)carbonyl]propyl}-8-(2-methylpyrimidin-5-yl)-9H-purin-6-amine;

9-ethyl-8-(2-methylpyrimidin-5-yl)-N-{1-[(cis-octahydroisoquinolin-2(1H)-ylcarbonyl]propyl}-9H-purin-6-amine;

9-ethyl-8-(2-methylpyrimidin-5-yl)-N—{(R)-1-[(cis)-octahydroisoquinolin-2(1H)-ylcarbonyl]propyl}-9H-purin-6-amine;

9-ethyl-8-(2-methylpyrimidin-5-yl)-N-{(1S)-1-[(cis)-octahydroisoquinolin-2(1H)-ylcarbonyl]propyl}-9H-purin-6-amine;

N-[1-(2-azaspiro[3.4]oct-2-ylcarbonyl)propyl]-9-ethyl-8-(2-methylpyrimidin-5-yl)-9H-purin-6-amine;

N-[(1R)-1-(2-azaspiro[3.4]oct-2-ylcarbonyl)propyl]-9-ethyl-8-(2-methylpyrimidin-5-yl)-9H-purin-6-amine;

N-[(1S)-1-(2-azaspiro[3.4]oct-2-ylcarbonyl)propyl]-9-ethyl-8-(2-methylpyrimidin-5-yl)-9H-purin-6-amine;

N-{1-[(2-cyclopropylpyrrolidin-1-yl)carbonyl]propyl}-9-ethyl-8-(2-methylpyrimidin-5-yl)-9H-purin-6-amine;

N-{(1S)-1-[(R-2-cyclopropylpyrrolidin-1-yl)carbonyl]propyl}-9-ethyl-8-(2-methylpyrimidin-5-yl)-9H-purin-6-amine;

N-{(1S)-1-[(S-2-cyclopropylpyrrolidin-1-yl)carbonyl]propyl}-9-ethyl-8-(2-methylpyrimidin-5-yl)-9H-purin-6-amine;

N-{(1R)-1-[(R-2-cyclopropylpyrrolidin-1-yl)carbonyl]propyl}-9-ethyl-8-(2-methylpyrimidin-5-yl)-9H-purin-6-amine;

N-{(1R)-1-[(S-2-cyclopropylpyrrolidin-1-yl)carbonyl]propyl}-9-ethyl-8-(2-methylpyrimidin-5-yl)-9H-purin-6-amine;

9-ethyl-N-{1-[(3-methylpiperidin-1-yl)carbonyl]propyl}-8-(2-methylpyrimidin-5-yl)-9H-purin-6-amine;

9-ethyl-N-{(1S)-1-[((R)-3-methylpiperidin-1-yl)carbonyl]propyl}-8-(2-methylpyrimidin-5-yl)-9H-purin-6-amine;

9-ethyl-N-{(1S)-1-[((S)-3-methylpiperidin-1-yl)carbonyl]propyl}-8-(2-methylpyrimidin-5-yl)-9H-purin-6-amine;

9-ethyl-N-{(1R)-1-[(R-3-methylpiperidin-1-yl)carbonyl]propyl}-8-(2-methylpyrimidin-5-yl)-9H-purin-6-amine;

9-ethyl-N-{(1R)-1-[(R-3-methylpiperidin-1-yl)carbonyl]propyl}-8-(2-methylpyrimidin-5-yl)-9H-purin-6-amine;

9-ethyl-8-(2-methylpyrimidin-5-yl)-N-{1-[(-2-methyl-1,3-thiazolidin-3-yl)carbonyl]propyl}-9H-purin-6-amine;

9-ethyl-8-(2-methylpyrimidin-5-yl)-N-{(1S)-1-[(S-2-methyl-1,3-thiazolidin-3-yl)carbonyl]propyl}-9H-purin-6-amine;

9-ethyl-8-(2-methylpyrimidin-5-yl)-N-{(1S)-1-[(R-2-methyl-1,3-thiazolidin-3-yl)carbonyl]propyl}-9H-purin-6-amine;

9-ethyl-8-(2-methylpyrimidin-5-yl)-N-{(1R)-1-[(S-2-methyl-1,3-thiazolidin-3-yl)carbonyl]propyl}-9H-purin-6-amine;

9-ethyl-8-(2-methylpyrimidin-5-yl)-N-{(1R)-1-[(R-2-methyl-1,3-thiazolidin-3-yl)carbonyl]propyl}-9H-purin-6-amine;

9-ethyl-8-(2-methylpyrimidin-5-yl)-N-[1-(1,4-oxazepan-4-ylcarbonyl)propyl]-9H-purin-6-amine;

9-ethyl-8-(2-methylpyrimidin-5-yl)-N-[(1S)-1-(1,4-oxazepan-4-ylcarbonyl)propyl]-9H-purin-6-amine;

9-ethyl-8-(2-methylpyrimidin-5-yl)-N-[(1R)-1-(1,4-oxazepan-4-ylcarbonyl)propyl]-9H-purin-6-amine;

9-ethyl-N-[1-{[3-methylmorpholin-4-yl]carbonyl}propyl]-8-(2-methylpyrimidin-5-yl)-9H-purin-6-amine;

9-ethyl-N-[(1S)-1-{[(3S)-3-methylmorpholin-4-yl]carbonyl}propyl]-8-(2-methylpyrimidin-5-yl)-9H-purin-6-amine;

9-ethyl-N-[(1S)-1-{[(3R)-3-methylmorpholin-4-yl]carbonyl}propyl]-8-(2-methylpyrimidin-5-yl)-9H-purin-6-amine;

9-ethyl-N-[(1R)-1-{[(3S)-3-methylmorpholin-4-yl]carbonyl}propyl]-8-(2-methylpyrimidin-5-yl)-9H-purin-6-amine 9-ethyl-N-[(1R)-1-{[(3R)-3-methylmorpholin-4-yl]carbonyl}propyl]-8-(2-methylpyrimidin-5-yl)-9H-purin-6-amine;

9-ethyl-8-(2-methylpyrimidin-5-yl)-N-[1-(8-oxa-5-azaspiro[3.5]non-5-ylcarbonyl)propyl]-9H-purin-6-amine;

9-ethyl-8-(2-methylpyrimidin-5-yl)-N-[(1S)-1-(8-oxa-5-azaspiro[3.5]non-5-ylcarbonyl)propyl]-9H-purin-6-amine;

9-ethyl-8-(2-methylpyrimidin-5-yl)-N-[(1R)-1-(8-oxa-5-azaspiro[3.5]non-5-ylcarbonyl)propyl]-9H-purin-6-amine;

N-{1-[(2-cyclopropylmorpholin-4-yl)carbonyl]propyl}-9-ethyl-8-(2-methylpyrimidin-5-yl)-9H-purin-6-amine;

N-{(1S)-1-[(S-2-cyclopropylmorpholin-4-yl)carbonyl]propyl}-9-ethyl-8-(2-methylpyrimidin-5-yl)-9H-purin-6-amine;

N-{(1S)-1-[(R-2-cyclopropylmorpholin-4-yl)carbonyl]propyl}-9-ethyl-8-(2-methylpyrimidin-5-yl)-9H-purin-6-amine;

N-{(1R)-1-[(R-2-cyclopropylmorpholin-4-yl)carbonyl]propyl}-9-ethyl-8-(2-methylpyrimidin-5-yl)-9H-purin-6-amine;
N-{(1R)-1-[(S-2-cyclopropylmorpholin-4-yl)carbonyl]propyl}-9-ethyl-8-(2-methylpyrimidin-5-yl)-9H-purin-6-amine;
9-ethyl-8-(2-methylpyrimidin-5-yl)-N-[1-(4-oxa-7-azaspiro[2.5]oct-7-ylcarbonyl)propyl]-9H-purin-6-amine;
9-ethyl-8-(2-methylpyrimidin-5-yl)-N-[(1S)-1-(4-oxa-7-azaspiro[2.5]oct-7-ylcarbonyl)propyl]-9H-purin-6-amine;
9-ethyl-8-(2-methylpyrimidin-5-yl)-N-[(1R)-1-(4-oxa-7-azaspiro[2.5]oct-7-ylcarbonyl)propyl]-9H-purin-6-amine;
N-{1-[(3-cyclopropylmorpholin-4-yl)carbonyl]propyl}-9-ethyl-8-(2-methylpyrimidin-5-yl)-9H-purin-6-amine;
N-{(1S)-1-[(S-3-cyclopropylmorpholin-4-yl)carbonyl]propyl}-9-ethyl-8-(2-methylpyrimidin-5-yl)-9H-purin-6-amine;
N-{(1S)-1-[(R-3-cyclopropylmorpholin-4-yl)carbonyl]propyl}-9-ethyl-8-(2-methylpyrimidin-5-yl)-9H-purin-6-amine;
N-{(1R)-1-[(S-3-cyclopropylmorpholin-4-yl)carbonyl]propyl}-9-ethyl-8-(2-methylpyrimidin-5-yl)-9H-purin-6-amine;
N-{(1R)-1-[(R-3-cyclopropylmorpholin-4-yl)carbonyl]propyl}-9-ethyl-8-(2-methylpyrimidin-5-yl)-9H-purin-6-amine;
9-ethyl-8-(2-methylpyrimidin-5-yl)-N-{1-[2-oxa-5-azabicyclo[2.2.1]hept-5-ylcarbonyl]propyl}-9H-purin-6-amine;
9-ethyl-8-(2-methylpyrimidin-5-yl)-N-{(1S)-1-[(1S,4S)-2-oxa-5-azabicyclo[2.2.1]hept-5-ylcarbonyl]propyl}-9H-purin-6-amine;
9-ethyl-8-(2-methylpyrimidin-5-yl)-N-{(1S)-1-[(1R,4R)-2-oxa-5-azabicyclo[2.2.1]hept-5-ylcarbonyl]propyl}-9H-purin-6-amine;
9-ethyl-8-(2-methylpyrimidin-5-yl)-N-{(1S)-1-[(1R,4S)-2-oxa-5-azabicyclo[2.2.1]hept-5-ylcarbonyl]propyl}-9H-purin-6-amine;
9-ethyl-8-(2-methylpyrimidin-5-yl)-N-{(1S)-1-[(1S,4R)-2-oxa-5-azabicyclo[2.2.1]hept-5-ylcarbonyl]propyl}-9H-purin-6-amine;
9-ethyl-8-(2-methylpyrimidin-5-yl)-N—{(1R)-1-[(1S,4S)-2-oxa-5-azabicyclo[2.2.1]hept-5-ylcarbonyl]propyl}-9H-purin-6-amine;
9-ethyl-8-(2-methylpyrimidin-5-yl)-N-{(1R)-1-[(1R,4R)-2-oxa-5-azabicyclo[2.2.1]hept-5-ylcarbonyl]propyl}-9H-purin-6-amine;
9-ethyl-8-(2-methylpyrimidin-5-yl)-N-{(1R)-1-[(1R,4S)-2-oxa-5-azabicyclo[2.2.1]hept-5-ylcarbonyl]propyl}-9H-purin-6-amine;
9-ethyl-8-(2-methylpyrimidin-5-yl)-N-{(1R)-1-[(1S,4R)-2-oxa-5-azabicyclo[2.2.1]hept-5-ylcarbonyl]propyl}-9H-purin-6-amine;
9-ethyl-N-[1-{[3-(1-methylethyl)morpholin-4-yl]carbonyl}propyl]-8-(2-methylpyrimidin-5-yl)-9H-purin-6-amine;
9-ethyl-N-[(1R)-1-{[3-(1-methylethyl)morpholin-4-yl]carbonyl}propyl]-8-(2-methylpyrimidin-5-yl)-9H-purin-6-amine;
9-ethyl-N-[(1S)-1-{[3-(1-methylethyl)morpholin-4-yl]carbonyl}propyl]-8-(2-methylpyrimidin-5-yl)-9H-purin-6-amine;
N-{1-[(2,2-dimethylmorpholin-4-yl)carbonyl]propyl}-9-ethyl-8-(2-methylpyrimidin-5-yl)-9H-purin-6-amine;
N-{(1R)-1-[(2,2-dimethylmorpholin-4-yl)carbonyl]propyl}-9-ethyl-8-(2-methylpyrimidin-5-yl)-9H-purin-6-amine;
N-{(1S)-1-[(2,2-dimethylmorpholin-4-yl)carbonyl]propyl}-9-ethyl-8-(2-methylpyrimidin-5-yl)-9H-purin-6-amine;
N-{1-[(3,3-dimethylmorpholin-4-yl)carbonyl]propyl}-9-ethyl-8-(2-methylpyrimidin-5-yl)-9H-purin-6-amine;
N-{(1S)-1-[(3,3-dimethylmorpholin-4-yl)carbonyl]propyl}-9-ethyl-8-(2-methylpyrimidin-5-yl)-9H-purin-6-amine;
N-{(1R)-1-[(3,3-dimethylmorpholin-4-yl)carbonyl]propyl}-9-ethyl-8-(2-methylpyrimidin-5-yl)-9H-purin-6-amine;
9-ethyl-N-[1-{[2-(methoxymethyl)morpholin-4-yl]carbonyl}propyl]-8-(2-methylpyrimidin-5-yl)-9H-purin-6-amine;
9-ethyl-N-[(1S)-1-{[2-(methoxymethyl)morpholin-4-yl]carbonyl}propyl]-8-(2-methylpyrimidin-5-yl)-9H-purin-6-amine;
9-ethyl-N-[(1R)-1-{[2-(methoxymethyl)morpholin-4-yl]carbonyl}propyl]-8-(2-methylpyrimidin-5-yl)-9H-purin-6-amine;
N-[1-{[2,6-dimethylmorpholin-4-yl]carbonyl}propyl]-9-ethyl-8-(2-methylpyrimidin-5-yl)-9H-purin-6-amine;
N-[(1S)-1-{[(trans)-2,6-dimethylmorpholin-4-yl]carbonyl}propyl]-9-ethyl-8-(2-methylpyrimidin-5-yl)-9H-purin-6-amine;
N-[(1R)-1-{[(trans)-2,6-dimethylmorpholin-4-yl]carbonyl}propyl]-9-ethyl-8-(2-methylpyrimidin-5-yl)-9H-purin-6-amine;
{4-[2-{[9-ethyl-8-(2-methylpyrimidin-5-yl)-9H-purin-6-yl]amino}butanoyl]-morpholin-3-yl}methanol;
{4-[(2S)-2-{[9-ethyl-8-(2-methylpyrimidin-5-yl)-9H-purin-6-yl]amino}butanoyl]-R-morpholin-3-yl}methanol;
{4-[(2S)-2-{[9-ethyl-8-(2-methylpyrimidin-5-yl)-9H-purin-6-yl]amino}butanoyl]-S-morpholin-3-yl}methanol;
{4-[(2R)-2-{[9-ethyl-8-(2-methylpyrimidin-5-yl)-9H-purin-6-yl]amino}butanoyl]-R-morpholin-3-yl}methanol;
{4-[(2R)-2-{[9-ethyl-8-(2-methylpyrimidin-5-yl)-9H-purin-6-yl]amino}butanoyl]-S-morpholin-3-yl}methanol;
9-ethyl-N-[1-(hexahydropyrrolo[1,2-a]pyrazin-2(1H)-ylcarbonyl)propyl]-8-(2-methylpyrimidin-5-yl)-9H-purin-6-amine;
9-ethyl-N-[(1R)-1-(S)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(R)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(S)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(R)-(hexahydropyrrolo[1,2-a]pyrazin-2(1H)-ylcarbonyl)propyl]-8-(2-methylpyrimidin-5-yl)-9H-purin-6-amine;
N-{2-[2,6-dimethylmorpholin-4-yl]-1-methyl-2-oxoethyl}-9-ethyl-8-(2-methylpyrimidin-5-yl)-9H-purin-6-amine;
N-{(1S)-2-[(cis)-2,6-dimethylmorpholin-4-yl]-1-methyl-2-oxoethyl}-9-ethyl-8-(2-methylpyrimidin-5-yl)-9H-purin-6-amine;
N-{(1R)-2-[(cis)-2,6-dimethylmorpholin-4-yl]-1-methyl-2-oxoethyl}-9-ethyl-8-(2-methylpyrimidin-5-yl)-9H-purin-6-amine;
N-{1-cyclopropyl-2-[2,6-dimethylmorpholin-4-yl]-2-oxoethyl}-9-ethyl-8-(2-methylpyrimidin-5-yl)-9H-purin-6-amine;

N-{(1S)-1-cyclopropyl-2-[(cis)-2,6-dimethylmorpholin-4-yl]-2-oxoethyl}-9-ethyl-8-(2-methylpyrimidin-5-yl)-9H-purin-6-amine;
N-{(1R)-1-cyclopropyl-2-[(cis)-2,6-dimethylmorpholin-4-yl]-2-oxoethyl}-9-ethyl-8-(2-methylpyrimidin-5-yl)-9H-purin-6-amine;
4-[2,6-dimethylmorpholin-4-yl]-3-{[9-ethyl-8-(2-methylpyrimidin-5-yl)-9H-purin-6-yl]amino}-4-oxobutanamide;
(3S)-4-[(cis)-2,6-dimethylmorpholin-4-yl]-3-{[9-ethyl-8-(2-methylpyrimidin-5-yl)-9H-purin-6-yl]amino}-4-oxobutanamide;
(3R)-4-[(cis)-2,6-dimethylmorpholin-4-yl]-3-{[9-ethyl-8-(2-methylpyrimidin-5-yl)-9H-purin-6-yl]amino}-4-oxobutanamide;
N-[1-{[2,6-dimethylmorpholin-4-yl]carbonyl}-2,2-dimethylpropyl]-9-ethyl-8-(2-methylpyrimidin-5-yl)-9H-purin-6-amine;
N-[(1S)-1-{[(cis)-2,6-dimethylmorpholin-4-yl]carbonyl}-2,2-dimethylpropyl]-9-ethyl-8-(2-methylpyrimidin-5-yl)-9H-purin-6-amine;
N-[(1R)-1-{[(cis)-2,6-dimethylmorpholin-4-yl]carbonyl}-2,2-dimethylpropyl]-9-ethyl-8-(2-methylpyrimidin-5-yl)-9H-purin-6-amine;
N-{2-[2,6-dimethylmorpholin-4-yl]-2-oxo-1-phenylethyl}-9-ethyl-8-(2-methylpyrimidin-5-yl)-9H-purin-6-amine;
N-{(1S)-2-[(cis)-2,6-dimethylmorpholin-4-yl]-2-oxo-1-phenylethyl}-9-ethyl-8-(2-methylpyrimidin-5-yl)-9H-purin-6-amine;
N-{(1R)-2-[(cis)-2,6-dimethylmorpholin-4-yl]-2-oxo-1-phenylethyl}-9-ethyl-8-(2-methylpyrimidin-5-yl)-9H-purin-6-amine;
N-[1-{[2,6-dimethylmorpholin-4-yl]carbonyl}-3-methylbutyl]-9-ethyl-8-(2-methylpyrimidin-5-yl)-9H-purin-6-amine;
N-[(1S)-1-{[(cis)-2,6-dimethylmorpholin-4-yl]carbonyl}-3-methylbutyl]-9-ethyl-8-(2-methylpyrimidin-5-yl)-9H-purin-6-amine;
N-[(1R)-1-{[(cis)-2,6-dimethylmorpholin-4-yl]carbonyl}-3-methylbutyl]-9-ethyl-8-(2-methylpyrimidin-5-yl)-9H-purin-6-amine;
N-[1-{[2,6-dimethylmorpholin-4-yl]carbonyl}butyl]-9-ethyl-8-(2-methylpyrimidin-5-yl)-9H-purin-6-amine;
N-[(1S)-1-{[(cis)-2,6-dimethylmorpholin-4-yl]carbonyl}butyl]-9-ethyl-8-(2-methylpyrimidin-5-yl)-9H-purin-6-amine;
N-[(1R)-1-{[(cis)-2,6-dimethylmorpholin-4-yl]carbonyl}butyl]-9-ethyl-8-(2-methylpyrimidin-5-yl)-9H-purin-6-amine;
N-[2-[2,6-dimethylmorpholin-4-yl]-1-(methoxymethyl)-2-oxoethyl]-9-ethyl-8-(2-methylpyrimidin-5-yl)-9H-purin-6-amine;
N-[(1S)-2-[(cis)-2,6-dimethylmorpholin-4-yl]-1-(methoxymethyl)-2-oxoethyl]-9-ethyl-8-(2-methylpyrimidin-5-yl)-9H-purin-6-amine;
N-[(1R)-2-[(cis)-2,6-dimethylmorpholin-4-yl]-1-(methoxymethyl)-2-oxoethyl]-9-ethyl-8-(2-methylpyrimidin-5-yl)-9H-purin-6-amine;
3-[2,6-dimethylmorpholin-4-yl]-2-{[9-ethyl-8-(2-methylpyrimidin-5-yl)-9H-purin-6-yl]amino}-3-oxopropan-1-ol;
(2S)-3-[(cis)-2,6-dimethylmorpholin-4-yl]-2-{[9-ethyl-8-(2-methylpyrimidin-5-yl)-9H-purin-6-yl]amino}-3-oxopropan-1-ol;
(2R)-3-[(cis)-2,6-dimethylmorpholin-4-yl]-2-{[9-ethyl-8-(2-methylpyrimidin-5-yl)-9H-purin-6-yl]amino}-3-oxopropan-1-ol;
N-{1-cyclopentyl-2-[2,6-dimethylmorpholin-4-yl]-2-oxoethyl}-9-ethyl-8-(2-methylpyrimidin-5-yl)-9H-purin-6-amine;
N-{(1S)-1-cyclopentyl-2-[(cis)-2,6-dimethylmorpholin-4-yl]-2-oxoethyl}-9-ethyl-8-(2-methylpyrimidin-5-yl)-9H-purin-6-amine;
N-{(1R)-1-cyclopentyl-2-[(cis)-2,6-dimethylmorpholin-4-yl]-2-oxoethyl}-9-ethyl-8-(2-methylpyrimidin-5-yl)-9H-purin-6-amine;
N-[1-{[2,6-dimethylmorpholin-4-yl]carbonyl}-2-methylpropyl]-9-ethyl-8-(2-methylpyrimidin-5-yl)-9H-purin-6-amine;
N-[(1S)-1-{[(cis)-2,6-dimethylmorpholin-4-yl]carbonyl}-2-methylpropyl]-9-ethyl-8-(2-methylpyrimidin-5-yl)-9H-purin-6-amine;
N-[(1R)-1-{[(cis)-2,6-dimethylmorpholin-4-yl]carbonyl}-2-methylpropyl]-9-ethyl-8-(2-methylpyrimidin-5-yl)-9H-purin-6-amine;
4-[2,6-dimethylmorpholin-4-yl]-3-{[9-ethyl-8-(2-methylpyrimidin-5-yl)-9H-purin-6-yl]amino}-2-methyl-4-oxobutan-2-ol;
(3S)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol;
(3R)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol;
3-[2,6-dimethylmorpholin-4-yl]-N~2~-[9-ethyl-8-(2-methylpyrimidin-5-yl)-9H-purin-6-yl]-N~1~,N~1~-dimethyl-3-oxopropane-1,2-diamine;
(2S)-3-[(cis)-2,6-dimethylmorpholin-4-yl]-N~2~-[9-ethyl-8-(2-methylpyrimidin-5-yl)-9H-purin-6-yl]-N~1~,N~1~-dimethyl-3-oxopropane-1,2-diamine;
(2S)-3-[(cis)-2,6-dimethylmorpholin-4-yl]-N~2~-[9-ethyl-8-(2-methylpyrimidin-5-yl)-9H-purin-6-yl]-N~1~,N~1~-dimethyl-3-oxopropane-1,2-diamine;
N-[1-{[2,6-dimethylmorpholin-4-yl]carbonyl}-2-methoxypropyl]-9-ethyl-8-(2-methylpyrimidin-5-yl)-9H-purin-6-amine;
N-[(1S,2R)-1-{[(cis)-2,6-dimethylmorpholin-4-yl]carbonyl}-2-methoxypropyl]-9-ethyl-8-(2-methylpyrimidin-5-yl)-9H-purin-6-amine;
N-[(1S,2S)-1-{[(cis)-2,6-dimethylmorpholin-4-yl]carbonyl}-2-methoxypropyl]-9-ethyl-8-(2-methylpyrimidin-5-yl)-9H-purin-6-amine;
N-[(1R,2R)-1-{[(cis)-2,6-dimethylmorpholin-4-yl]carbonyl}-2-methoxypropyl]-9-ethyl-8-(2-methylpyrimidin-5-yl)-9H-purin-6-amine;
N-[(1R,2S)-1-{[(cis)-2,6-dimethylmorpholin-4-yl]carbonyl}-2-methoxypropyl]-9-ethyl-8-(2-methylpyrimidin-5-yl)-9H-purin-6-amine;
N-{3-[2,6-dimethylmorpholin-4-yl]-1-methyl-3-oxopropyl}-9-ethyl-8-(2-methylpyrimidin-5-yl)-9H-purin-6-amine;
N-{(1S)-3-[(cis)-2,6-dimethylmorpholin-4-yl]-1-methyl-3-oxopropyl}-9-ethyl-8-(2-methylpyrimidin-5-yl)-9H-purin-6-amine;
N-{(1R)-3-[(cis)-2,6-dimethylmorpholin-4-yl]-1-methyl-3-oxopropyl}-9-ethyl-8-(2-methylpyrimidin-5-yl)-9H-purin-6-amine;
N-{3-[2,6-dimethylmorpholin-4-yl]-2-methyl-3-oxopropyl}-9-ethyl-8-(2-methylpyrimidin-5-yl)-9H-purin-6-amine;
N-{(2R)-3-[(cis)-2,6-dimethylmorpholin-4-yl]-2-methyl-3-oxopropyl}-9-ethyl-8-(2-methylpyrimidin-5-yl)-9H-purin-6-amine;

N-{(2S)-3-[(cis)-2,6-dimethylmorpholin-4-yl]-2-methyl-3-oxopropyl}-9-ethyl-8-(2-methylpyrimidin-5-yl)-9H-purin-6-amine;

N-{3-[2,6-dimethylmorpholin-4-yl]-3-oxo-1-phenylpropyl}-9-ethyl-8-(2-methylpyrimidin-5-yl)-9H-purin-6-amine;

N-{(1R)-3-[(cis)-2,6-dimethylmorpholin-4-yl]-3-oxo-1-phenylpropyl}-9-ethyl-8-(2-methylpyrimidin-5-yl)-9H-purin-6-amine;

N-{(1S)-3-[(cis)-2,6-dimethylmorpholin-4-yl]-3-oxo-1-phenylpropyl}-9-ethyl-8-(2-methylpyrimidin-5-yl)-9H-purin-6-amine;

N-[(1-{[(cis)-2,6-dimethylmorpholin-4-yl]carbonyl}cyclopropyl)methyl]-9-ethyl-8-(2-methylpyrimidin-5-yl)-9H-purin-6-amine;

N-{3-[2,6-dimethylmorpholin-4-yl]-1-(1-methylethyl)-3-oxopropyl}-9-ethyl-8-(2-methylpyrimidin-5-yl)-9H-purin-6-amine;

N-{3-[(cis)-2,6-dimethylmorpholin-4-yl]-1-(1-methylethyl)-3-oxopropyl}-9-ethyl-8-(2-methylpyrimidin-5-yl)-9H-purin-6-amine;

N-[(1R)-3-[(cis)-2,6-dimethylmorpholin-4-yl]-1-(1-methylethyl)-3-oxopropyl]-9-ethyl-8-(2-methylpyrimidin-5-yl)-9H-purin-6-amine;

N-[(1S)-3-[(cis)-2,6-dimethylmorpholin-4-yl]-1-(1-methylethyl)-3-oxopropyl]-9-ethyl-8-(2-methylpyrimidin-5-yl)-9H-purin-6-amine;

9-ethyl-N-[1-methyl-3-oxo-3-pyrrolidin-1-ylpropyl]-8-(2-methylpyrimidin-5-yl)-9H-purin-6-amine;

9-ethyl-N-[(1S)-1-methyl-3-oxo-3-pyrrolidin-1-ylpropyl]-8-(2-methylpyrimidin-5-yl)-9H-purin-6-amine, 9-ethyl-N-[(1R)-1-methyl-3-oxo-3-pyrrolidin-1-ylpropyl]-8-(2-methylpyrimidin-5-yl)-9H-purin-6-amine;

9-ethyl-N-[2-methyl-3-oxo-3-pyrrolidin-1-ylpropyl]-8-(2-methylpyrimidin-5-yl)-9H-purin-6-amine;

9-ethyl-N-[(2R)-2-methyl-3-oxo-3-pyrrolidin-1-ylpropyl]-8-(2-methylpyrimidin-5-yl)-9H-purin-6-amine;

9-ethyl-N-[(2S)-2-methyl-3-oxo-3-pyrrolidin-1-ylpropyl]-8-(2-methylpyrimidin-5-yl)-9H-purin-6-amine;

9-ethyl-8-(2-methylpyrimidin-5-yl)-N-{[1-(pyrrolidin-1-ylcarbonyl)cyclopropyl]methyl}-9H-purin-6-amine;

9-ethyl-N-[1-(1-methylethyl)-3-oxo-3-pyrrolidin-1-ylpropyl]-8-(2-methylpyrimidin-5-yl)-9H-purin-6-amine;

9-ethyl-N-[(1R)-1-(1-methylethyl)-3-oxo-3-pyrrolidin-1-ylpropyl]-8-(2-methylpyrimidin-5-yl)-9H-purin-6-amine;

9-ethyl-N-[(1S)-1-(1-methylethyl)-3-oxo-3-pyrrolidin-1-ylpropyl]-8-(2-methylpyrimidin-5-yl)-9H-purin-6-amine;

N-[1-{[2,6-dimethylmorpholin-4-yl]carbonyl}propyl]-3-ethyl-2-(2-methylpyrimidin-5-yl)-3H-imidazo[4,5-b]pyridin-7-amine;

N-[(1S)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine;

N-[(1R)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine;

N-[1-{[2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[(1S)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[(1R)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[1-{[2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2S)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2S)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1R,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-{1-cyclopropyl-2-[2,6-dimethylmorpholin-4-yl]-2-oxoethyl}-3-ethyl-2-(2-methylpyrimidin-5-yl)-3H-imidazo[4,5-b]pyridin-7-amine;

N—{(R)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine;

N—{(S)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine;

3-cyclopropyl-1-(2-{[9-ethyl-8-(2-methylpyrimidin-5-yl)-9H-purin-6-yl]amino}butanoyl)azetidin-3-ol;

(S)-3-cyclopropyl-1-(2-{[9-ethyl-8-(2-methylpyrimidin-5-yl)-9H-purin-6-yl]amino}butanoyl)azetidin-3-ol;

(R)-3-cyclopropyl-1-(2-{[9-ethyl-8-(2-methylpyrimidin-5-yl)-9H-purin-6-yl]amino}butanoyl)azetidin-3-ol;

N-[1-{[4-acetyl-3,5-dimethylpiperazin-1-yl]carbonyl}propyl]-9-ethyl-8-(2-methylpyrimidin-5-yl)-9H-purin-6-amine;

N-[(1S)-1-{[cis-4-acetyl-3,5-dimethylpiperazin-1-yl]carbonyl}propyl]-9-ethyl-8-(2-methylpyrimidin-5-yl)-9H-purin-6-amine;

N-[(1R)-1-{[cis-4-acetyl-3,5-dimethylpiperazin-1-yl]carbonyl}propyl]-9-ethyl-8-(2-methylpyrimidin-5-yl)-9H-purin-6-amine;

9-ethyl-8-(2-methylpyrimidin-5-yl)-N-[1-{[3,4,5-trimethylpiperazin-1-yl]carbonyl}propyl]-9H-purin-6-amine;

9-ethyl-8-(2-methylpyrimidin-5-yl)-N-[(1S)-1-{[cis-3,4,5-trimethylpiperazin-1-yl]carbonyl}propyl]-9H-purin-6-amine;

9-ethyl-8-(2-methylpyrimidin-5-yl)-N-[(1R)-1-{[cis-3,4,5-trimethylpiperazin-1-yl]carbonyl}propyl]-9H-purin-6-amine;

N-[1-{[4,4-difluoro-3,5-dimethylpiperidin-1-yl]carbonyl}propyl]-9-ethyl-8-(2-methylpyrimidin-5-yl)-9H-purin-6-amine;

N-[(1S)-1-{[cis-4,4-difluoro-3,5-dimethylpiperidin-1-yl]carbonyl}propyl]-9-ethyl-8-(2-methylpyrimidin-5-yl)-9H-purin-6-amine;

N-[(1R)-1-{[cis-4,4-difluoro-3,5-dimethylpiperidin-1-yl]carbonyl}propyl]-9-ethyl-8-(2-methylpyrimidin-5-yl)-9H-purin-6-amine;

4-[2-{[9-ethyl-8-(2-methylpyrimidin-5-yl)-9H-purin-6-yl]amino}butanoyl]-1,6-dimethylpiperazin-2-one;

(S)-4-[(2S)-2-{[9-ethyl-8-(2-methylpyrimidin-5-yl)-9H-purin-6-yl]amino}butanoyl]-1,6-dimethylpiperazin-2-one;

(R)-4-[(2S)-2-{[9-ethyl-8-(2-methylpyrimidin-5-yl)-9H-purin-6-yl]amino}butanoyl]-1,6-dimethylpiperazin-2-one;

(S)-4-[(2R)-2-{[9-ethyl-8-(2-methylpyrimidin-5-yl)-9H-purin-6-yl]amino}butanoyl]-1,6-dimethylpiperazin-2-one;

(R)-4-[(2R)-2-{[9-ethyl-8-(2-methylpyrimidin-5-yl)-9H-purin-6-yl]amino}butanoyl]-1,6-dimethylpiperazin-2-one;

4-[(2-{[9-ethyl-8-(2-methylpyrimidin-5-yl)-9H-purin-6-yl]
amino}butanoyl]-6,6-dimethylpiperazin-2-one;
4-[(2S)-2-{[9-ethyl-8-(2-methylpyrimidin-5-yl)-9H-purin-
6-yl]amino}butanoyl]-6,6-dimethylpiperazin-2-one;
4-[(2R)-2-{[9-ethyl-8-(2-methylpyrimidin-5-yl)-9H-purin-
6-yl]amino}butanoyl]-6,6-dimethylpiperazin-2-one;
9-ethyl-N-(1-{[3-(2-methylpropyl)-5,6-dihydro[1,2,4]tri-
azolo[4,3-a]pyrazin-7(8H)-yl]carbonyl}propyl)-8-(2-
methylpyrimidin-5-yl)-9H-purin-6-amine;
(S)-9-ethyl-N-(1-{[1-methyl-3-(1-methylethyl)-1,4,6,7-tet-
rahydro-5H-pyrazolo[4,3-c]pyridin-5-yl]
carbonyl}propyl)-8-(2-methylpyrimidin-5-yl)-9H-purin-
6-amine;
(R)-9-ethyl-N-(1-{[3-(2-methylpropyl)-5,6-dihydro[1,2,4]
triazolo[4,3-a]pyrazin-7(8H)-yl]carbonyl}propyl)-8-(2-
methylpyrimidin-5-yl)-9H-purin-6-amine; and
9-ethyl-N-(1-{[1-methyl-3-(1-methylethyl)-1,4,6,7-tetra-
hydro-5H-pyrazolo[4,3-c]pyridin-5-yl]carbonyl}propyl)-
8-(2-methylpyrimidin-5-yl)-9H-purin-6-amine.

In one embodiment, the compounds of the present invention include those listed below and their pharmaceutically acceptable salts and their stereoisomers thereof:
(R and S)-8-(1-ethyl-5-methyl-1H-pyrazol-4-yl)-9-methyl-
6-[1-(morpholin-4-ylcarbonyl)propoxy]-9H-purine;
(R and S)-8-(1-ethyl-5-methyl-1H-pyrazol-4-yl)-9-methyl-
6-[1-(piperidin-1-ylcarbonyl)propoxy]-9H-purine;
(R and S)—N—[1-(azetidin-1-ylcarbonyl)propyl]-8-(1-
ethyl-5-methyl-1H-pyrazol-4-yl)-9-methyl-9H-purin-6-
amine;
(R and S)—N-(1-{[(cis)-2,6-dimethylmorpholin-4-yl]
carbonyl}propyl)-8-(1-ethyl-5-methyl-1H-pyrazol-4-yl)-
9-methyl-9H-purin-6-amine;
(R and S)—N-{1-[(4,4-difluoropiperidin-1-yl)carbonyl]pro-
pyl}-8-(1-ethyl-5-methyl-1H-pyrazol-4-yl)-9-methyl-
9H-purin-6-amine;
(R or S)-8-(1-ethyl-5-methyl-1H-pyrazol-4-yl)-9-methyl-N-
[1-(morpholin-4-ylcarbonyl)propyl]-9H-purin-6-amine;
(R or S)-8-(1-ethyl-5-methyl-1H-pyrazol-4-yl)-9-methyl-N-
(1-methyl-2-morpholin-4-yl-2-oxoethyl)-9H-purin-6-
amine;
(R or S)-9-ethyl-8-(2-methylpyrimidin-5-yl)-N-[1-(morpho-
lin-4-ylcarbonyl)propyl]-9H-purin-6-amine;
N-[(1R)-1-benzyl-2-morpholin-4-yl-2-oxoethyl]-8-(1-ethyl-
5-methyl-1H-pyrazol-4-yl)-9-methyl-9H-purin-6-amine;
N-[(1S)-1-benzyl-2-morpholin-4-yl-2-oxoethyl]-8-(1-ethyl-
5-methyl-1H-pyrazol-4-yl)-9-methyl-9H-purin-6-amine;
N-{1-[(4,4-difluoropiperidin-1-yl)carbonyl]cyclopropyl}-9-
ethyl-8-(2-methylpyrimidin-5-yl)-9H-purin-6-amine;
8-(difluoromethyl)-N-[(1S)-1-{[(cis)-2,6-dimethylmorpho-
lin-4-yl]carbonyl}propyl]-9-ethyl-9H-purin-6-amine;
8-(difluoromethyl)-N-{(1S)-2-[(cis)-2,6-dimethylmorpho-
lin-4-yl]-1-methyl-2-oxoethyl}-9-ethyl-9H-purin-6-
amine;
N-[(1S)-1-{[(cis)-2,6-dimethylmorpholin-4-yl]
carbonyl}propyl]-9-ethyl-8-(2-methylpyrimidin-5-yl)-
9H-purin-6-amine;
N-[(1S)-1-{[(cis)-2,6-dimethylmorpholin-4-yl]
carbonyl}propyl]-9-ethyl-8-[6-(trifluoromethyl)pyridin-
3-yl]-9H-purin-6-amine;
N-{(1S)-1-[(1,1-dioxidothiomorpholin-4-yl)carbonyl]pro-
pyl}-9-ethyl-8-(2-methylpyrimidin-5-yl)-9H-purin-6-
amine;
9-ethyl-N-{(1S)-1-[(4-methoxyazepan-1-yl)carbonyl]pro-
pyl}-8-((R and S)-2-methylpyrimidin-5-yl)-9H-purin-6-
amine;
9-ethyl-N-[(1S)-1-{[4-(2-methoxyethoxy)piperidin-1-yl]
carbonyl}propyl]-8-(2-methylpyrimidin-5-yl)-9H-purin-
6-amine;
N-[(1S)-1-{[3-(difluoromethyl)azetidin-1-yl]
carbonyl}propyl]-9-ethyl-8-(2-methylpyrimidin-5-yl)-
9H-purin-6-amine;
N-{(1S)-1-[(3,3-difluoropiperidin-1-yl)carbonyl]propyl}-9-
ethyl-8-(2-methylpyrimidin-5-yl)-9H-purin-6-amine;
1-[(2S)-2-{[9-ethyl-8-(2-methylpyrimidin-5-yl)-9H-purin-
6-yl]amino}butanoyl]piperidine-4-carbonitrile;
N-{(1S)-1-[((3a(R and S), 6a(R and S)-1,1-dioxidohexa-
hydro-5H-thieno[2,3-c]pyrrol-5-yl)carbonyl]propyl}-9-
ethyl-8-(2-methylpyrimidin-5-yl)-9H-purin-6-amine;
9-ethyl-N-[(1S)-1-{[(3S)-3-fluoropyrrolidin-1-yl]
carbonyl}propyl]-8-(2-methylpyrimidin-5-yl)-9H-purin-
6-amine;
9-ethyl-N-[(1S)-1-{[(3R)-3-fluoropyrrolidin-1-yl]
carbonyl}propyl]-8-(2-methylpyrimidin-5-yl)-9H-purin-
6-amine;
9-ethyl-N-{(1S)-1-[(3-methoxyazetidin-1-yl)carbonyl]pro-
pyl}-8-(2-methylpyrimidin-5-yl)-9H-purin-6-amine;
9-ethyl-8-(2-methylpyrimidin-5-yl)-N-{(1S)-1-[((S and
R)-3-methylpyrrolidin-1-yl)carbonyl]propyl}-9H-purin-
6-amine;
9-ethyl-N-{(1S)-1-[((S and R)-3-methoxypyrrolidin-1-yl)
carbonyl]propyl}-8-(2-methylpyrimidin-5-yl)-9H-purin-
6-amine;
9-ethyl-8-(2-methylpyrimidin-5-yl)-N—{(S5)-1-[(cis)-oc-
tahydroisoquinolin-2(1H)-ylcarbonyl]propyl}-9H-purin-
6-amine;
N-[(1S)-1-(2-azaspiro[3.4]oct-2-ylcarbonyl)propyl]-9-
ethyl-8-(2-methylpyrimidin-5-yl)-9H-purin-6-amine;
N-{(1S)-1-[((R and S)-2-cyclopropylpyrrolidin-1-yl)carbo-
nyl]propyl}-9-ethyl-8-(2-methylpyrimidin-5-yl)-9H-pu-
rin-6-amine;
9-ethyl-N-{(1S)-1-[((R and S)-3-methylpiperidin-1-yl)car-
bonyl]propyl}-8-(2-methylpyrimidin-5-yl)-9H-purin-6-
amine;
9-ethyl-8-(2-methylpyrimidin-5-yl)-N-{(1S)-1-[((S and
R)-2-methyl-1,3-thiazolidin-3-yl)carbonyl]propyl}-9H-
purin-6-amine;
9-ethyl-8-(2-methylpyrimidin-5-yl)-N-[(1S)-1-(1,4-oxaze-
pan-4-ylcarbonyl)propyl]-9H-purin-6-amine;
9-ethyl-N-[(1S)-1-{[(3S)-3-methylmorpholin-4-yl]
carbonyl}propyl]-8-(2-methylpyrimidin-5-yl)-9H-purin-
6-amine;
9-ethyl-8-(2-methylpyrimidin-5-yl)-N-[(1S)-1-(8-oxa-5-
azaspiro[3.5]non-5-ylcarbonyl)propyl]-9H-purin-6-
amine;
N-{(1S)-1-[((S and R)-2-cyclopropylmorpholin-4-yl)carbo-
nyl]propyl}-9-ethyl-8-(2-methylpyrimidin-5-yl)-9H-pu-
rin-6-amine;
9-ethyl-8-(2-methylpyrimidin-5-yl)-N-[(1S)-1-(4-oxa-7-
azaspiro[2.5]oct-7-ylcarbonyl)propyl]-9H-purin-6-
amine;
N-{(1S)-1-[((S and R)-3-cyclopropylmorpholin-4-yl)carbo-
nyl]propyl}-9-ethyl-8-(2-methylpyrimidin-5-yl)-9H-pu-
rin-6-amine;
9-ethyl-8-(2-methylpyrimidin-5-yl)-N-{(1S)-1-[(1S,4S)-2-
oxa-5-azabicyclo[2.2.1]hept-5-ylcarbonyl]propyl}-9H-
purin-6-amine;
9-ethyl-N-[(1S)-1-{[3-(1-methylethyl)morpholin-4-yl]
carbonyl}propyl]-8-(2-methylpyrimidin-5-yl)-9H-purin-
6-amine;
N-{(1S)-1-[(2,2-dimethylmorpholin-4-yl)carbonyl]propyl}-
9-ethyl-8-(2-methylpyrimidin-5-yl)-9H-purin-6-amine;

N—{(S)-1-[(3,3-dimethylmorpholin-4-yl)carbonyl]propyl}-9-ethyl-8-(2-methylpyrimidin-5-yl)-9H-purin-6-amine;
9-ethyl-N-[(1S)-1-{[2-(methoxymethyl)morpholin-4-yl]carbonyl}propyl]-8-(2-methylpyrimidin-5-yl)-9H-purin-6-amine;
N-[(1S)-1-{[(trans)-2,6-dimethylmorpholin-4-yl]carbonyl}propyl]-9-ethyl-8-(2-methylpyrimidin-5-yl)-9H-purin-6-amine;
{4-[(2S)-2-{[9-ethyl-8-(2-methylpyrimidin-5-yl)-9H-purin-6-yl]amino}butanoyl]-(R and S)-morpholin-3-yl}methanol;
9-ethyl-N-[(1S)-1-(S and R)-(hexahydropyrrolo[1,2-a]pyrazin-2(1H)-ylcarbonyl)propyl]-8-(2-methylpyrimidin-5-yl)-9H-purin-6-amine;
N-{(1S)-2-[(cis)-2,6-dimethylmorpholin-4-yl]-1-methyl-2-oxoethyl}-9-ethyl-8-(2-methylpyrimidin-5-yl)-9H-purin-6-amine;
N-{(1S)-1-cyclopropyl-2-[(cis)-2,6-dimethylmorpholin-4-yl]-2-oxoethyl}-9-ethyl-8-(2-methylpyrimidin-5-yl)-9H-purin-6-amine;
(3S)-4-[(cis)-2,6-dimethylmorpholin-4-yl]-3-{[9-ethyl-8-(2-methylpyrimidin-5-yl)-9H-purin-6-yl]amino}-4-oxobutanamide;
N-[(1S)-1-{[(cis)-2,6-dimethylmorpholin-4-yl]carbonyl}-2,2-dimethylpropyl]-9-ethyl-8-(2-methylpyrimidin-5-yl)-9H-purin-6-amine;
N-{(1S)-2-[(cis)-2,6-dimethylmorpholin-4-yl]-2-oxo-1-phenylethyl}-9-ethyl-8-(2-methylpyrimidin-5-yl)-9H-purin-6-amine;
N-[(1S)-1-{[(cis)-2,6-dimethylmorpholin-4-yl]carbonyl}-3-methylbutyl]-9-ethyl-8-(2-methylpyrimidin-5-yl)-9H-purin-6-amine;
N-[(1S)-1-{[(cis)-2,6-dimethylmorpholin-4-yl]carbonyl}butyl]-9-ethyl-8-(2-methylpyrimidin-5-yl)-9H-purin-6-amine;
N-[(1S)-2-[(cis)-2,6-dimethylmorpholin-4-yl]-1-(methoxymethyl)-2-oxoethyl]-9-ethyl-8-(2-methylpyrimidin-5-yl)-9H-purin-6-amine;
(2S)-3-[(cis)-2,6-dimethylmorpholin-4-yl]-2-{[9-ethyl-8-(2-methylpyrimidin-5-yl)-9H-purin-6-yl]amino}-3-oxopropan-1-ol;
N-{(1S)-1-cyclopentyl-2-[(cis)-2,6-dimethylmorpholin-4-yl]-2-oxoethyl}-9-ethyl-8-(2-methylpyrimidin-5-yl)-9H-purin-6-amine;
N-[(1S)-1-{[(cis)-2,6-dimethylmorpholin-4-yl]carbonyl}-2-methylpropyl]-9-ethyl-8-(2-methylpyrimidin-5-yl)-9H-purin-6-amine;
(3S)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol;
(2S)-3-[(cis)-2,6-dimethylmorpholin-4-yl]-N~2~-[9-ethyl-8-(2-methylpyrimidin-5-yl)-9H-purin-6-yl]-N~1~,N~1~-dimethyl-3-oxopropane-1,2-diamine;
N-[(1S,2R)-1-{[(cis)-2,6-dimethylmorpholin-4-yl]carbonyl}-2-methoxypropyl]-9-ethyl-8-(2-methylpyrimidin-5-yl)-9H-purin-6-amine;
N-{(1S)-3-[(cis)-2,6-dimethylmorpholin-4-yl]-1-methyl-3-oxopropyl}-9-ethyl-8-(2-methylpyrimidin-5-yl)-9H-purin-6-amine;
N-{(2S)-3-[(cis)-2,6-dimethylmorpholin-4-yl]-2-methyl-3-oxopropyl}-9-ethyl-8-(2-methylpyrimidin-5-yl)-9H-purin-6-amine;
N-{(2R)-3-[(cis)-2,6-dimethylmorpholin-4-yl]-2-methyl-3-oxopropyl}-9-ethyl-8-(2-methylpyrimidin-5-yl)-9H-purin-6-amine;
N-{(1R)-3-[(cis)-2,6-dimethylmorpholin-4-yl]-3-oxo-1-phenylpropyl}-9-ethyl-8-(2-methylpyrimidin-5-yl)-9H-purin-6-amine;
N-[(1-{[(cis)-2,6-dimethylmorpholin-4-yl]carbonyl}cyclopropyl)methyl]-9-ethyl-8-(2-methylpyrimidin-5-yl)-9H-purin-6-amine;
N-[(1R)-3-[(cis)-2,6-dimethylmorpholin-4-yl]-1-(1-methylethyl)-3-oxopropyl]-9-ethyl-8-(2-methylpyrimidin-5-yl)-9H-purin-6-amine;
9-ethyl-N-[(1)-1-methyl-3-oxo-3-pyrrolidin-1-ylpropyl]-8-(2-methylpyrimidin-5-yl)-9H-purin-6-amine;
9-ethyl-N-[(2R)-2-methyl-3-oxo-3-pyrrolidin-1-ylpropyl]-8-(2-methylpyrimidin-5-yl)-9H-purin-6-amine;
9-ethyl-8-(2-methylpyrimidin-5-yl)-N-{[1-(pyrrolidin-1-ylcarbonyl)cyclopropyl]methyl}-9H-purin-6-amine;
9-ethyl-N-[(1R)-1-(1-methylethyl)-3-oxo-3-pyrrolidin-1-ylpropyl]-8-(2-methylpyrimidin-5-yl)-9H-purin-6-amine;
N-[(1S)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine;
N-[(1S)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine;
N-[(1S,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;
N—{(R or S)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine;
(S or R)-3-cyclopropyl-1-(2-{[9-ethyl-8-(2-methylpyrimidin-5-yl)-9H-purin-6-yl]amino}butanoyl)azetidin-3-ol;
N-[(1S)-1-{[cis-4-acetyl-3,5-dimethylpiperazin-1-yl]carbonyl}propyl]-9-ethyl-8-(2-methylpyrimidin-5-yl)-9H-purin-6-amine;
9-ethyl-8-(2-methylpyrimidin-5-yl)-N-[(1S)-1-{[cis-3,4,5-dimethylpiperazin-1-yl]carbonyl}propyl]-9H-purin-6-amine;
N-[(1S)-1-{[cis-4,4-difluoro-3,5-dimethylpiperidin-1-yl]carbonyl}propyl]-9-ethyl-8-(2-methylpyrimidin-5-yl)-9H-purin-6-amine;
(S or R)-4-[(2S)-2-{[9-ethyl-8-(2-methylpyrimidin-5-yl)-9H-purin-6-yl]amino}butanoyl]-1,6-dimethylpiperazin-2-one;
4-[(2S)-2-{[9-ethyl-8-(2-methylpyrimidin-5-yl)-9H-purin-6-yl]amino}butanoyl]-6,6-dimethylpiperazin-2-one;
(S or R)-9-ethyl-N-(1-{[3-(2-methylpropyl)-5,6-dihydro[1,2,4]triazolo[4,3-a]pyrazin-7(8H)-yl]carbonyl}propyl)-8-(2-methylpyrimidin-5-yl)-9H-purin-6-amine; and
(S or R)-9-ethyl-N-(1-{[1-methyl-3-(1-methylethyl)-1,4,6,7-tetrahydro-5H-pyrazolo[4,3-c]pyridin-5-yl]carbonyl}propyl)-8-(2-methylpyrimidin-5-yl)-9H-purin-6-amine.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and exhibit therapeutic activity in medical conditions in which PI3K-delta activity is excessive or undesirable.

The invention is described using the following definitions unless otherwise indicated.

"Acyl" means a —C(O)R radical Where R is optionally substituted alkyl, alkenyl, cycloalkyl, heterocycloalkyl, aryl, heteroaryl, etc.

As used herein except where noted, "alkyl" is intended to include both branched- and straight-chain saturated aliphatic hydrocarbon groups, including all isomers, having the specified number of carbon atoms. Non-limiting examples of alkyl groups include methyl, ethyl, propyl, isopropyl, n-butyl, iso-, s- and t-butyl, pentyl, hexyl, and the like. Commonly used abbreviations for alkyl groups are used throughout the specification, e.g. methyl may be represented by "Me" or $CH_3$, ethyl may be represented by "Et" or $CH_2CH_3$ propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

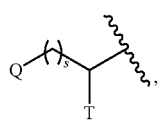

wherein s is an integer equal to zero, 1 or 2, the structure is

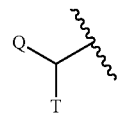

when s is zero.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Carboxy" refers to the functional group —C(O)OR, for example: ethylcarboxy is

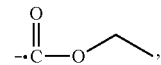

phenylcarboxy is

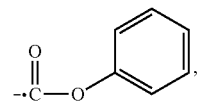

and cyclopropycarboxy is

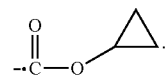

"Carboxyalkyl" refers to an alkyl group substituted with at least one, specifically one or two, —C(O)OH group(s).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

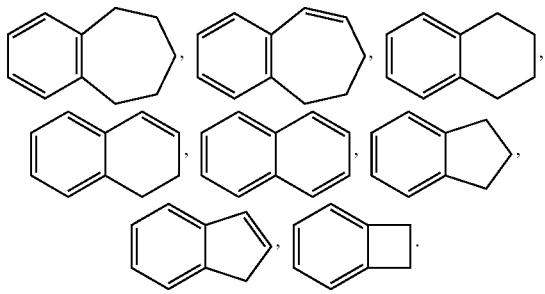

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" or "$C_{3-12}$ cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, spiro[2.5]oxtyl, bicyclo[2.2.2]octane, and the like.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

"Heterocycloalkyl" or "$C_{3-12}$ heterocycloalkyl" refers to a "cycloalkyl" wherein one or more of the carbon atoms are replaced by at least one heteroatom, such as, for example, 1 to 4 heteroatoms selected from nitrogen, oxygen, and sulfur. Nonlimiting examples of heterocycloalkyls include morpholinyl, pyrazolyl, piperazinyl, azetidinyl, azepanyl, thiomorpholinyl, thieno[2,3-c]pyrrolyl, pyrrolidinyl, azaspiro[3.4]octyl, octahydroisoquinolin-2(1H)-yl, piperidinyl, thiazolidinyl, 1,4-oxazepanyl, 8-oxa-5-azaspiro[3.5]non-5-yl, 4-oxa-7-azaspiro[2.5]oxt-7-yl, 5,6-dihydro[1,2,4]triazolo[4,3-a]pyrazin-7(8H)-yl, 1,4,6,7-tetrahydro-5H-pyrazolo[4,3-c]pyridin-5-yl, and 2-oxa-5-azabicylco[2.2.1]hept-5-yl.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, —$CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and contains at least one heteroatom selected from O, S and N. In a bicyclic ring system, the second ring may be a heteroaryl, heterocycle or a saturated, partially unsaturated or aromatic carbocycle, and the point (s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Saturated heterocyclics form a subset of the heterocycles; i.e., the terms "saturated heterocyclic and heterocycloalkyl" generally refers to a heterocycle as defined above in which the entire ring system (whether mono- or poly-cyclic) is saturated. The term "saturated heterocyclic ring" refers to a 3- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, azetidinyl, pyrrolidinyl, pyrazolidinyl, pyrazolyl, imidazolidinyl, oxazolidinyl, isoxazolidinyl, morpholinyl, thiomorpholinyl, thieno[2,3-c]pyrrolyl, thiazolidinyl, isothiazolidinyl, tetrahydrofuryl (or tetrahydrofuranyl), azaspiro[3.4]octyl, octahydroisoquinolin-2(1H)-yl, piperidinyl, thiazolidinyl, 1,4-oxazepanyl, 8-oxa-5-azaspiro[3.5]non-5-yl, 4-oxa-7-azaspiro[2.5]oxt-7-yl, and 2-oxa-5-azabicylco[2.2.1]hept-5-yl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzopyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, pyrazolo[3,4-b]pyridinyl, 4,5,6,7-tetrahydro-1H-benzimidazolyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 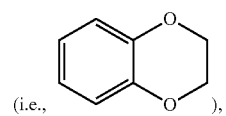), imidazo(2,1-b)(1,3)thiazole, (i.e., 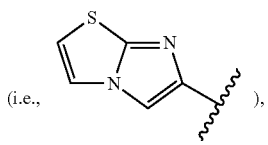 ), and benzo-1,3-dioxolyl (i.e., 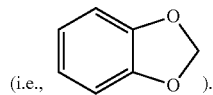 ).

In certain contexts herein,

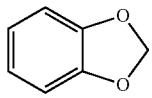

is alternatively referred to as phenyl having as a substituent methylenedioxy attached to two adjacent carbon atoms.

"Heteroalicyclic" group refers to a monocyclic or fused ring of 3 to 12 ring atoms containing one, or more heteroatoms in the ring.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

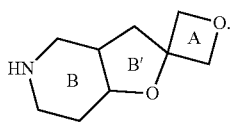

In one embodiment, all rings of the spirocyclyl system are saturated, such as spiro[2.5]octyl. In another embodiment, the individual rings of the spirocyclyl system are selected from both saturated and unsaturated rings.

For example a heteroalicyclic spirocyclyl or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclic rings include azaspiro[2.4]heptyl, 1,9-diazaspiro[5.5]u~decane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa-7-azaspiro[4.5]decane; 1,4-dioxa-7-azaspiro[4.5]decane; 1,4-dioxa-8-azaspiro[4.5]decane, 1,4-dioxa-5-azaspiro[4.5]decane; 8-oxa-5-azaspiro[3.5]non-5-yl; 4-oxa-7-azaspiro[2.5]oxt-7-yl; and 2-oxa-5-azabicyclo[2.2.1]hept-5-yl.

Non-limiting examples of a carbocyclic spirocyclyl systems comprising include: spiro[2.2]pentane, spiro[cyclobutane-1,2'-indene], spiro[4.4]nonane, and spiro[4.5]decane.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g.

"———", i.e., 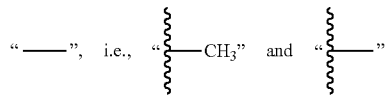

have equivalent meanings.

For variable definitions containing terms having repeated terms, e.g., $(CR_iR_j)_r$, where r is the integer 2, $R_i$ is a defined variable, and $R_j$ is a defined variable, the value of $R_i$ may differ in each instance in which it occurs, and the value of $R_j$ may differ in each instance in which it occurs. For example, if $R_i$ and $R_j$ are independently selected from the group consisting of methyl, ethyl, propyl and butyl, then $(CR_iR_j)_2$ can be

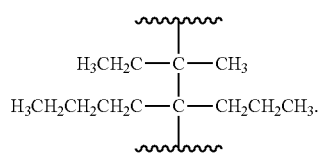

In one embodiment of the invention, $R^1$ is $C_{1-6}$haloalkyl, or a 5- to 6-membered heteroaryl ring, wherein the 5- to 6-membered heteroaryl ring is substituted by 0, 1, 2, or 3 groups independently selected from fluoro, chloro, $C_{1-6}$alkyl, and $C_{1-6}$haloalkyl.

In another embodiment, $R^1$ is selected from difluoromethyl, trifluoromethyl, difluoroethyl, 2,2,2-trifluoroethyl, pyrimidinyl, pyridinyl, and pyrazolyl, wherein pyrimidinyl, pyridinyl and pyrazolyl are substituted by 0, 1, 2, or 3 groups independently selected from fluoro, chloro, $C_{1-6}$alkyl, and $C_{1-6}$haloalkyl.

In a variant of this embodiment, $R^1$ is selected from difluoromethyl, pyrimidinyl, pyridinyl, and pyrazolyl, wherein pyrimidinyl, pyridinyl and pyrazolyl are substituted by 0, 1, 2, or 3 groups independently selected from fluoro, chloro, methyl, ethyl, and trifluoromethyl.

In yet another embodiment, $R^1$ is selected from difluoromethyl, pyrimidinyl, pyridinyl, and pyrazolyl, wherein pyrimidinyl, and pyrazolyl are substituted by 0, 1, 2, or 3 groups independently selected from fluoro, chloro, methyl, ethyl, and trifluoromethyl.

In another embodiment of the invention, $R^2$ is hydrogen or $C_{1-6}$alkyl. In a variant of this embodiment, $R^2$ is selected from methyl, ethyl, propyl, butyl and tert-butyl. In another embodiment, $R^2$ is methyl or ethyl. In a variant of this embodiment, $R^2$ is ethyl.

In yet another embodiment, $R^2$ is hydrogen.

In one embodiment of the invention, L is O or NH. In a variant of this embodiment, L is O. In yet another embodiment, L is NH.

In one embodiment, $R^3$ is each independently selected from hydrogen, $C_{1-10}$alkyl, aryl$C_{0-10}$ alkyl, $C_{3-8}$ cycloalkyl, —($C_{1-10}$ alkyl)OH, $C_{1-10}$ alkoxy$C_{0-10}$ alkyl, and $(C_{0-10}$ alkyl$)_{1-2}$ amino$C_{0-10}$ alkyl and wherein two $R^3$ substituents join together with the carbon to which they are attached to form a propyl or cyclopentyl ring.

In another embodiment, $R^3$ is each independently selected from hydrogen, ethyl, methyl, methylphenyl {benzyl}, cyclopropyl, acetamide, 2,2-dimethylpropyl, phenyl, isobutyl, propyl, methoxymethyl, hydroxymethyl, cyclopentyl, isopropyl, hydroxyisopropyl, dimethylaminomethyl, 2-methoxypropyl, and methoxyeth-1yl.

In another embodiment, two methyl $R^3$ substituents join together with the carbon to which they are attached to form a cyclopropyl ring.

In one embodiment of the invention, $R^4$ is each independently selected from hydrogen and $C_{1-6}$alkyl, wherein two $R^4$ may join together with the carbon to which they are attached to form a 3- to 8-membered ring.

In another embodiment, $R^4$ is each independently hydrogen, methyl or ethyl. In another embodiment two $R^4$ join together with the carbon to which they are attached to form a cyclopropyl ring.

In one embodiment of the invention, n is 0, 1, 2 or 3. In a variant of this embodiment, n is 0, 1 or 2. In yet another embodiment, n is 0 or 1.

In one embodiment of the invention, p is 0, 1, 2 or 3. In a variant of this embodiment, p is 0, 1 or 2.

In one embodiment of the invention, $R^5$ is each independently selected from hydrogen, halogen, $C_{1-6}$alkyl, oxo, cyano, $C_{1-10}$ alkoxy$C_{0-10}$ alkyl(oxy$)_{0-1}$, $C_{1-6}$alkylcarbonyl, $C_{1-6}$haloalkyl, cycloalkyl$C_{0-10}$ alkyl, hydroxy, and —($C_{1-10}$ alkyl)OH.

In another embodiment of the invention, $R^5$ is each independently selected from hydroxy, isopropyl, isobutyl, methylcarbonyl, hydrogen, methyl, fluoro, oxo, methoxy, methoxyethyloxy, difluoromethyl, cyano, cyclopropyl, isopropyl, methoxymethyl, and hydroxymethyl.

In one embodiment of the invention, the group

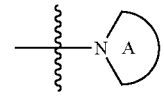

is a $C_{3-12}$heterocycloalkyl having at least one nitrogen, wherein the $C_{3-12}$heterocycloalkyl is bonded to the illustrated carbonyl in the compound of Formula I via a nitrogen atom.

In one embodiment of the invention, the group

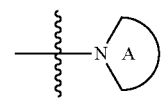

is a spiroheterocyclic ring having at least one nitrogen, wherein the spirohetorocyclic ring is bonded to the illustrated carbonyl of the compound of Formula I via a nitrogen atom.

In another embodiment of the invention, the group

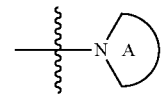

is selected from morpholinyl, piperidinyl, piperazinyl, azetidinyl, thiomorpholinyl, azepanyl, hexahydro-5H-thieno[2,3-c]pyrrolyl, hexahydropyrrolo[1,2-a]pyrazin-2(1H)-yl, pyrrolidinyl, octahydroisoquinolinyl, octahydroisoquinolin-2yl, (cis)-octahydroisoquinolin-2yl, 2-azaspiro[3.4]oct-2yl, thiazolidinyl (1,3-thiazolidinyl), 1,4-oxazepanyl, 8-oxa-5-azaspiro[3.5]non-5yl; 4-oxa-7-azaspiro[2.5]oct-7-yl, 5,6-dihydro[1,2,4]triazolo[4,3-a]pyrazin-7(8H)-yl, 1,4,6,7-tetrahydro-5H-pyrazolo[4,3-c]pyridin-5-yl, and 2-oxa-5-azabicyclo[2.2.1]hept-5yl.

In another embodiment of the invention, the group

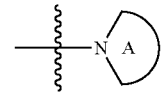

from the compound of Formula I is selected from

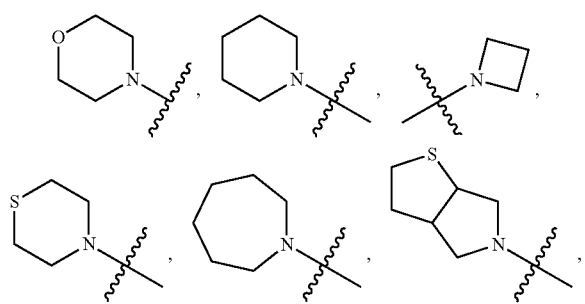

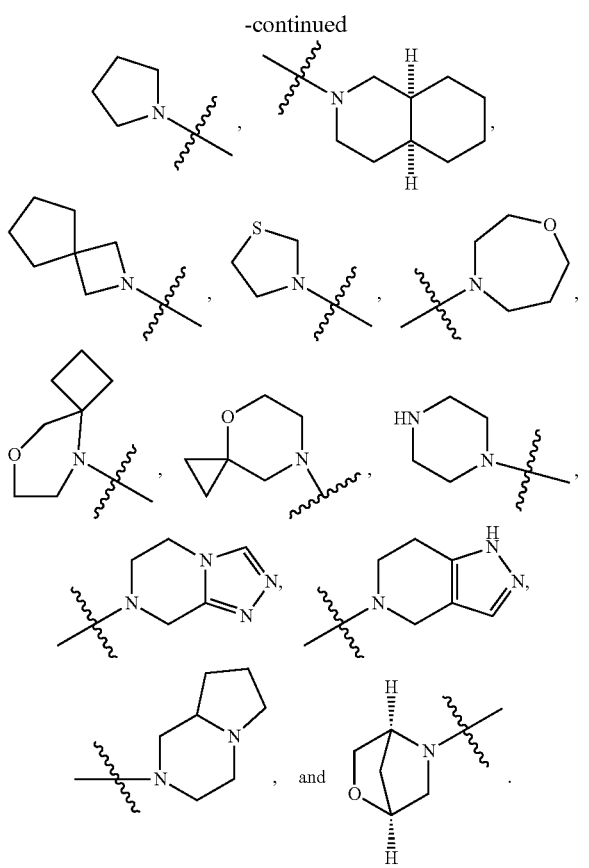

One embodiment of the invention are compounds of formula I or pharmaceutically acceptable salts or stereoisomers thereof:

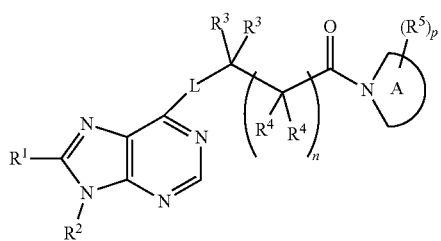

L is O or NH;
R¹ is selected from difluoromethyl, pyrimidinyl, pyridinyl, and pyrazolyl, wherein pyrimidinyl, pyridinyl and pyrazolyl are substituted by 0, 1, 2, or 3 groups independently selected from fluoro, chloro, methyl, ethyl, and trifluoromethyl;
R² is hydrogen or $C_{1-6}$alkyl;
R³ is each independently selected from hydrogen, ethyl, methyl, methylphenyl {benzyl}, cyclopropyl, acetamide, 2,2-dimethylpropyl, phenyl, isobutyl, propyl, methoxymethyl, hydroxymethyl, cyclopentyl, isopropyl, hydroxyisopropyl, dimethylaminoamethyl, 2-methoxypropyl, and methoxyeth-1yl, or two methyl R³ substituents join together with the carbon to which they are attached to form a cyclopropyl ring;
R⁴ is each independently selected from hydrogen, methyl and ethyl, or two R⁴ join together with the carbon to which they are attached to form a cyclopropyl ring;

n is 0, or 1;
p is 0, 1, 2, 3, or 4;
R⁵ is each independently selected from hydroxy, isopropyl, isobutyl, methylcarbonyl, hydrogen, methyl, fluoro, oxo, methoxy, methoxyethyloxy, difluoromethyl, cyano, cyclopropyl, isopropyl, methoxymethyl, and hydroxymethyl;
wherein the group

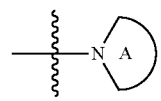

is selected from

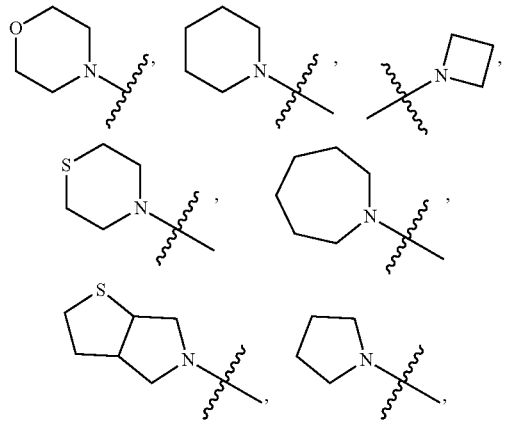

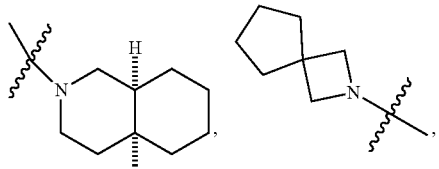

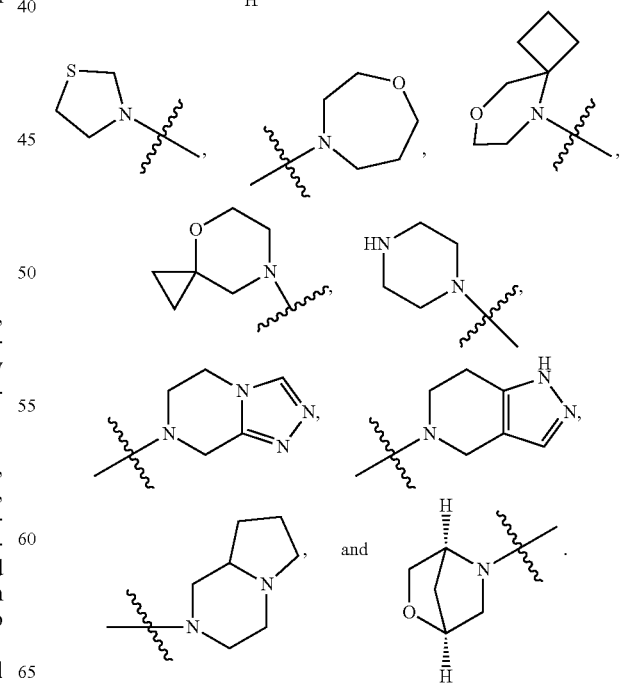

"Patient" for the purposes of the present invention includes humans and other animals, particularly mammals and other organisms. Thus the methods are applicable to both human therapy and beterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^3R^3)_2$—, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

Of course when compounds include reference to a particular orientation, the disclosed orientation is that which is specifically intended. For example, (R)-2-(((9H-fluoren-9-yl)methoxy)carbonylamino)-3-phenylpropanoic acid, specifically refers to the compound with the (R) configuration of the chiral carbon.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (R and S)-8-(1-ethyl-5-methyl-H-pyrazol-4-yl)-9-methyl-6-[1-(piperidin-1-ylcarbonyl)propoxy]-9H-purine, the "and" indicates a racemic mixture of the enantiomers. That is, the individual enantiomers were not individually isolated.

When the stereomeric nomenclature includes "or", for example, (R or S)-8-(1-ethyl-5-methyl-1H-pyrazol-4-yl)-9-methyl-N-(1-methyl-2-morpholin-4-yl-2-oxoethyl)-9H-purin-6-amine, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-$(C_1$-$C_2)$alkyl and piperidino-, pyrrolidino- or morpholino$(C_2$-$C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be envisioned by one of ordinary skill in the art.

Utilities

Compounds of the Invention have activity for PI3K-delta. Compounds of this invention have been tested using the assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta, see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma.

Following the examples disclosed herein, as well as that disclosed in the art, a person of ordinary skill in the art can determine the activity of a compound of this invention.

Compounds of Formula I may be useful for treating diseases, including autoimmune disorders, inflammatory diseases, and cancers, which are listed below.

Cancers:

Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, genninoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune Diseases:

Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases:

asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders:

multiple sclerosis, schizophrenia

Thus, in one embodiment, the invention provides a method of inhibiting PI3K-delta comprising contacting the PI3K-delta with an effective amount of a compound as disclosed herein.

In one embodiment, the compounds of the instant invention are selective PI3K-delta inhibitors relative to PI3K-alpha. The determination of relative selectivity for a given compound of PI3K-delta inhibition is defined as the relative ratio of the (PI3K-alpha $IC_{50}$ value/PI3K-delta $IC_{50}$ value) is at least 2. In yet another embodiment, for a given compound, the relative ratios of the (PI3K-alpha $IC_{50}$ value/PI3K-delta $IC_{50}$ value) is at least 4.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of the disease state. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agent that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (1) TNF-α inhibitors such as Remicade® and Enbrel®); (2) non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

Abbreviations Used in the Description of Compound Preparation

| | |
|---|---|
| Boc | tert-butoxycarbamate |
| BSA | N,O-bis(trimethylsilyl)acetamide |
| COMU | (1-cyano-2-ethoxy-2-oxoethylidenaminooxy)dimethylamino-morpholino-carbenium hexafluorophosphate |
| DAST | (diethylamino)sulfur trifluoride |
| DCM | dichloromethane |
| DEA | diethylamine |
| DIEA | N,N-diisopropylethylamine |
| DMAP | dimethylaminopyridine |
| DME | 1,2 dimethoxyethane |
| DMF | dimethylformamide |
| DMSO | dimethyl sulfoxide |
| dppf | 1,1'-bis(diphenylphosphino)ferrocene |
| EDC | N-(3-dimethylaminopropyl)-N'-ethylcarbodiimide hydrochloride |
| EI | electron ionization |
| ESI | electrospray ionization |
| EtOH | ethanol |
| EtOAc | ethyl acetate |
| GST | Glutathione S-transferase |
| h | hour |
| HATU | 1-[bis(dimethylamino)methylene]-1H-1,2,3-triazolo[4,5-b]pyridinium 3-oxid-hexafluorophosphate |
| HOBT | 1-hydroxybenzotriazole hydrate |
| HPLC | high performance liquid chromatography |
| HTRF | Homogeneous Time Resolved Fluorescence |
| IPA | 2-propanol |
| LC/MS | liquid chromatography coupled to mass spectrometer |
| LHMDS | lithium bis(trimethylsilyl)amide |
| MeCN | acetonitrile |
| MeOH | methanol |
| MS | mass spectrum (data) |
| NMR | nuclear magnetic resonance (data) |
| Pd(dppf)Cl$_2$ | [1,1'-bis(diphenylphosphino)ferrocene]dichloropalladium(II) |
| RT | RT |
| SFC | supercritical fluidic chromatography |
| t-BuOH | tert-butanol |
| TEA | triethylamine |
| TFA | trifluoroacetic acid |
| THF | tetrahydrofuran |

General Synthetic Schemes

Several synthetic routes can be employed in the syntheses of the compounds described herein. In one approach, 4,6-dichloropyrimidine-5-amine is elaborated to a common intermediate Gen-1 by addition of an amine (e.g. $R^2$—$NH_2$) followed by cyclization. For example, oxidative cyclization with an aldehyde $R^1$—CHO would yield the corresponding purine. Another cyclization approach would be to perform a two-step amide coupling and dehydration using a carboxylic acid $R^1$—$CO_2H$. Next, Gen-1 may be elaborated to Gen-2 by addition of the appropriate amine or alcohol nucleophile under basic conditions. For example, reaction with a substituted amino-ester in combination with DIEA under heated conditions would yield the corresponding purinyl glycinate derivative. Finally, Gen-2 may be elaborated to Gen-3 via the addition of an amine under heated conditions to provide the corresponding amide.

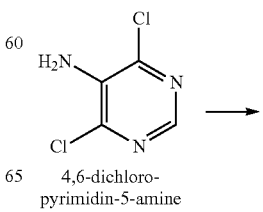

4,6-dichloropyrimidin-5-amine

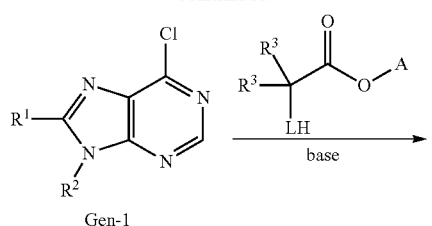

Gen-1

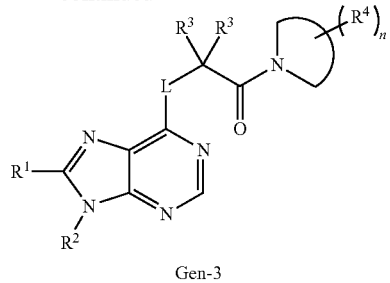

Gen-3

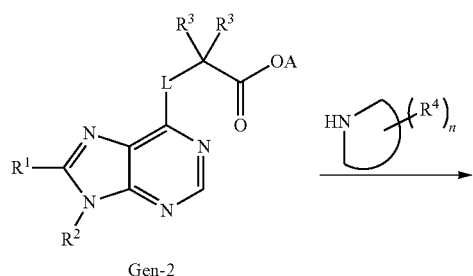

Gen-2

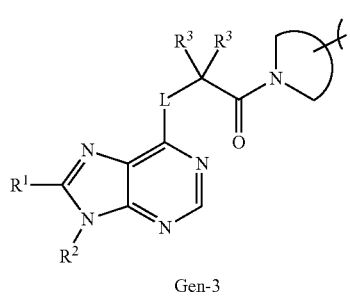

Gen-3

In some cases, Gen-2 may be elaborated to Gen-3 via an acid intermediate Gen-4, which can be obtained via basic hydrolysis of ester Gen-2. Gen-4 is then elaborated to Gen-3 via standard amide coupling conditions and the appropriate amine.

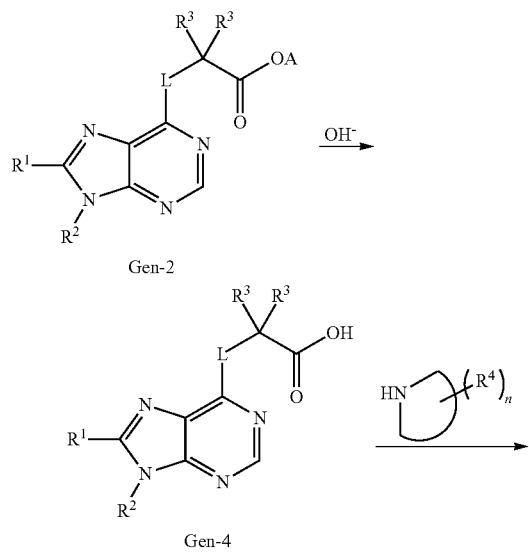

In another approach, a protected acid precursor Gen-5 is elaborated to amide Gen-6 via amide coupling conditions. For example, 3-((tert-butoxycarbonyl)amino)butanoic acid can be converted to tert-butyl-(4-oxo-4-(pyrrolidin-1-yl)butan-2-yl)carbamate through the use of amide-coupling reagent COMU, DIEA, and pyrrolidine. The protecting group (PG) may then be removed under standard conditions to provide Gen-7. An example of this is a Boc group removed under acidic conditions. The resulting free amine or alcohol nucleophile may then be added to purine Gen-1 under basic conditions to provide Gen-8.

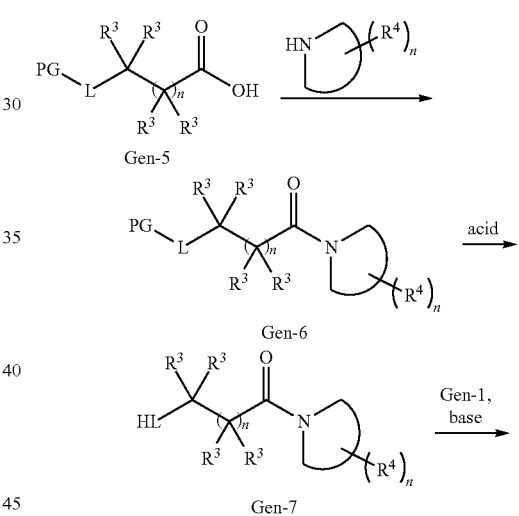

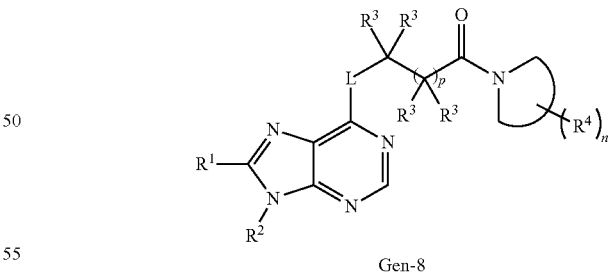

In another approach, an intermediate such as Gen-9 may be obtained from 4-chloro-3-nitropyridin-2-amine via amine alkylation and aryl nitro-group reduction. Gen-9 may then undergo a cyclization event, for example with triethoxyethane, to provide Gen-10. Gen-10 may then be elaborated via halogenation and cross-coupling to Gen-11. Gen-11, in turn, can undergo a second cross-coupling with Gen-6 to provide Gen-12. In some cases, Gen-9 may be elaborated directly to Gen-11. For example, oxidative cyclization of Gen-9 with the appropriate aldehyde would yield Gen-11.

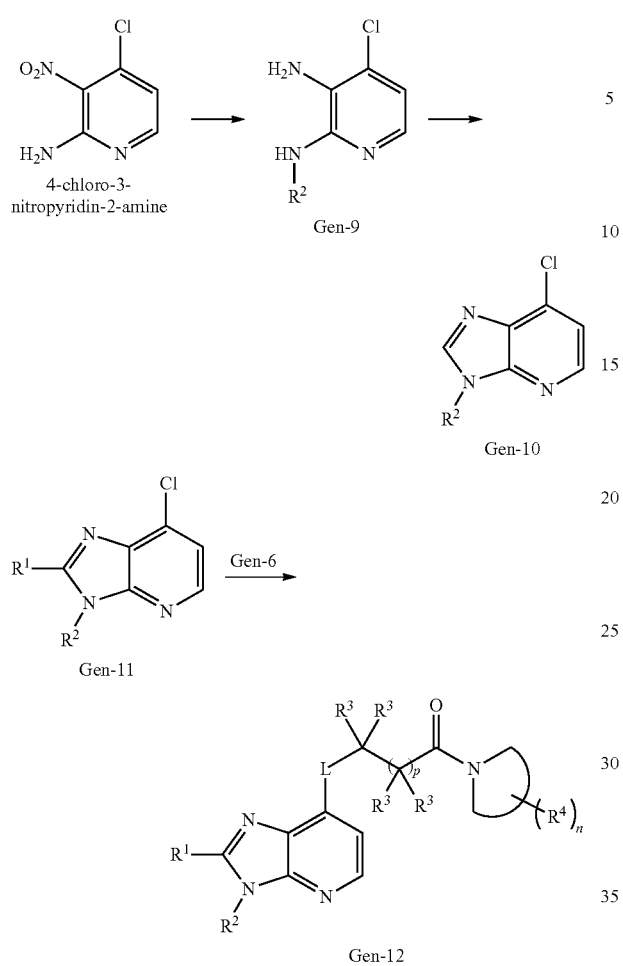

Specific illustrations of these general synthetic approaches can be found in the descriptions of the syntheses of several examples enclosed herein.

Compound Examples of Table 1

Example I-1 Preparation of Compound 1-1

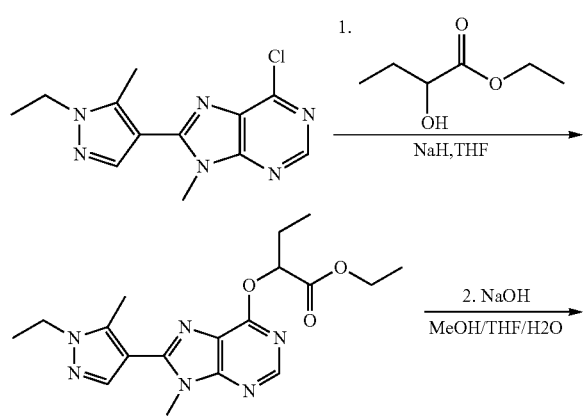

Step 1 Ethyl-2-(8-(1-ethyl-5-methyl-1H-pyrazol-4-yl)-9-methyl-9H-purin-6-yloxy)butanoate To a solution of ethyl 2-hydroxybutanoate (1.0 g, 7.6 mmol) in THF (50 mL) was added NaH (0.2 g, 8.3 mmol) portion-wise at 0° C. The resulting mixture was allowed to warm to RT where it was stirred for 15 min. 6-chloro-8-(1-ethyl-5-methyl-1H-pyrazol-4-yl)-9-methyl-9H-purine[1] (2.1 g, 7.6 mmol) was then added and the reaction was heated to 80° C. and stirred for 16 h. The reaction mixture was then cooled to RT, quenched with MeOH (10 mL), and concentrated in vacuo. The crude reaction mixture was purified by column chromatography (silica gel, eluting with a gradient of EtOAc:hexane from 1:9 to 1:4) to give ethyl-2-(8-(1-ethyl-5-methyl-1H-pyrazol-4-yl)-9-methyl-9H-purin-6-yloxy)butanoate. MS (ESI) calc'd for ($C_{18}H_{25}N_6O_3$) [M+H]$^+$ 373; found 373.

[1]For the preparation of 6-chloro-8-(1-ethyl-5-methyl-1H-pyrazol-4-yl)-9-methyl-9H-purine, and related 6-chloropurines, see Preparation of heterocyclyl-substituted purine derivatives as inhibitors of PI3k-delta for the treatment of cancer. Patrick, Kearney. PCT Int. Appl. (2012); WO 2012/037226.

Step 2 2-(8-(1-ethyl-5-methyl-1H-pyrazol-4-yl)-9-methyl-9H-purin-6-yloxy)butanoic acid To a solution of ethyl-2-(8-(1-ethyl-5-methyl-1H-pyrazol-4-yl)-9-methyl-9H-purin-6-yloxy)butanoate (0.3 g, 0.81 mmol) in a mixture of THF (5 mL), MeOH (10 mL), and H$_2$O (5 mL) was added NaOH (36 mg, 0.89 mmol), after which the reaction mixture was stirred at RT for 3 h. The pH of the mixture was then adjusted to 4 via the addition of aqueous HCl (1 N). The solvent was then removed in vacuo to afford 2-(8-(1-ethyl-5-methyl-1H-pyrazol-4-yl)-9-methyl-9H-purin-6-yloxy)butanoic acid, which was used in the next step without further purification. MS (ESI) calc'd for ($C_{16}H_{21}N_6O_3$) [M+H]$^+$ 345; found 345.

Step 3 Compound 1-1

A mixture of 2-(8-(1-ethyl-5-methyl-1H-pyrazol-4-yl)-9-methyl-9H-purin-6-yloxy)butanoic acid (100 mg, 0.29 mmol), morpholine (25 mg, 0.29 mmol), HATU (122 mg, 0.32 mmol) and DIEA (100 ml, 0.58 mmol) in DMF (2 mL) was stirred at RT for 20 h. The mixture was then purified by column chromatography (combiflash C18, eluting with a gradient of 0-50% MeCN in aqueous $NH_4HCO_3$ (10 mM)) to afford compound 1-1. $^1$H NMR (400 MHz, $CD_3OD$): δ 8.46 (s, 1H), 7.94 (s, 1H), 5.81-5.84 (m, 1H), 4.26 (q, J=7.2 Hz, 2H), 3.84-3.89 (m, 5H), 3.60-3.80 (m, 5H), 3.50-3.60 (m, 1H), 2.56 (s, 3H), 2.00-2.15 (m, 2H), 1.47 (t, J=7.2 Hz, 3H), 1.19 (t, J=7.6 Hz, 3H). MS (ESI) calc'd for ($C_{20}H_{28}N_7O_3$) [M+H]$^+$ 414; found 414.

Example I-2 Preparation of Compound 1-3

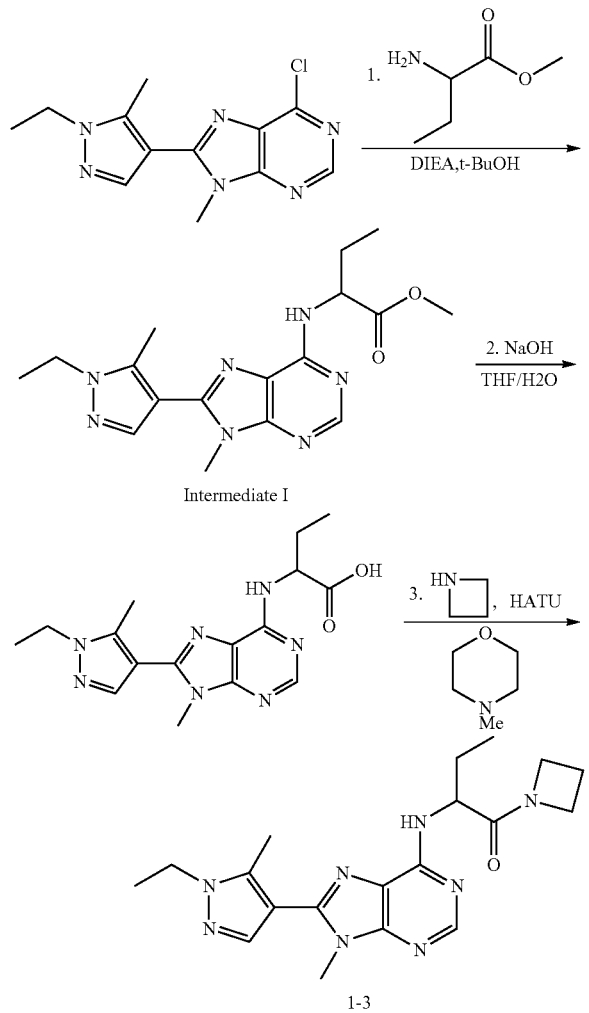

Step 1 Methyl-2-(8-(1-ethyl-5-methyl-1H-pyrazol-4-yl)-9-methyl-9H-purin-6-ylamino)butanoate (Intermediate I)

A mixture of methyl 2-aminobutanoate (500 mg, 3.26 mmol) and 6-chloro-8-(1-ethyl-5-methyl-1H-pyrazol-4-yl)-9-methyl-9H-purine$^1$ (720 mg, 2.60 mmol) was dissolved in t-BuOH (3 mL), after which DIEA (6 mL) was added. The mixture was heated to 90° C. and stirred for 7 days. The reaction was then cooled to RT and concentrated in vacuo, after which it was purified by column chromatography (silica gel, eluting with DCM:MeOH=80:1) to give methyl-2-(8-(1-ethyl-5-methyl-1H-pyrazol-4-yl)-9-methyl-9H-purin-6-ylamino)butanoate (Intermediate I). MS (ESI) calc'd for ($C_{17}H_{24}N_7O_2$) [M+H]$^+$ 358; found 358.

Step 2 2-((8-(1-ethyl-5-methyl-1H-pyrazol-4-yl)-9-methyl-9H-purin-6-yl)amino)butanoic acid To a solution of Intermediate I (1.0 g, 2.8 mmol) in THF (20 ml) and water (4 ml) was added NaOH (0.22 g, 5.6 mmol), and the resulting mixture was stirred at 25° C. for 3 h. The mixture was then concentrated in vacuo, after which the pH of the residue was adjusted to 7 by the addition of aqueous HCl (1N). The mixture was then extracted with EtOAc (2×20 mL), and the combined organic fractions were concentrated in vacuo to afford 2-((8-(1-ethyl-5-methyl-1H-pyrazol-4-yl)-9-methyl-9H-purin-6-yl)amino)butanoic acid, which was used in the next step without further purification. MS (ESI) calc'd for ($C_{16}H_{22}N_7O_2$) [M+H]$^+$ 344; found 344.

Step 3 Compound 1-3

To a solution of 2-((8-(1-ethyl-5-methyl-1H-pyrazol-4-yl)-9-methyl-9H-purin-6-yl)amino)butanoic acid (50 mg, 0.15 mmol) in DMF (2 ml) were added HATU (83 mg, 0.22 mmol) and 4-methylmorpholine (29.5 mg, 0.291 mmol). The resulting solution was stirred at 20° C. for 15 min, after which azetidine (12.5 mg, 0.218 mmol) was added and the solution was further stirred at 20° C. for 15 h. Water (10 mL) was then added and the resulting mixture was extracted with EtOAc (2×10 mL). The combined organic fractions were evaporated under reduced pressure, and the resulting residue was purified by reverse-phase preparative HPLC (C-18, eluting with MeCN in aqueous $NH_4HCO_3$ (10 mM)) to provide compound 1-3. $^1$H NMR (400 MHz, DMSO-d6): δ 8.24 (brs, 1H), 7.94 (s, 1H), 7.29-7.18 (m, 1H), 4.69-4.60 (m, 1H), 4.48-4.42 (m, 1H), 4.19-4.11 (m, 3H), 3.91-3.80 (m, 2H), 3.76 (s, 3H), 2.59 (s, 1H), 2.24-2.13 (m, 2H), 1.90-1.64 (m, 2H), 1.33 (m, 3H), 0.89 (m, 3H). MS (ESI) calc'd for ($C_{19}H_{27}N_8O$) [M+H]$^+$ 383; found 383.

Example I-3 Preparation of Compound 1-6

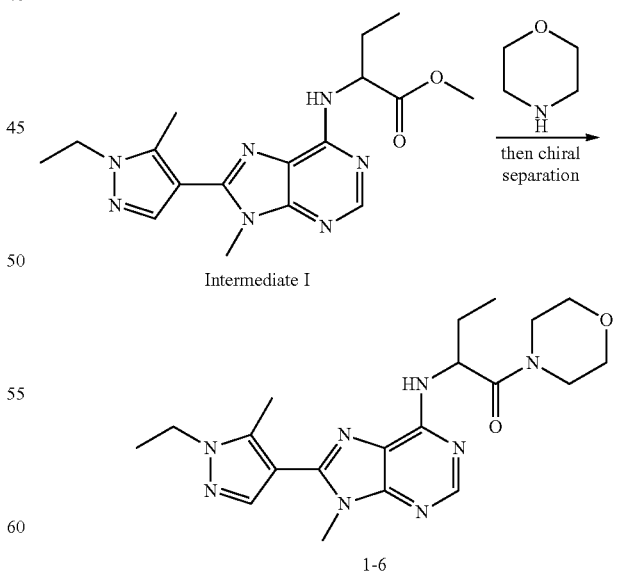

A mixture of Intermediate I (200 mg, 0.56 mmol) and morpholine (2 mL) was heated to 100° C. for 16 h. The mixture was then cooled to RT and concentrated in vacuo. The residue thus obtained was purified by reverse-phase preparative HPLC (eluting with MeCN in aqueous NH$_4$HCO$_3$ (10 mM)) to afford racemic 2-(8-(1-ethyl-5-methyl-1H-pyrazol-4-yl)-9-methyl-9H-purin-6-ylamino)-1-morpholinobutan-1-one. Chiral resolution of the racemic mixture was achieved via chiral preparative SFC (AD-H, 30×250 mm, 5 m; Column temperature: 35° C.; eluting with CO$_2$/MeOH/DEA=60/40/0.1, Flow rate: 70 g/min) to provide 1-6 (faster eluting enantiomer, 2.2 min): $^1$H-NMR (400 MHz, CD$_3$OD): δ 8.16 (s, 1H), 7.79 (s, 1H), 5.20 (s, br, 1H), 4.18-4.12 (m, 2H), 3.71-3.45 (m, 11H), 2.44 (s, 3H), 1.87-1.73 (m, 2H), 1.37-1.33 (m, 3H), 0.96-0.92 (in, 3H). LCMS (ESI) calc'd for (C$_{20}$H$_{29}$N$_8$O$_2$) [M+H]$^+$ 413; found 413.

Example I-4 Preparation of Intermediate III

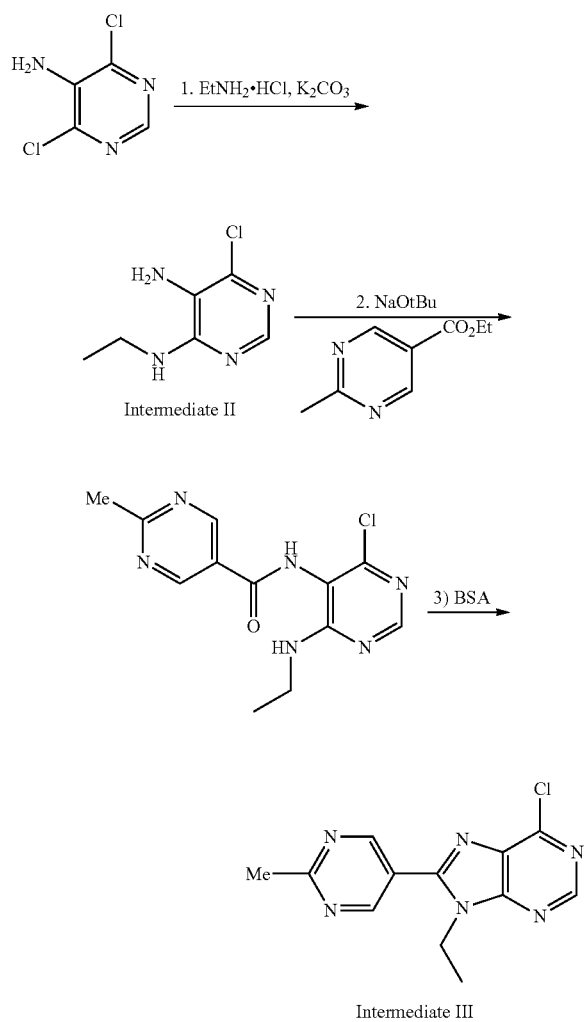

Intermediate II

Intermediate III

Step 1 6-chloro-N$^4$-ethylpyrimidine-4,5-diamine (Intermediate II)

A mixture of 4,6-dichloropyrimidin-5-amine (20.0 g, 122 mmol), ethanamine hydrochloride (EtNH$_2$.HCl) (19.9 g, 243 mmol), and potassium carbonate (50.7 g, 367 mmol) in ethanol (100 ml) was heated to 50° C. for 39 h. The reaction mixture was then cooled to RT, after which it was diluted with DCM (750 ml) and filtered. The filter cake was washed with DCM (250 ml). The combined filtrate was concentrated to dryness to provide 6-chloro-N$^4$-ethylpyrimidine-4,5-diamine. MS (ESI) Calc'd for C$_6$H$_{10}$ClN$_4$ [M+H]$^+$ 173; found 173.

Step 2 N-(4-chloro-6-(ethylamino)pyrimidin-5-yl)-2-methylpyrimidine-5-carboxamide To a mixture of 6-chloro-N$^4$-ethylpyrimidine-4,5-diamine (16 g, 91 mmol) and ethyl-2-methylpyrimidine-5-carboxylate (15 g, 90 mmol) in 50 ml of dimethyl ether at RT, a slurry of sodium tert-butoxide (9.1 g, 92 mmol) in DME (25 ml) was added over the course of 1 min (reaction internal temperature rose to 43° C.). The reaction mixture was then stirred at RT for 2 h, after which it was quenched by the addition of water (75 ml) and EtOAc (75 ml). The reaction mixture was extracted with EtOAc (75 ml×2). The aqueous layer was then charged with acetic acid (5.3 ml, 92 mmol) and a slurry formed. The solid was collected by filtration, then washed with 75 ml of 1:1 DME:water, after which it was dried under vacuum at 35° C. for 16 h to provide N-(4-chloro-6-(ethylamino)pyrimidin-5-yl)-2-methylpyrimidine-5-carboxamide. MS (ESI) Calc'd for C$_{12}$H$_{14}$ClN$_6$O [M+H]$^+$ 293; found 293.

Step 3 6-chloro-9-ethyl-8-(2-methylpyrimidin-5-yl)-9H-purine (Intermediate III)

A vial was charged with BSA (22. ml, 91 mmol), after which N-(4-chloro-6-(ethylamino)pyrimidin-5-yl)-2-methylpyrimidine-5-carboxamide (5.0 g, 17 mmol) was added in portions. The reaction solution was then heated to 55° C. for 1 h, after which it was cooled down to RT. The formed solid was collected by filtration and washed with heptane (15 ml). The solid was then dried under vacuum at 50° C. for 16 h to provide 6-chloro-9-ethyl-8-(2-methylpyrimidin-5-yl)-9H-purine (Intermediate III). MS (ESI) Calc'd for C$_{12}$H$_{12}$ClN$_6$ [M+H]$^+$ 275; found 275.

Compound 1-2 was prepared in an analogous fashion to Example I-1 using piperidine in place of morpholine in step 3.

Compounds 1-4 and 1-5 were prepared in an analogous fashion to Example I-2 using the corresponding amines.

Compound 1-7 was prepared in an analogous fashion to Example I-3 using methyl 2-aminopropanoate in the place of methyl 2-aminobutanoate. Chiral resolution of the racemic mixture was achieved via chiral preparative SFC to provide 1-7.

Compound 1-8 was prepared in an analogous fashion to Example I-3 except that Intermediate III was used in the place of 6-chloro-8-(1-ethyl-5-methyl-1H-pyrazol-4-yl)-9-methyl-9H-purine. Chiral resolution of the racemic mixture was achieved via chiral preparative SFC (Column: OD-H, 30×250 mm, 5 μm, Column temperature: 35° C.) to provide 1-8 (slower eluting enantiomer, 3.2 min).

TABLE 1

| Compound | Structure | IUPAC Name | Exact Mass [M + H]+ |
|---|---|---|---|
| 1-1 | 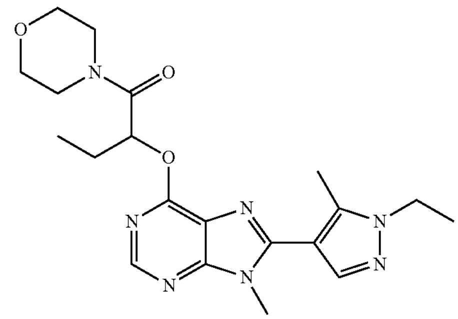 [SMILES: CCC(Oc1ncnc2c1nc(-c1cnn(CC)c1C)n2C)C(=O)N1CCOCC1] | (R and S)-8-(1-ethyl-5-methyl-1H-pyrazol-4-yl)-9-methyl-6-[1-(morpholin-4-ylcarbonyl)propoxy]-9H-purine | Calc'd 414; found 414 |
| 1-2 | 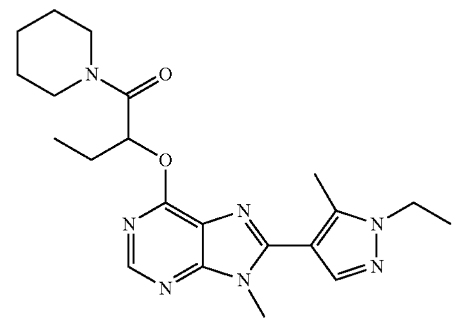 [SMILES: CCC(Oc1ncnc2c1nc(-c1cnn(CC)c1C)n2C)C(=O)N1CCCCC1] | (R and S)-8-(1-ethyl-5-methyl-1H-pyrazol-4-yl)-9-methyl-6-[1-(piperidin-1-ylcarbonyl)propoxy]-9H-purine | Calc'd 412; found 412 |
| 1-3 | 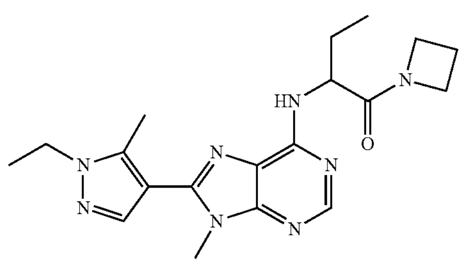 [SMILES: CCC(Nc1ncnc2c1nc(-c1cnn(CC)c1C)n2C)C(=O)N1CCC1] | (R and S)-N-[1-(azetidin-1-ylcarbonyl)propyl]-8-(1-ethyl-5-methyl-1H-pyrazol-4-yl)-9-methyl-9H-purin-6-amine | Calc'd 383; found 383 |
| 1-4 | 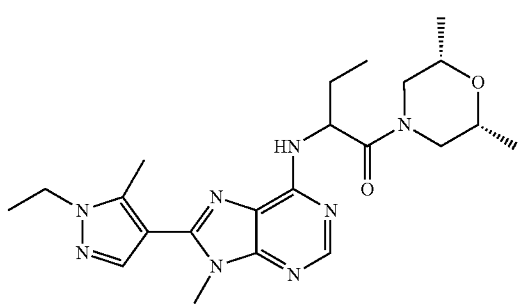 [SMILES: CCC(Nc1ncnc2c1nc(-c1cnn(CC)c1C)n2C)C(=O)N1C[C@@H](C)O[C@@H](C)C1] | (R and S)-N-(1-{[(cis)-2,6-dimethylmorpholin-4-yl]carbonyl}propyl)-8-(1-ethyl-5-methyl-1H-pyrazol-4-yl)-9-methyl-9H-purin-6-amine | Calc'd 441; found 441 |
| 1-5 | 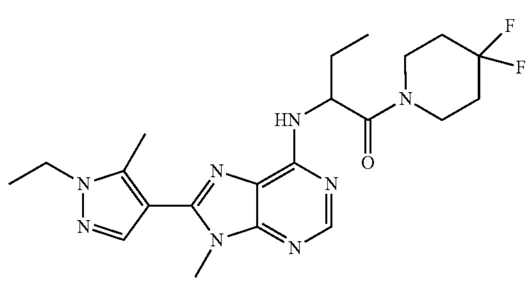 [SMILES: CCC(Nc1ncnc2c1nc(-c1cnn(CC)c1C)n2C)C(=O)N1CCC(F)(F)CC1] | (R and S)-N-{1-[(4,4-difluoropiperidin-1-yl)carbonyl]propyl}-8-(1-ethyl-5-methyl-1H-pyrazol-4-yl)-9-methyl-9H-purin-6-amine | Calc'd 447; found 447 |

TABLE 1-continued

| Compound | Structure | IUPAC Name | Exact Mass [M + H]+ |
|---|---|---|---|
| 1-6 | 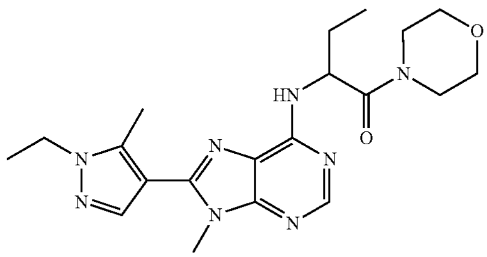 [SMILES: CCC(Nc1ncnc2c1nc(-c1cnn(CC)c1C)n2C)C(=O)N1CCOCC1] | (R or S)-8-(1-ethyl-5-methyl-1H-pyrazol-4-yl)-9-methyl-N-[1-(morpholin-4-ylcarbonyl)propyl]-9H-purin-6-amine | Calc'd 413; found 413 |
| 1-7 | 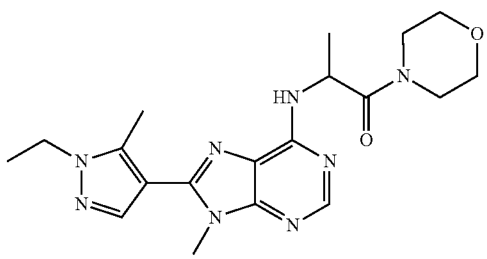 [SMILES: CCn1ncc(-c2nc3c(NC(C)C(=O)N4CCOCC4)ncnc3n2C)c1C] | (R or S)-8-(1-ethyl-5-methyl-1H-pyrazol-4-yl)-9-methyl-N-(1-methyl-2-morpholin-4-yl-2-oxoethyl)-9H-purin-6-amine | Calc'd 399; found 399 |
| 1-8 | 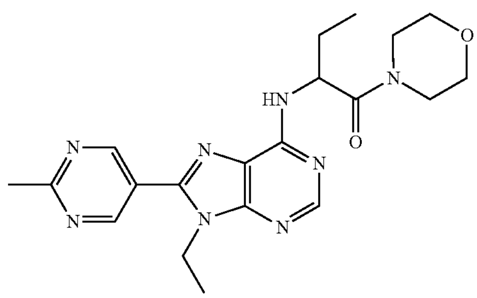 [SMILES: CCC(Nc1ncnc2c1nc(-c1cnc(C)nc1)n2CC)C(=O)N1CCOCC1] | (R or S)-9-ethyl-8-(2-methylpyrimidin-5-yl)-N-[1-(morpholin-4-ylcarbonyl)propyl]-9H-purin-6-amine | Calc'd 411; found 411 |

Compound Examples of Table 2

Example II-1 Preparation of Compound 2-1

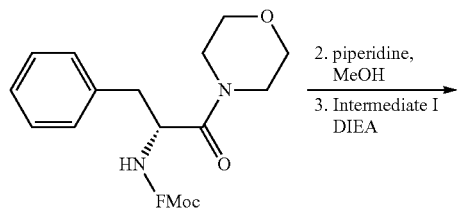

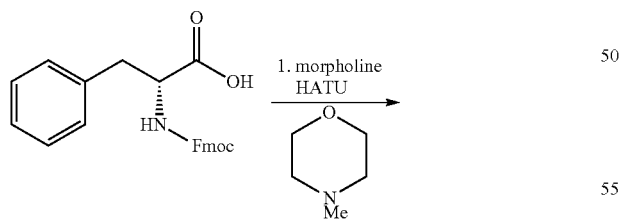

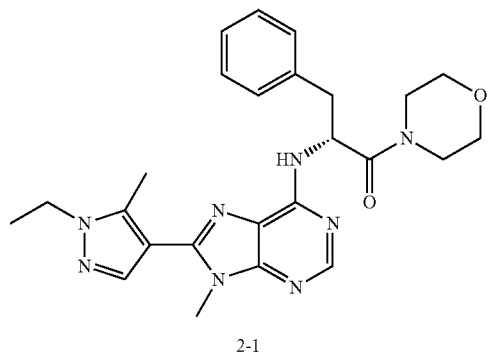

2-1

Step 1 (R)-(9H-fluoren-9-yl)methyl 1-morpholino-1-oxo-3-phenylpropan-2-ylcarbamate A mixture of (R)-2-(((9H-fluoren-9-yl)methoxy)carbonylamino)-3-phenylpropanoic acid (500 mg, 1.3 mmol), morpholine (113 mg, 1.3 mmol), HATU (588 mg, 1.55 mmol), N-Me morpholine (260 mg, 2.6 mmol) and DMF (5.0 mL) was stirred at RT for 16 h. The mixture was then directly purified by preparative HPLC (eluting with MeCN in aqueous NH$_4$HCO$_3$ (10 mM)) to provide (R)-(9H-fluoren-9-yl)methyl 1-morpholino-1-oxo-3-phenylpropan-2-yl-carbamate. MS (ESI) calc'd for ($C_{28}H_{29}N_2O_4$) [M+H]+, 457; found 457.

Step 2
(R)-2-amino-1-morpholino-3-phenylpropan-1-one

To a solution of (R)-(9H-fluoren-9-yl)methyl 1-morpholino-1-oxo-3-phenylpropan-2-ylcarbamate (350 mg, 0.77 mmol) in MeOH (6 mL) was added piperidine (1 mL) at 0° C. The resulting mixture was stirred for 30 min at RT. The reaction mixture was then concentrated in vacuo and subsequently redissolved in MeOH (6 mL) and filtered, after which the filtrate was concentrated in vacuo to provide (R)-2-amino-1-morpholino-3-phenylpropan-1-one, which was used in the next step without further purification. MS (ESI) calc'd for ($C_{13}H_{19}N_2O_2$) [M+H]+, 235; found 235.

Step 3 Compound 2-1

(R)-2-amino-1-morpholino-3-phenylpropan-1-one (200 mg, 0.85 mmol) and Intermediate I (235 mg, 0.85 mmol) were added to the mixture of t-BuOH:DIEA (6:1, 7 mL total). The reaction mixture was then heated to 85° C. for 2 days under an atmosphere of nitrogen. The resulting mixture was then cooled to RT and the solvent was removed in vacuo. The residue was purified by reverse-phase preparative HPLC (eluting with MeCN in aqueous $NH_4HCO_3$ (10 mM)) to provide compound 2-1. 1H NMR (400 MHz, DMSO-d6) δ 8.22 (s, 1H), 7.96 (s, 1H), 7.48 (s, 1H), 7.20-7.28 (m, 5H), 5.41 (s, 1H), 4.19 (q, J=7.2 Hz, 2H), 5.41 (s, 3H), 3.12-3.76 (m, 11H), 2.61 (s, 2H), 1.37 (t, J=7.2 Hz, 3H). MS (ESI) calc'd for ($C_{25}H_{31}N_8O_2$) [M+H]+ 475; found 475.

Example II-2 Compound 2-3

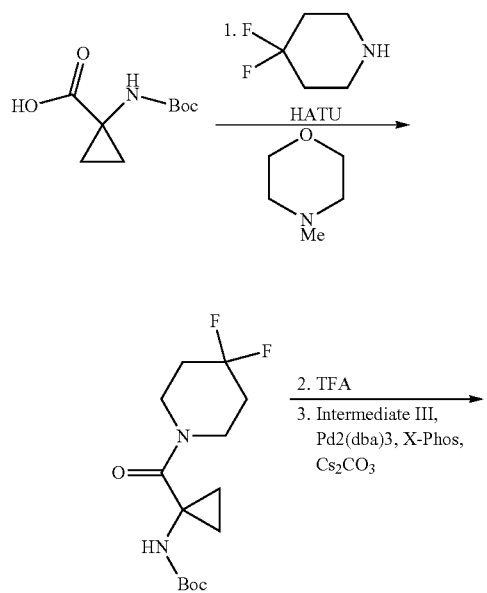

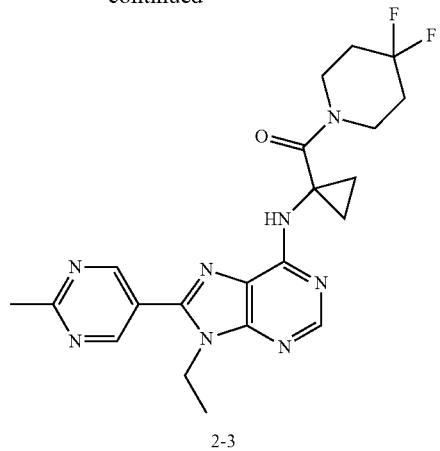

2-3

Step 1 tert-Butyl 1-(4,4-difluoropiperidine-1-carbonyl)cyclopropylcarbamate

To a solution of 1-(tert-butoxycarbonylamino)cyclopropanecarboxylic acid (commercially available from ABCR GmbH & Co.) (600 mg, 3.0 mmol) in DMF (15 ml) was added HATU (1.5 g, 3.9 mmol) and 4-methylmorpholine (0.6 ml, 5.3 mmol). The resulting solution was stirred at 30° C. for 15 min, after which 4,4-difluoropiperidine (300 mg, 2.4 mmol) was added, and the solution was stirred at 30° C. for 15 h. The mixture was then cooled, water (10 mL) was added, and the mixture was extracted with EtOAc (2×10 mL). The combined organic fractions were concentrated in vacuo, and the residue was purified via column chromatography (silica gel, eluting with EtOAc:Petroleum ether (1:3)) to afford the tert-butyl 1-(4,4-difluoropiperidine-1-carbonyl)cyclopropylcarbamate. MS (ESI) calc'd for ($C_{14}H_{23}F_2N_2O_3$) [M+H]+, 305; found 305.

Step 2 (1-Aminocyclopropyl)(4,4-difluoropiperidin-1-yl)methanone 2,2,2-trifluoroacetate To a solution of tert-butyl(1-(4,4-difluoropiperidine-1-carbonyl)cyclopropyl)carbamate (200 mg, 0.65 mmol) in DCM (2 ml) was added TFA (0.5 ml), and the resulting solution was stirred at 20° C. for 3 h. The mixture was concentrated in vacuo to provide (1-aminocyclopropyl)(4,4-difluoropiperidin-1-yl)methanone, which was used directly in the next step without further purification. MS (ESI) calc'd for ($C_9H_{15}F_2N_2O$) [M+H]+, 205; found 205.

Step 3 Compound 2-3

To a solution of (1-aminocyclopropyl)(4,4-difluoropiperidin-1-yl)methanone 2,2,2-trifluoroacetate (90 mg, 0.30 mmol) in toluene (2 ml) was added tris(dibenzylideneacetone)dipalladium(0) (40 mg, 0.04 mmol), 2-(dicyclohexylphosphino)-2',4',6'-triisopropylbiphenyl (X-Phos) (40 mg, 0.08 mmol), Intermediate III (180 mg, 0.65 mmol), and $Cs_2CO_3$ (300 mg, 0.92 mmol). The solution was then stirred at 100° C. for 15 h under an atmosphere of nitrogen. The reaction was then cooled, water (10 mL) was added, and the mixture was extracted with EtOAc (2×10 mL). The combined organic fractions were concentrated in vacuo and the residue was purified by reverse-phase, preparative HPLC (Xbridge Prep C18, 10 µm OBD, 19×250 mm; eluting with MeCN in aqueous NH₄HCO₃ (10 mM); Flow rate: 30 mL/min) to afford compound 2-3. ¹H NMR (400 MHz, CD₃OD) δ 9.15 (s, 2H), 8.37 (s, 1H), 4.52-4.36 (m, 2H), 3.83-3.77 (m, 4H), 2.83 (s, 3H), 1.91-1.77 (m, 4H), 1.60-1.37 (m, 5H), 1.24-1.11 (in, 2H). MS (ESI) calc'd for ($C_{21}H_{25}F_2N_8O$) [M+H]⁺, 443; found 443.

Example II-3 Preparation of Compound 2-4

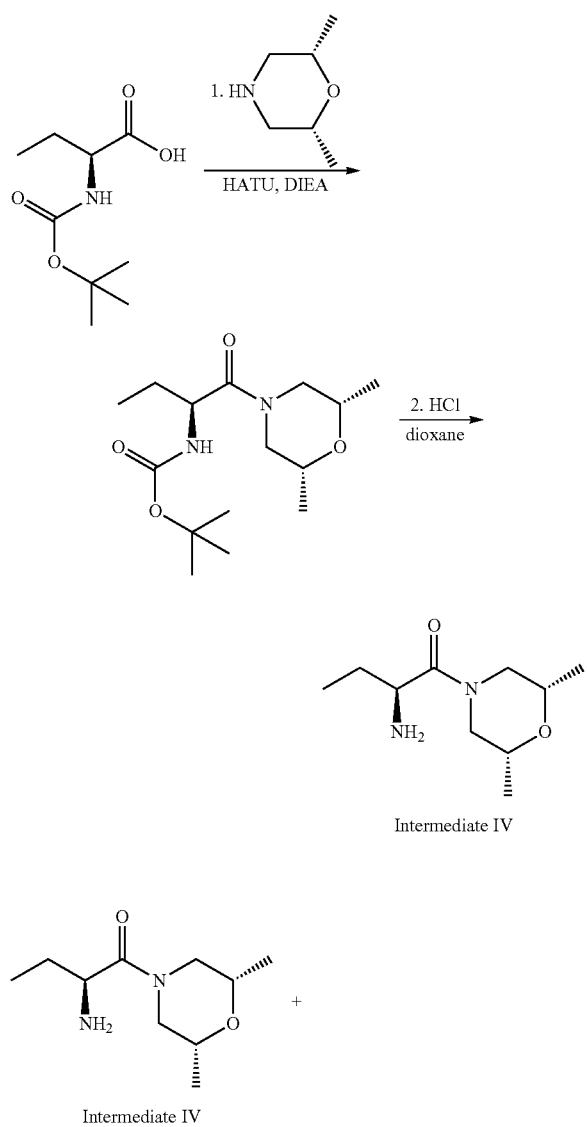

Intermediate IV

Intermediate IV

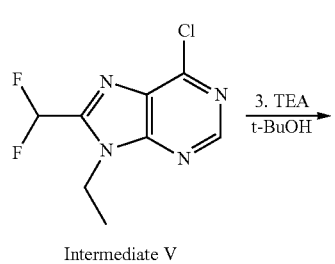

Intermediate V

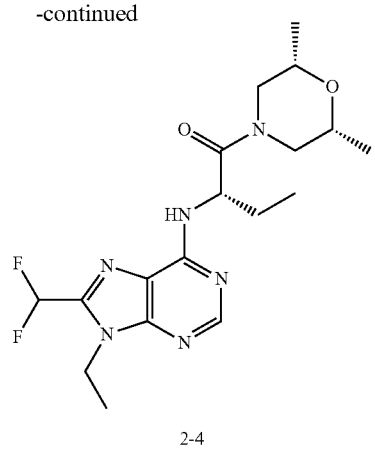

2-4

Step 1 tert-Butyl ((S)-1-((cis)-2,6-dimethylmorpholino)-1-oxobutan-2-yl)carbamate (S)-2-((tert-Butoxycarbonyl)amino)butanoic acid (300 mg, 1.476 mmol) and cis-2,6-dimethylmorpholine (185 µl, 1.48 mmol) were taken up in DMF (3.0 ml) and DIEA (284 µl, 1.62 mmol) was added, followed by HATU (589 mg, 1.55 mmol). The solution was stirred at RT for 18 h. The reaction mixture was diluted with EtOAc and saturated NaHCO₃ was added. The desired products were extracted into EtOAc (3×). The combined organic layers were then washed with saturated aqueous NH₄Cl, followed by brine. The organic layers were then dried over MgSO₄, filtered, and concentrated in vacuo. The resulting tert-butyl ((S)-1-((cis)-2,6-dimethylmorpholino)-1-oxobutan-2-yl)carbamate was carried forward without further purification. MS ESI calc'd. for $C_{11}H_{21}N_2O_4$ [M+2H-tBu]⁺ 245; found 245.

Step 2 (S)-2-Amino-1-((cis)-2,6-dimethylmorpholino)butan-1-one hydrochloride (Intermediate IV)

tert-Butyl ((S)-1-((cis)-2,6-dimethylmorpholino)-1-oxobutan-2-yl)carbamate (440 mg, 1.47 mmol) was taken up in 1,4-dioxane (2 ml) and HCl (4.0 M in 1,4-dioxane, 1.83 ml, 7.32 mmol) was added. The reaction mixture was allowed to stir at RT for 18 hrs. The mixture was then concentrated in vacuo to provide (S)-2-amino-1-((cis)-2,6-dimethylmorpholino)butan-1-one hydrochloride which was used in the next step without further purification. MS ESI calc'd. for $C_{10}H_{21}N_2O_2$ [M+H]⁺ 201; found 201.

Step 3 Compound 2-4

6-chloro-8-(difluoromethyl)-9-ethyl-9H-purine (Intermediate V)² (75 mg, 0.32 mmol) and (S)-2-amino-1-((cis)-2,6-dimethylmorpholino)butan-1-one hydrochloride (77 mg, 0.32 mmol) were taken up in t-BuOH (3.0 ml) and TEA (0.180 ml, 1.29 mmol) was added. The reaction mixture was heated to 80° C. for 18 hours. The products were then extracted into 3:1 chloroform:IPA and the combined organic layers were washed with saturated aqueous NH₄Cl, brine, dried over MgSO₄, and concentrated in vacuo. The residue was taken up in DMF (3 ml) and was purified by reverse-phase mass-triggered preparative HPLC (0-100% MeCN: Water with 0.1% TFA modifier). The desired product was collected and was taken up in 3:1 chloroform-IPA and washed with NaHCO$_3$ (saturated, aqueous). The combined organic layers were washed with brine, dried over MgSO$_4$, filtered, and concentrated in vacuo to give compound 2-4. $^1$H NMR (500 MHz, DMSO-d6) δ 8.32 (s, 1H), 7.39 (t, J=52.5, 1H), 5.13-5.08 (m, 1H), 4.36-4.30 (m, 2H), 4.25-3.95 (m, 3H), 3.56-3.54 (m, 1H), 3.42-3.37 (m, 1H), 2.81-2.77 (m, 1H), 2.36-2.23 (m, 1H), 1.37-1.35 (m, 6H), 1.15-0.92 (m, 8H). MS ESI calc'd. for C$_{18}$H$_{27}$F$_2$N$_6$O$_2$ [M+H]$^+$ 397; found 397.

[2]For the preparation of 6-chloro-8-(difluoromethyl)-9-ethyl-9H-purine (Intermediate V) see Purine inhibitors of human phosphatidylinositol 3-kinase delta. Merck Sharp & Dohme. PCT Int. Appl. (2014); WO 2014/075393.

Example II-4 Preparation of Compound 2-8

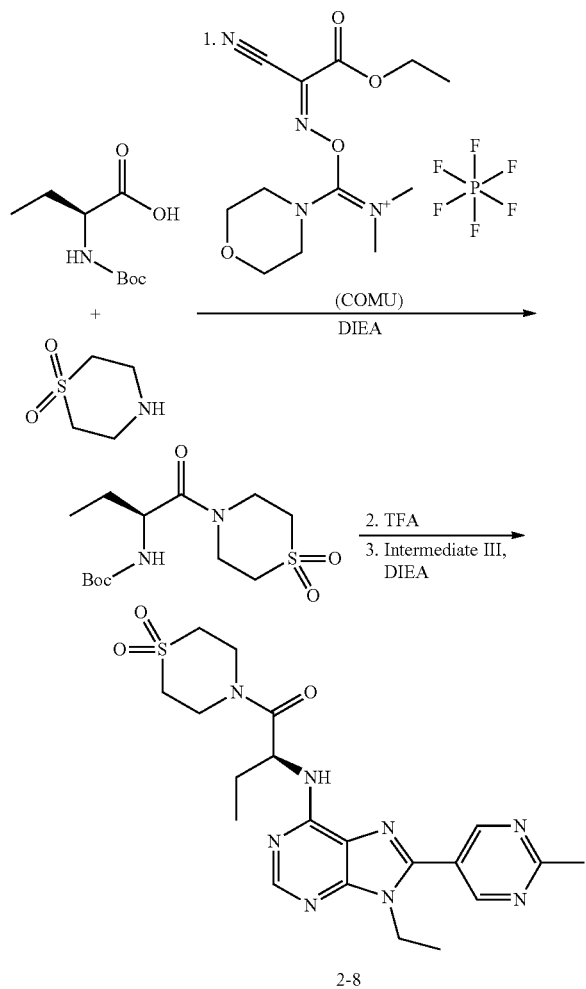

2-8

Step 1 (S)-tert-butyl (1-(1,1-dioxidothiomorpholin)-1-oxobutan-2-yl)carbamate

A vial was charged with (S)-2-((tert-butoxycarbonyl)amino)butanoic acid (40.6 mg, 0.2 mmol), (1-cyano-2-ethoxy-2-oxoethylidenaminooxy)dimethylamino-morpholino-carbenium hexafluorophosphate (COMU) (94.0 mg, 0.22 mmol), and DMF (0.6 ml). The resulting solution was then transferred to a vial containing thiomorpholine 1,1-dioxide (27.0 mg, 0.20 mmol), after which DIEA (100 μl, 0.572 mmol) was added. The resulting mixture was stirred at RT for 18 h, after which DCM (1 ml) and water (1 ml) were added sequentially. The resulting biphasic mixture was passed through a Biotage; Isolute, 120-1905-CG biphasic separatory cartridge to isolate the organic layer, which was then washed with aqueous HCl (0.5N). The resulting solution was concentrated via GeneVac to provide (S)-tert-butyl (1-(1,1-dioxidothiomorpholino)-1-oxobutan-2-yl)carbamate, which was used in the next step without further purification. MS (ESI) Calc'd for C$_{13}$H$_{25}$N$_2$O$_5$S [M+H]$^+$, 321; found 321.

Step 2 (S)-2-amino-1-(1,1-dioxidothiomorpholino)butan-1-one, 2,2,2-trifluoroacetate To a vial containing provide (S)-tert-butyl (1-(1,1-dioxidothiomorpholino)-1-oxobutan-2-yl)carbamate (64 mg, 0.20 mmol) were added DCM (1 ml) and TFA (400 μl, 5.2 mmol). The resulting mixture was stirred at RT for 16 h, after which the volatiles were removed GeneVac to provide (S)-2-amino-1-(1,1-dioxidothiomorpholino)butan-1-one 2,2,2-trifluoroacetate which was used in the next step without further purification.

Step 3 Compound 2-8

To a vial containing (S)-2-amino-1-(1,1-dioxidothiomorpholino)butan-1-one 2,2,2-trifluoroacetate (69 mg, 0.2 mmol) were added Intermediate III (55 mg, 0.20 mmol), t-BuOH (1.76 ml), and DIEA (0.4 ml). The resulting mixture was heated to 90° C. for 17 h. The reaction mixture was then cooled, filtered through a Whatman 24 wells unifilter, (part no. 7700-9917) and purified via reverse-phase preparative HPLC (eluting with a gradient of 0:100 to 95:5 MeCN:water (0.1% v/v NH$_4$OH modifier)) to afford 2-8. $^1$H NMR (600 MHz, DMSO-d6) δ 9.11 (s, 2H), 8.24 (s, 1H), 8.06 (d, J=7.0 Hz, 1H), 5.10-5.00 (m, 1H), 4.37-4.15 (m, 4H), 3.86-3.74 (m, 1H), 3.62-3.30 (m, 2H), 3.25-3.10 (m, 1H), 2.73 (s, 3H), 2.52-2.45 (m, 2H), 1.88-1.76 (m, 2H), 1.34-1.24 (m, 3H), 1.02-0.88 (t, J=7.2 Hz, 3H); MS (EI) Calc'd for C$_{20}$H$_{27}$N$_8$O$_3$S [M+H]$^+$, 459; found 459.

Compound 2-2 was prepared in an analogous manner to Example II-1, except that of (S)-2-(((9H-fluoren-9-yl)methoxy)carbonylamino)-3-phenylpropanoic acid was used in place of (R)-2-(((9H-fluoren-9-yl)methoxy)carbonylamino)-3-phenylpropanoic acid.

Compound 2-5 was prepared in an analogous manner to Example 11-3, except that (S)-2-((tert-butoxycarbonyl)amino)propanoic acid was used in place of (S)-2-((tert-butoxycarbonyl)amino) butanoic acid.

Compound 2-6 was prepared in an analogous manner to Example 11-3, except that Intermediate III was used in place of Intermediate V.

Compound 2-7 was prepared in an analogous manner to Example 11-3, except 6-chloro-9-ethyl-8-(6-(trifluoromethyl)pyridin-3-yl)-9H-purine[3] was used in place of Intermediate V, DIEA was used in place of TEA, and IPA was used in place of t-BuOH.

[3]For the preparation of 6-chloro-9-ethyl-8-(6-(trifluoromethyl)pyridin-3-yl)-9H-purine, see Purine inhibitors of human phosphatidylinositol 3-kinase delta. Merck Sharp & Dohme. PCT Int. Appl. (2014); WO 2014/075393.

Compounds 2-9 through 2-25 were made in an analogous fashion to Example 11-4, using the corresponding amines (all of which are commercially available either through Sigma Aldrich, Matrix Scientific, Ark Pharm Inc., Alfa Aesar, or Enamine Llc).

Compounds 2-26 through 2-37 were prepared in an analogous fashion to Example 11-4, using the corresponding amines (all of which are commercially available through Matrix Scientific, Enamine Llc., Ark Pharm Inc., Synthonix, J&W Pharma, or Astatech Inc.), except that IPA was used in place of t-BuOH as the reaction solvent.

Compound 2-38 was prepared in an analogous fashion to Example II-3 except that octahydropyrrolo[1,2-a]pyrazine was used in place of cis-2,6-dimethylmorpholine, TEA was used in place of DIEA, Intermediate III was used in place of Intermediate V, and TFA in DCM was used in place of HCl in 1,4-dioxane.

Compounds 2-39 through 2-47 were prepared in an analogous fashion to Example II-4 using cis-2,6-dimethylmorpholine and the corresponding amino acids (all of which are commercially available through Sigma Aldrich or Matrix Scientific), except that HCl was used in place of TFA.

Compounds 2-48 through 2-52 were prepared in an analogous fashion to Example II-4 using cis-2,6-dimethylmorpholine and the corresponding amino acids (all of which are commercially available through Sigma Aldrich or Matrix Scientific), except that HCl was used in place of TFA and IPA was used in place of t-BuOH as the reaction solvent.

Compounds 2-53 through 2-58 were prepared in an analogous fashion to Example II-4 using cis-2,6-dimethylmorpholine and the corresponding beta-amino acids (all of which are commercially available through Sigma-Aldrich, Alfa Aesar, or Combi Blocks, Inc.), except that HCl was used in the place of TFA.

Compounds 2-59 through 2-62 were prepared in an analogous fashion to Example II-4 using pyrrolidine and the corresponding beta-amino acids (all of which are commercially available through Sigma-Aldrich, Alfa Aesar, or Combi Blocks, Inc.), except that HCl was used in the place of TFA.

TABLE 2

| Compound | Structure | IUPAC Name | Exact Mass [M + H]+ |
|---|---|---|---|
| 2-1 | 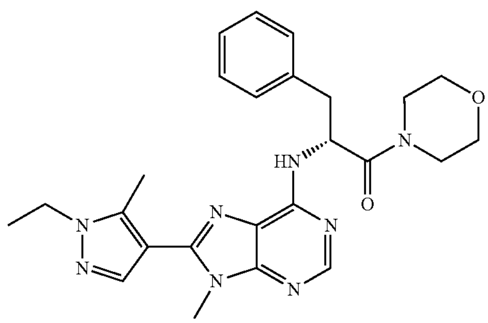 [SMILES: CCn1ncc(-c2nc3c(N[C@H](Cc4ccccc4)C(=O)N4CCOCC4)ncnc3n2C)c1C] | N-[(1R)-1-benzyl-2-morpholin-4-yl-2-oxoethyl]-8-(1-ethyl-5-methyl-1H-pyrazol-4-yl)-9-methyl-9H-purin-6-amine | Calc'd 475; found 475 |
| 2-2 | 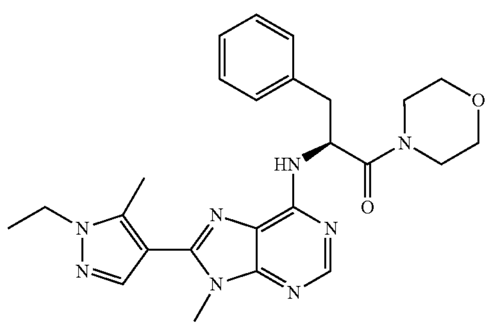 [SMILES: CCn1ncc(-c2nc3c(N[C@@H](Cc4ccccc4)C(=O)N4CCOCC4)ncnc3n2C)c1C] | N-[(1S)-1-benzyl-2-morpholin-4-yl-2-oxoethyl]-8-(1-ethyl-5-methyl-1H-pyrazol-4-yl)-9-methyl-9H-purin-6-amine | Calc'd 475; found 475 |
| 2-3 | 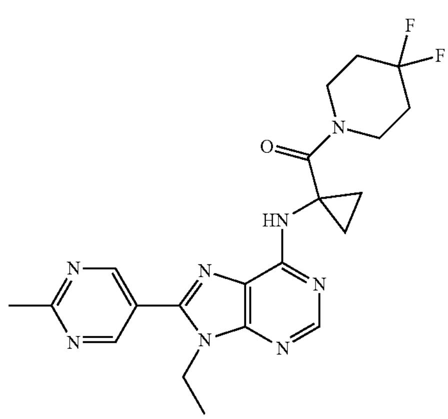 [SMILES: CCn1c(-c2cnc(C)nc2)nc2c(NC3(C(=O)N4CCC(F)(F)CC4)CC3)ncnc21] | N-{1-[(4,4-difluoropiperidin-1-yl)carbonyl]cyclopropyl}-9-ethyl-8-(2-methylpyrimidin-5-yl)-9H-purin-6-amine | Calc'd 443; found 443 |

TABLE 2-continued

| Compound | Structure | IUPAC Name | Exact Mass [M + H]+ |
|---|---|---|---|
| 2-4 | 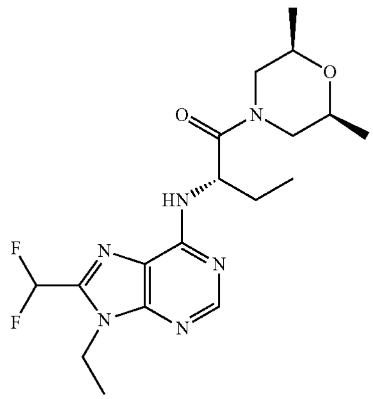 [SMILES: CC[C@H](Nc1ncnc2c1nc(C(F)F)n2CC)C(=O)N1C[C@@H](C)O[C@@H](C)C1] | 8-(difluoromethyl)-N-[(1S)-1-{[(cis)-2,6-dimethylmorpholin-4-yl]carbonyl}propyl]-9-ethyl-9H-purin-6-amine | Calc'd 397; found 397 |
| 2-5 | 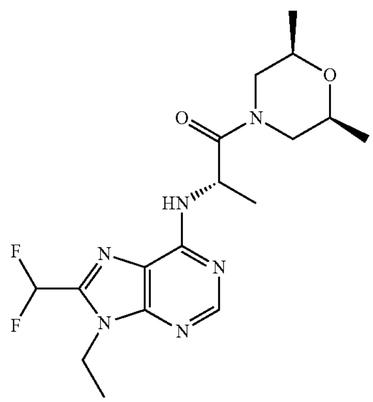 [SMILES: CCn1c(C(F)F)nc2c(N[C@@H](C)C(=O)N3C[C@@H](C)O[C@@H](C)C3)ncnc21] | 8-(difluoromethyl)-N-{(1S)-2-[(cis)-2,6-dimethylmorpholin-4-yl]-1-methyl-2-oxoethyl}-9-ethyl-9H-purin-6-amine | Calc'd 383; found 383 |
| 2-6 | 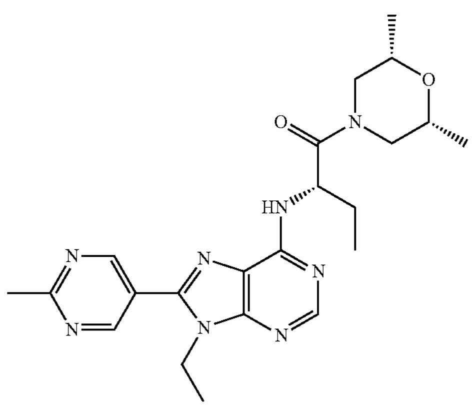 | N-[(1S)-1-{[(cis)-2,6-dimethylmorpholin-4-yl]carbonyl}propyl]-9-ethyl-8-(2-methylpyrimidin-5-yl)-9H-purin-6-amine | Calc'd 439; found 439 |
| 2-7 | 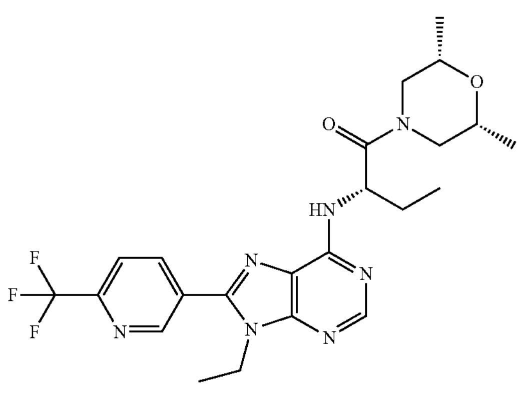 [SMILES: CC[C@H](Nc1ncnc2c1nc(-c1ccc(C(F)(F)F)nc1)n2CC)C(=O)N1C[C@@H](C)O[C@@H](C)C1] | N-[(1S)-1-{[(cis)-2,6-dimethylmorpholin-4-yl]carbonyl}propyl]-9-ethyl-8-[6-(trifluoromethyl)pyridin-3-yl]-9H-purin-6-amine | Calc'd 492; found 492 |

TABLE 2-continued

| Compound | Structure | IUPAC Name | Exact Mass [M + H]+ |
|---|---|---|---|
| 2-8 | 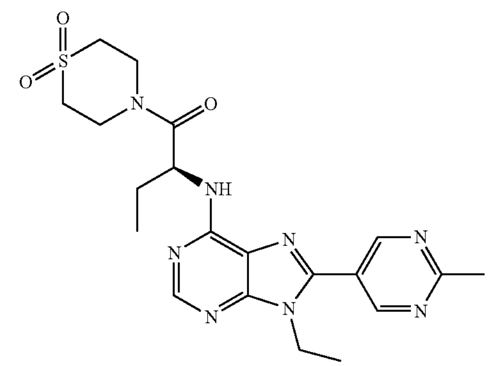 [SMILES: CC[C@H](Nc1ncnc2c1nc(-c1cnc(C)nc1)n2CC)C(=O)N1CCS(=O)(=O)CC1] | N-{(1S)-1-[(1,1-dioxidothiomorpholin-4-yl)carbonyl]propyl}-9-ethyl-8-(2-methylpyrimidin-5-yl)-9H-purin-6-amine | Calc'd 459; found 459 |
| 2-9 | 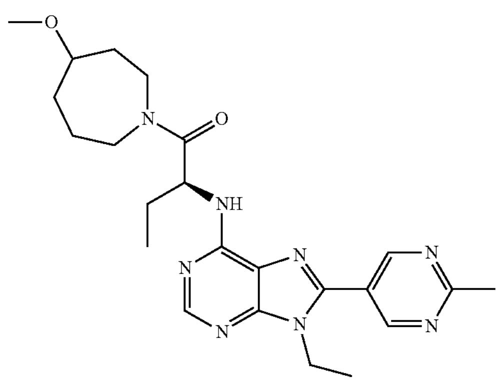 | 9-ethyl-N-{(1S)-1-[(4-methoxyazepan-1-yl)carbonyl]propyl}-8-((R and S)-2-methylpyrimidin-5-yl)-9H-purin-6-amine | Calc'd 453; found 453 |
| 2-10 | 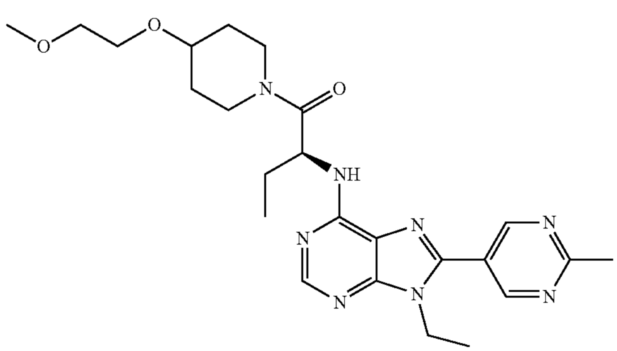 | 9-ethyl-N-[(1S)-1-{[4-(2-methoxyethoxy)piperidin-1-yl]carbonyl}propyl]-8-(2-methylpyrimidin-5-yl)-9H-purin-6-amine | Calc'd 483; found 483 |
| 2-11 | 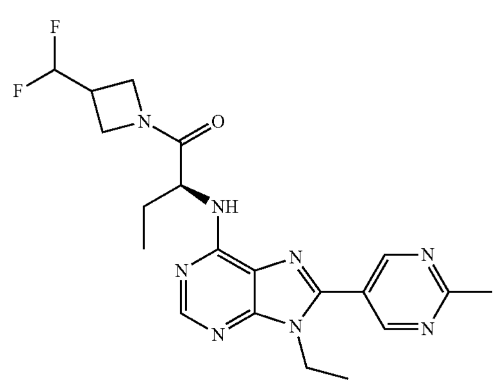 [SMILES: CC[C@H](Nc1ncnc2c1nc(-c1cnc(C)nc1)n2CC)C(=O)N1CC(C(F)F)C1] | N-[(1S)-1-{[3-(difluoromethyl)azetidin-1-yl]carbonyl}propyl]-9-ethyl-8-(2-methylpyrimidin-5-yl)-9H-purin-6-amine | Calc'd 431; found 431 |

TABLE 2-continued

| Compound | Structure | IUPAC Name | Exact Mass [M + H]+ |
|---|---|---|---|
| 2-12 | 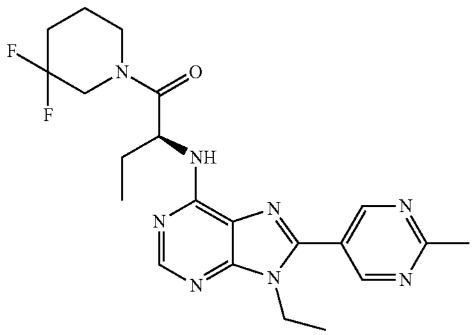 [SMILES: CC[C@H](Nc1ncnc2c1nc(-c1cnc(C)nc1)n2CC)C(=O)N1CCCC(F)(F)C1] | N-{(1S)-1-[(3,3-difluoropiperidin-1-yl)carbonyl]propyl}-9-ethyl-8-(2-methylpyrimidin-5-yl)-9H-purin-6-amine | Calc'd 445; found 445 |
| 2-13 | 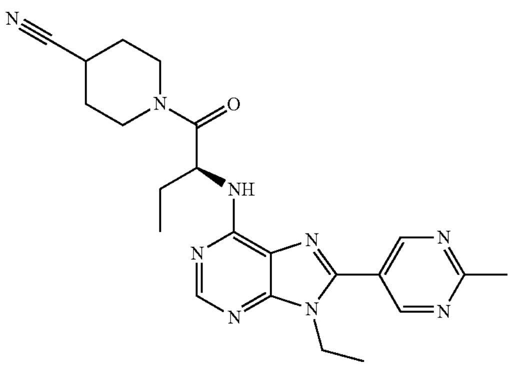 [SMILES: CC[C@H](Nc1ncnc2c1nc(-c1cnc(C)nc1)n2CC)C(=O)N1CCC(C#N)CC1] | 1-[(2S)-2-{[9-ethyl-8-(2-methylpyrimidin-5-yl)-9H-purin-6-yl]amino}butanoyl]piperidine-4-carbonitrile | Calc'd 434; found 434 |
| 2-14 | 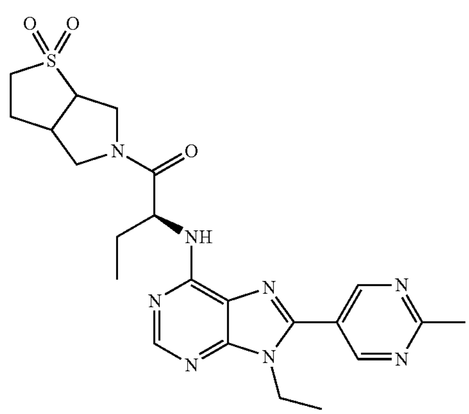 [SMILES: CC[C@H](Nc1ncnc2c1nc(-c1cnc(C)nc1)n2CC)C(=O)N1CC2CCS(=O)(=O)C2C1] | N-{(1S)-1-[((3a(R and S), 6a(R and S)-1,1-dioxidohexahydro-5H-thieno[2,3-c]pyrrol-5-yl)carbonyl]propyl}-9-ethyl-8-(2-methylpyrimidin-5-yl)-9H-purin-6-amine | Calc'd 485; found 485 |
| 2-15 | 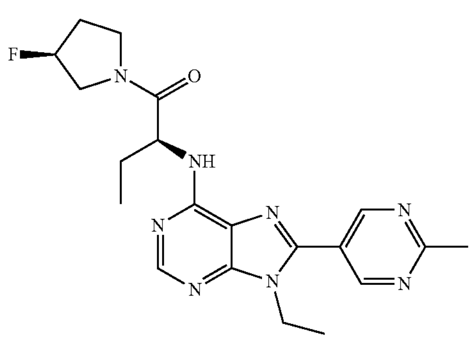 [SMILES: CC[C@H](Nc1ncnc2c1nc(-c1cnc(C)nc1)n2CC)C(=O)N1CC[C@H](F)C1] | 9-ethyl-N-[(1S)-1-{[(3S)-3-fluoropyrrolidin-1-yl]carbonyl}propyl]-8-(2-methylpyrimidin-5-yl)-9H-purin-6-amine | Calc'd 413; found 413 |

TABLE 2-continued

| Compound | Structure | IUPAC Name | Exact Mass [M + H]+ |
|---|---|---|---|
| 2-16 | 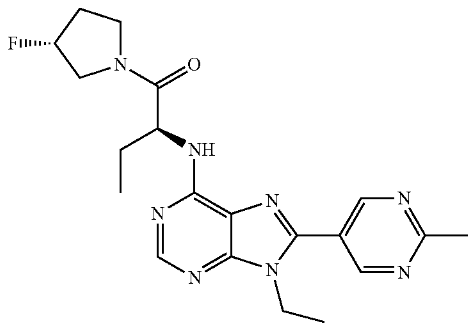 [SMILES: CC[C@H](Nc1ncnc2c1nc(-c1cnc(C)nc1)n2CC)C(=O)N1CC[C@@H](F)C1] | 9-ethyl-N-[(1S)-1-{[(3R)-3-fluoropyrrolidin-1-yl]carbonyl}propyl]-8-(2-methylpyrimidin-5-yl)-9H-purin-6-amine | Calc'd 413; found 413 |
| 2-17 | 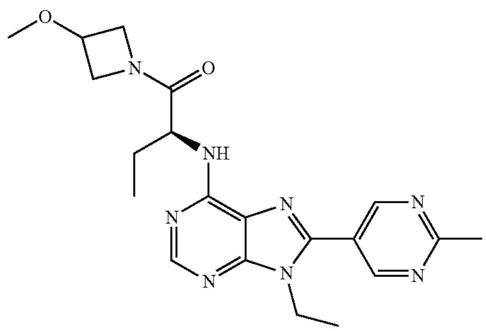 | 9-ethyl-N-{(1S)-1-[(3-methoxyazetidin-1-yl)carbonyl]propyl}-8-(2-methylpyrimidin-5-yl)-9H-purin-6-amine | Calc'd 411; found 411 |
| 2-18 | 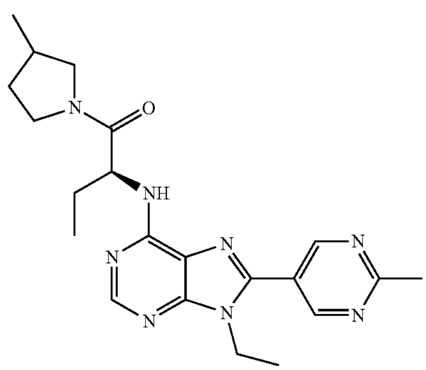 [SMILES: CC[C@H](Nc1ncnc2c1nc(-c1cnc(C)nc1)n2CC)C(=O)N1CCC(C)C1] | 9-ethyl-8-(2-methylpyrimidin-5-yl)-N-{(1S)-1-[((S and R)-3-methylpyrrolidin-1-yl)carbonyl]propyl}-9H-purin-6-amine | Calc'd 409; found 409 |
| 2-19 | 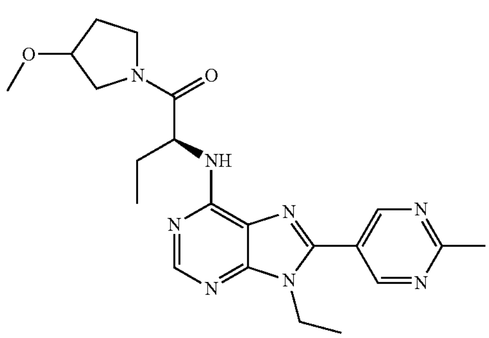 | 9-ethyl-N-{(1S)-1-[((S and R)-3-methoxypyrrolidin-1-yl)carbonyl]propyl}-8-(2-methylpyrimidin-5-yl)-9H-purin-6-amine | Calc'd 425; found 425 |

TABLE 2-continued

| Compound | Structure | IUPAC Name | Exact Mass [M + H]+ |
|---|---|---|---|
| 2-20 | 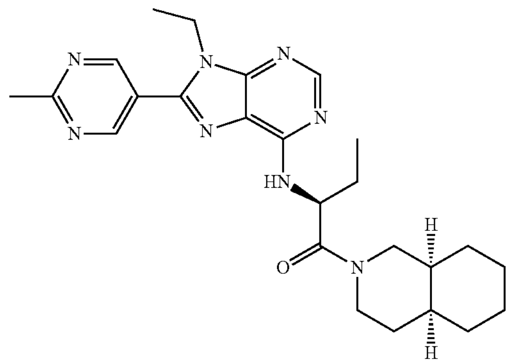 [SMILES: CC[C@H](Nc1ncnc2c1nc(-c1cnc(C)nc1)n2CC)C(=O)N1CC[C@@H]2CCCC[C@@H]2C1] | 9-ethyl-8-(2-methylpyrimidin-5-yl)-N-{(1S)-1-[(cis)-octahydroisoquinolin-2(1H)-ylcarbonyl]propyl}-9H-purin-6-amine | Calc'd 463; found 463 |
| 2-21 | 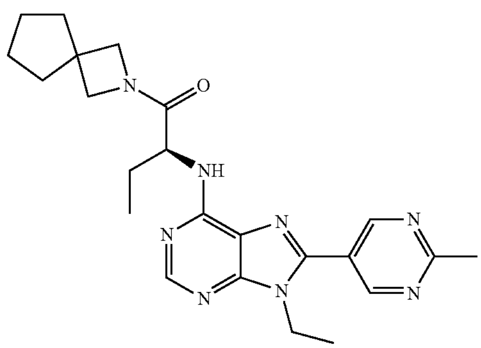 [SMILES: CC[C@H](Nc1ncnc2c1nc(-c1cnc(C)nc1)n2CC)C(=O)N1CC2(CCCC2)C1] | N-[(1S)-1-(2-azaspiro[3.4]oct-2-ylcarbonyl)propyl]-9-ethyl-8-(2-methylpyrimidin-5-yl)-9H-purin-6-amine | Calc'd 435; found 435 |
| 2-22 | 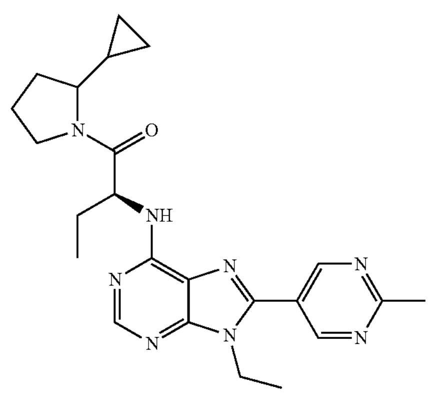 [SMILES: CC[C@H](Nc1ncnc2c1nc(-c1cnc(C)nc1)n2CC)C(=O)N1CCCC1C1CC1] | N-{(1S)-1-[((R and S)-2-cyclopropylpyrrolidin-1-yl)carbonyl]propyl}-9-ethyl-8-(2-methylpyrimidin-5-yl)-9H-purin-6-amine | Calc'd 435; found 435 |
| 2-23 | 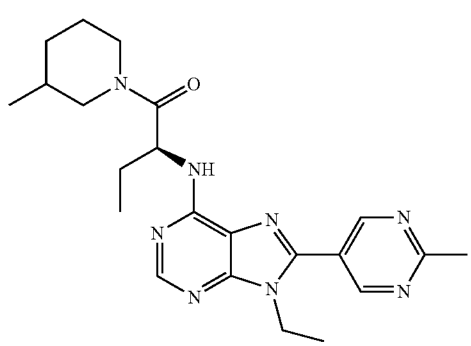 | 9-ethyl-N-{(1S)-1-[((R and S)-3-methylpiperidin-1-yl)carbonyl]propyl}-8-(2-methylpyrimidin-5-yl)-9H-purin-6-amine | Calc'd 423; found 423 |

TABLE 2-continued

| Compound | Structure | IUPAC Name | Exact Mass [M + H]+ |
|---|---|---|---|
| 2-24 | 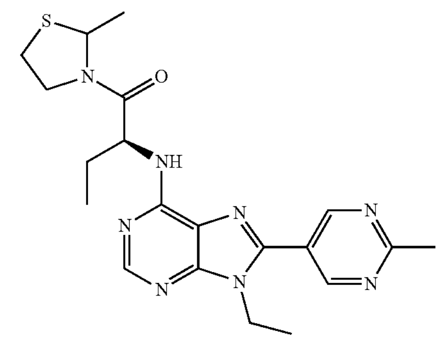 [SMILES: CC[C@H](Nc1ncnc2c1nc(-c1cnc(C)nc1)n2CC)C(=O)N1CCSC1C] | 9-ethyl-8-(2-methylpyrimidin-5-yl)-N-{(1S)-1-[((S and R)-2-methyl-1,3-thiazolidin-3-yl)carbonyl]propyl}-9H-purin-6-amine | Calc'd 427; found 427 |
| 2-25 | 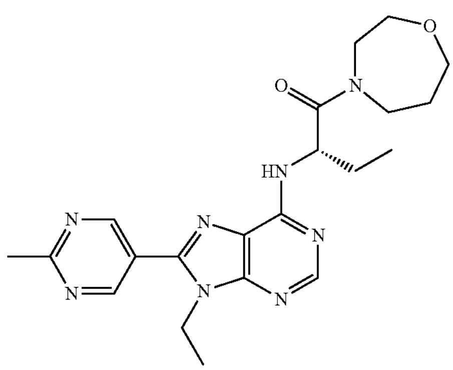 [SMILES: CC[C@H](Nc1ncnc2c1nc(-c1cnc(C)nc1)n2CC)C(=O)N1CCCOCC1] | 9-ethyl-8-(2-methylpyrimidin-5-yl)-N-[(1S)-1-(1,4-oxazepan-4-ylcarbonyl)propyl]-9H-purin-6-amine | Calc'd 425; found 425 |
| 2-26 | 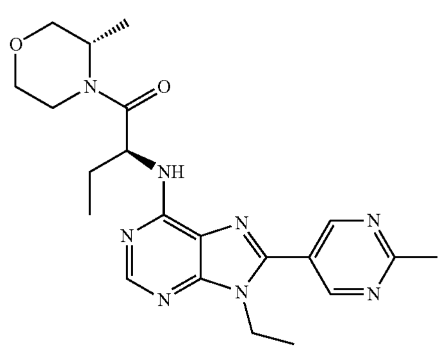 [SMILES: CC[C@H](Nc1ncnc2c1nc(-c1cnc(C)nc1)n2CC)C(=O)N1CCOC[C@@H]1C] | 9-ethyl-N-[(1S)-1-{[(3S)-3-methylmorpholin-4-yl]carbonyl}propyl]-8-(2-methylpyrimidin-5-yl)-9H-purin-6-amine | Calc'd 425; found 425 |
| 2-27 | 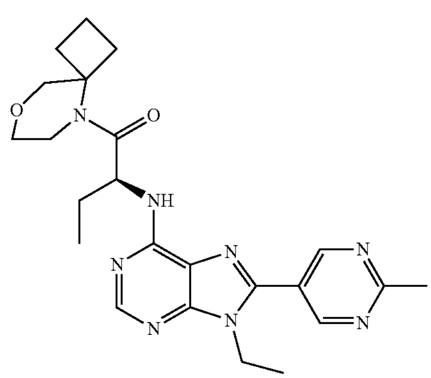 [SMILES: CC[C@H](Nc1ncnc2c1nc(-c1cnc(C)nc1)n2CC)C(=O)N1CCOCC12CCC2] | 9-ethyl-8-(2-methylpyrimidin-5-yl)-N-[(1S)-1-(8-oxa-5-azaspiro[3.5]non-5-ylcarbonyl)propyl]-9H-purin-6-amine | Calc'd 451; found 451 |

TABLE 2-continued

| Compound | Structure | IUPAC Name | Exact Mass [M + H]+ |
|---|---|---|---|
| 2-28 | 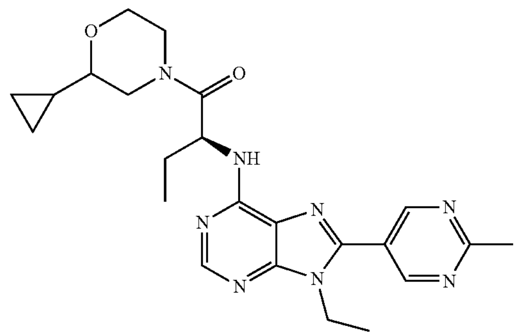 [SMILES: CC[C@H](Nc1ncnc2c1nc(-c1cnc(C)nc1)n2CC)C(=O)N1CCOC(C2CC2)C1] | N-{(1S)-1-[((S and R)-2-cyclopropylmorpholin-4-yl)carbonyl]propyl}-9-ethyl-8-(2-methylpyrimidin-5-yl)-9H-purin-6-amine | Calc'd 451; found 451 |
| 2-29 | 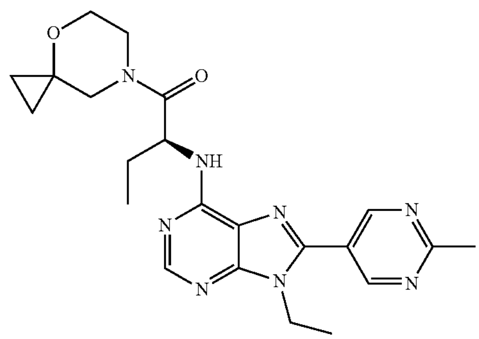 [SMILES: CC[C@H](Nc1ncnc2c1nc(-c1cnc(C)nc1)n2CC)C(=O)N1CCOC2(CC2)C1] | 9-ethyl-8-(2-methylpyrimidin-5-yl)-N-[(1S)-1-(4-oxa-7-azaspiro[2.5]oct-7-ylcarbonyl)propyl]-9H-purin-6-amine | Calc'd 437; found 437 |
| 2-30 | 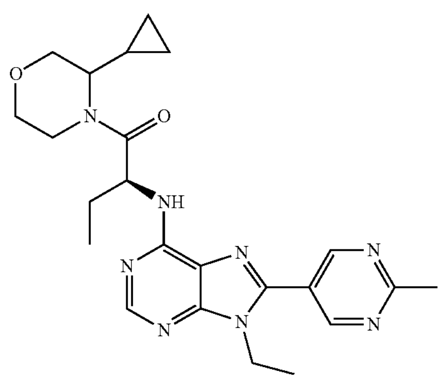 [SMILES: CC[C@H](Nc1ncnc2c1nc(-c1cnc(C)nc1)n2CC)C(=O)N1CCOCC1C1CC1] | N-{(1S)-1-[((S and R)-3-cyclopropylmorpholin-4-yl)carbonyl]propyl}-9-ethyl-8-(2-methylpyrimidin-5-yl)-9H-purin-6-amine | Calc'd 451; found 451 |
| 2-31 | 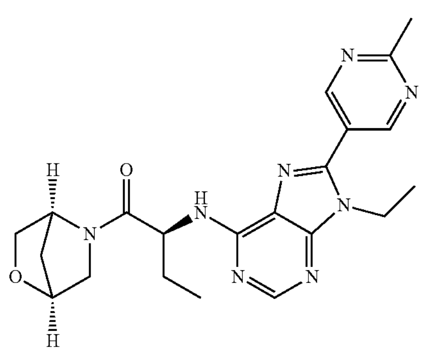 [SMILES: CC[C@H](Nc1ncnc2c1nc(-c1cnc(C)nc1)n2CC)C(=O)N1C[C@@H]2C[C@H]1CO2] | 9-ethyl-8-(2-methylpyrimidin-5-yl)-N-{(1S)-1-[(1S,4S)-2-oxa-5-azabicyclo[2.2.1]hept-5-ylcarbonyl]propyl}-9H-purin-6-amine | Calc'd 423; found 423 |

TABLE 2-continued

| Compound | Structure | IUPAC Name | Exact Mass [M + H]+ |
|---|---|---|---|
| 2-32 | 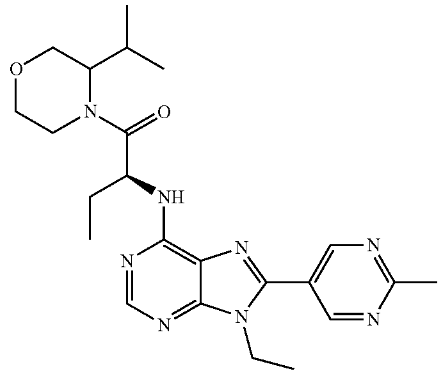 [SMILES: CC[C@H](Nc1ncnc2c1nc(-c1cnc(C)nc1)n2CC)C(=O)N1CCOCC1C(C)C] | 9-ethyl-N-[(1S)-1-{[3-(1-methylethyl)morpholin-4-yl]carbonyl}propyl]-8-(2-methylpyrimidin-5-yl)-9H-purin-6-amine | Calc'd 453; found 453 |
| 2-33 | 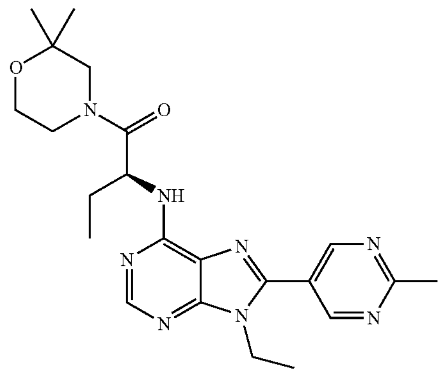 [SMILES: CC[C@H](Nc1ncnc2c1nc(-c1cnc(C)nc1)n2CC)C(=O)N1CCOC(C)(C)C1] | N-{(1S)-1-[(2,2-dimethylmorpholin-4-yl)carbonyl]propyl}-9-ethyl-8-(2-methylpyrimidin-5-yl)-9H-purin-6-amine | Calc'd 439; found 439 |
| 2-34 | 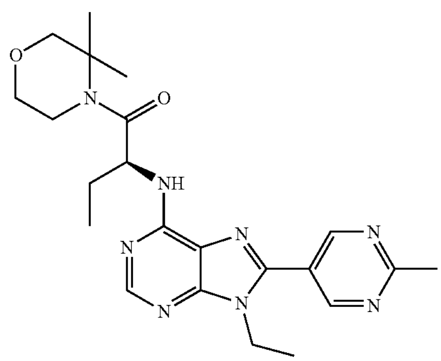 [SMILES: CC[C@H](Nc1ncnc2c1nc(-c1cnc(C)nc1)n2CC)C(=O)N1CCOCC1(C)C] | N-{(1S)-1-[(3,3-dimethylmorpholin-4-yl)carbonyl]propyl}-9-ethyl-8-(2-methylpyrimidin-5-yl)-9H-purin-6-amine | Calc'd 439; found 439 |
| 2-35 | 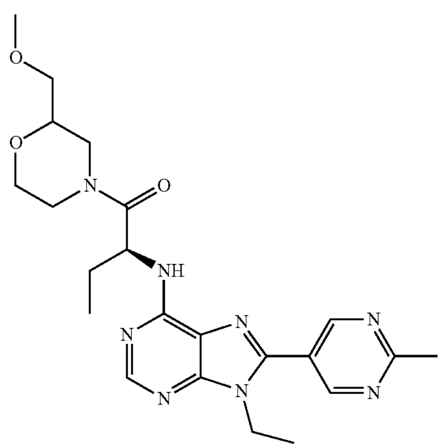 [SMILES: CC[C@H](Nc1ncnc2c1nc(-c1cnc(C)nc1)n2CC)C(=O)N1CCOC(COC)C1] | 9-ethyl-N-[(1S)-1-{[2-(methoxymethyl)morpholin-4-yl]carbonyl}propyl]-8-(2-methylpyrimidin-5-yl)-9H-purin-6-amine | Calc'd 455; found 455 |

TABLE 2-continued

| Compound | Structure | IUPAC Name | Exact Mass [M + H]+ |
|---|---|---|---|
| 2-36 | 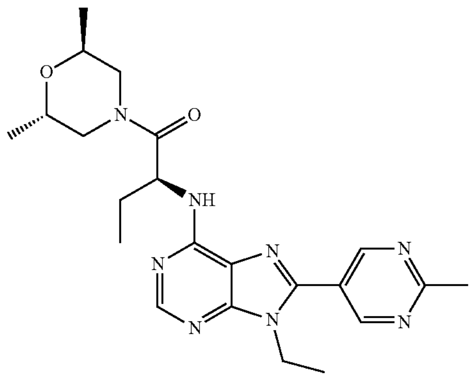 | N-[(1S)-1-{[(trans)-2,6-dimethylmorpholin-4-yl]carbonyl}propyl]-9-ethyl-8-(2-methylpyrimidin-5-yl)-9H-purin-6-amine | Calc'd 439; found 439 |
| 2-37 | 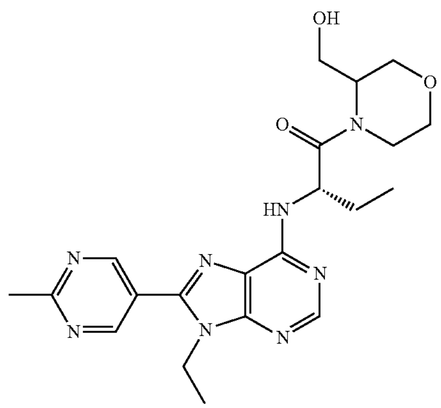 [SMILES: CC[C@H](Nc1ncnc2c1nc(-c1cnc(C)nc1)n2CC)C(=O)N1CCOCC1CO] | {4-[(2S)-2-{[9-ethyl-8-(2-methylpyrimidin-5-yl)-9H-purin-6-yl]amino}butanoyl]-(R and S)-morpholin-3-yl}methanol | Calc'd 441; found 441 |
| 2-38 | 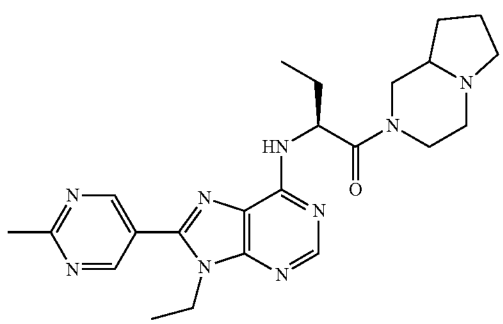 [SMILES: CC[C@H](Nc1ncnc2c1nc(-c1cnc(C)nc1)n2CC)C(=O)N1CCN2CCCC2C1] | 9-ethyl-N-[(1S)-1-(S and R)-(hexahydropyrrolo[1,2-a]pyrazin-2(1H)-ylcarbonyl)propyl]-8-(2-methylpyrimidin-5-yl)-9H-purin-6-amine | Calc'd 450; found 450 |
| 2-39 | 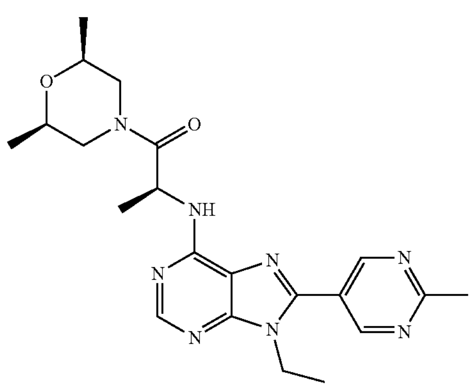 | N-{(1S)-2-[(cis)-2,6-dimethylmorpholin-4-yl]-1-methyl-2-oxoethyl}-9-ethyl-8-(2-methylpyrimidin-5-yl)-9H-purin-6-amine | Calc'd 425; found 425 |

TABLE 2-continued

| Compound | Structure | IUPAC Name | Exact Mass [M + H]+ |
|---|---|---|---|
| 2-40 | 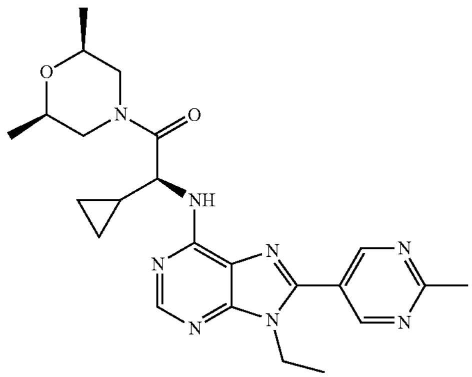 | N-{(1S)-1-cyclopropyl-2-[(cis)-2,6-dimethylmorpholin-4-yl]-2-oxoethyl}-9-ethyl-8-(2-methylpyrimidin-5-yl)-9H-purin-6-amine | Calc'd 451; found 451 |
| 2-41 | 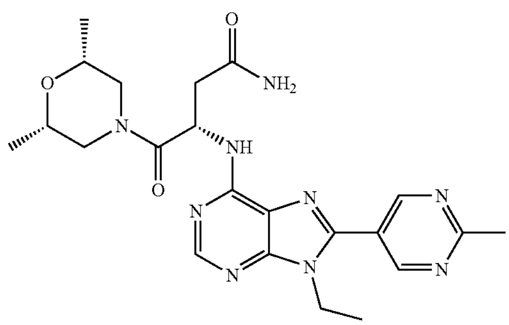 | (3S)-4-[(cis)-2,6-dimethylmorpholin-4-yl]-3-{[9-ethyl-8-(2-methylpyrimidin-5-yl)-9H-purin-6-yl]amino}-4-oxobutanamide | Calc'd 468; found 468 |
| 2-42 | 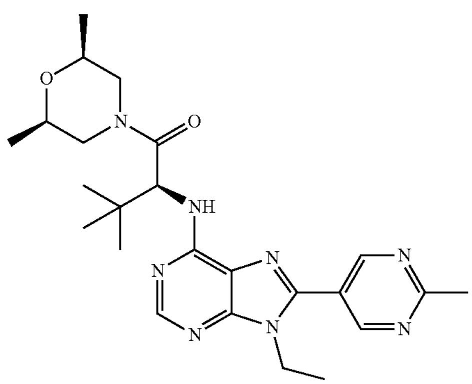 | N-[(1S)-1-{[(cis)-2,6-dimethylmorpholin-4-yl]carbonyl}-2,2-dimethylpropyl]-9-ethyl-8-(2-methylpyrimidin-5-yl)-9H-purin-6-amine | Calc'd 467; found 467 |
| 2-43 | 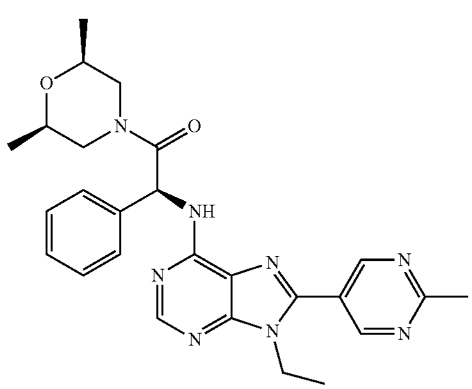 | N-{(1S)-2-[(cis)-2,6-dimethylmorpholin-4-yl]-2-oxo-1-phenylethyl}-9-ethyl-8-(2-methylpyrimidin-5-yl)-9H-purin-6-amine | Calc'd 487; found 487 |

TABLE 2-continued

| Compound | Structure | IUPAC Name | Exact Mass [M + H]+ |
|---|---|---|---|
| 2-44 | 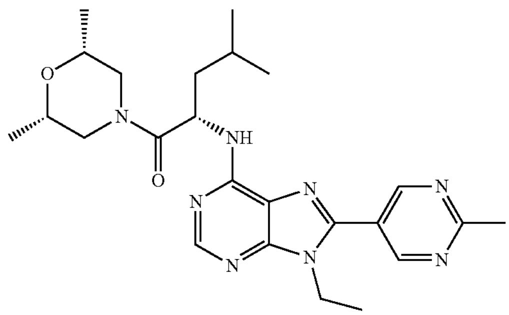 | N-[(1S)-1-{[(cis)-2,6-dimethylmorpholin-4-yl]carbonyl}-3-methylbutyl]-9-ethyl-8-(2-methylpyrimidin-5-yl)-9H-purin-6-amine | Calc'd 467; found 467 |
| 2-45 | 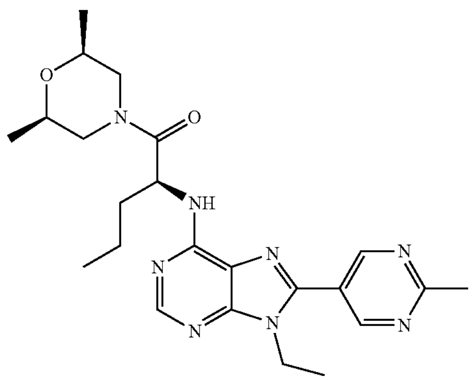 | N-[(1S)-1-{[(cis)-2,6-dimethylmorpholin-4-yl]carbonyl}butyl]-9-ethyl-8-(2-methylpyrimidin-5-yl)-9H-purin-6-amine | Calc'd 453; found 453 |
| 2-46 | 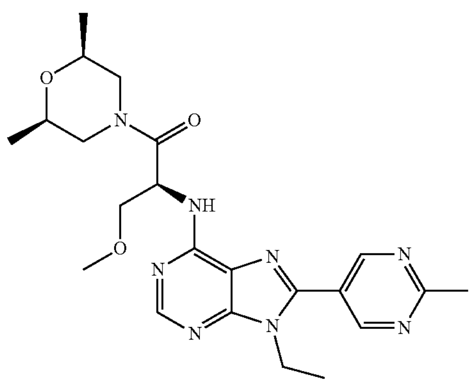 | N-[(1S)-2-[(cis)-2,6-dimethylmorpholin-4-yl]-1-(methoxymethyl)-2-oxoethyl]-9-ethyl-8-(2-methylpyrimidin-5-yl)-9H-purin-6-amine | Calc'd 455; found 455 |
| 2-47 | 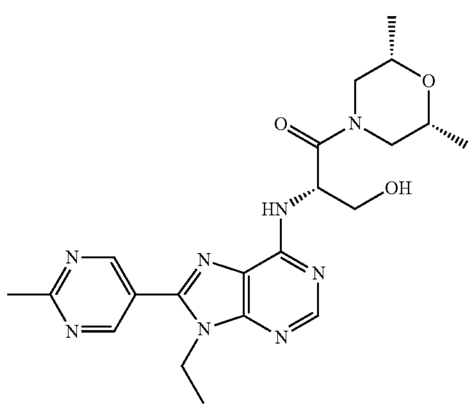 | (2S)-3-[(cis)-2,6-dimethylmorpholin-4-yl]-2-{[9-ethyl-8-(2-methylpyrimidin-5-yl)-9H-purin-6-yl]amino}-3-oxopropan-1-ol | Calc'd 441; found 441 |

TABLE 2-continued

| Compound | Structure | IUPAC Name | Exact Mass [M + H]+ |
|---|---|---|---|
| 2-48 | 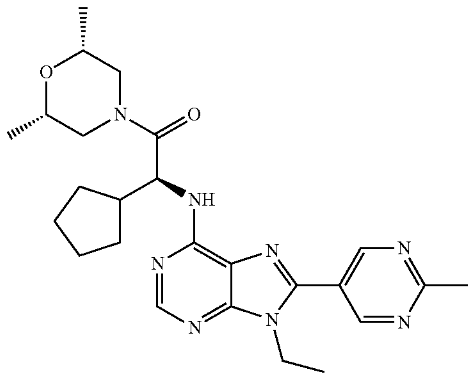 | N-{(1S)-1-cyclopentyl-2-[(cis)-2,6-dimethylmorpholin-4-yl]-2-oxoethyl}-9-ethyl-8-(2-methylpyrimidin-5-yl)-9H-purin-6-amine | Calc'd 479; found 479 |
| 2-49 | 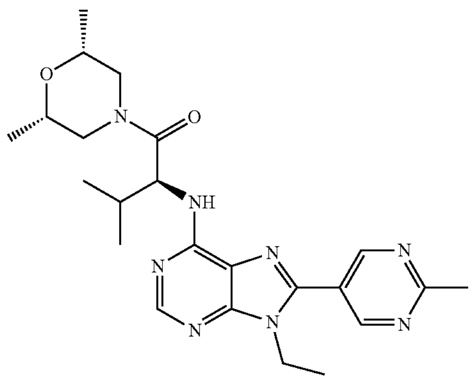 | N-[(1S)-1-{[(cis)-2,6-dimethylmorpholin-4-yl]carbonyl}-2-methylpropyl]-9-ethyl-8-(2-methylpyrimidin-5-yl)-9H-purin-6-amine | Calc'd 453; found 453 |
| 2-50 | 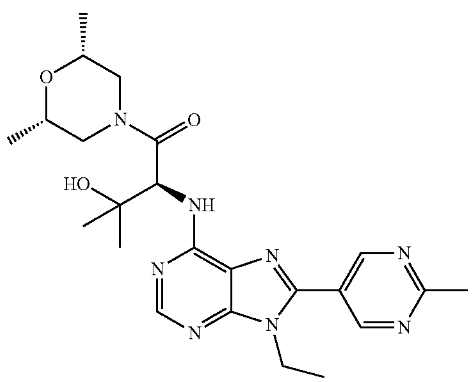 | (3S)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol | Calc'd 469; found 469 |
| 2-51 | 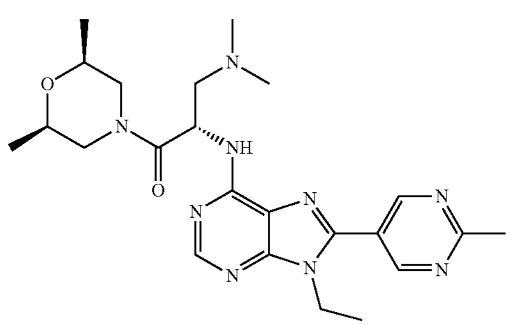 | (2S)-3-[(cis)-2,6-dimethylmorpholin-4-yl]-N-2-[9-ethyl-8-(2-methylpyrimidin-5-yl)-9H-purin-6-yl]-N-1-,N-1-dimethyl-3-oxopropane-1,2-diamine | Calc'd 468; found 468 |

TABLE 2-continued

| Compound | Structure | IUPAC Name | Exact Mass [M + H]+ |
|---|---|---|---|
| 2-52 | 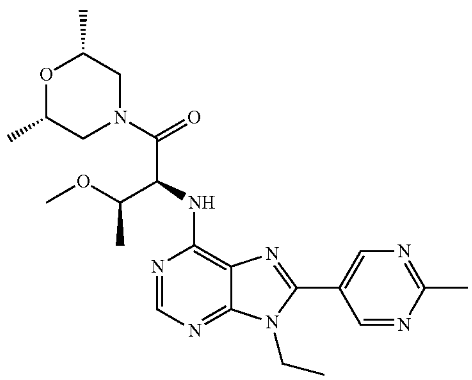 | N-[(1S,2R)-1-{[(cis)-2,6-dimethylmorpholin-4-yl]carbonyl}-2-methoxypropyl]-9-ethyl-8-(2-methylpyrimidin-5-yl)-9H-purin-6-amine | Calc'd 469; found 469 |
| 2-53 | 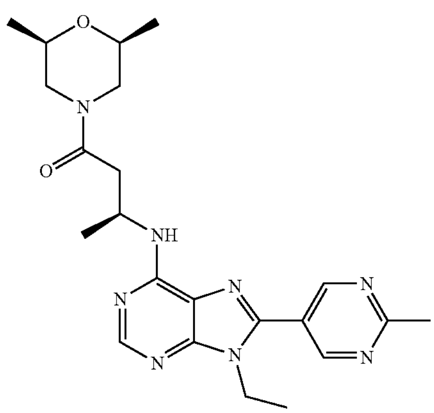 | N-{(1S)-3-[(cis)-2,6-dimethylmorpholin-4-yl]-1-methyl-3-oxopropyl}-9-ethyl-8-(2-methylpyrimidin-5-yl)-9H-purin-6-amine | Calc'd 439; found 439 |
| 2-54 | 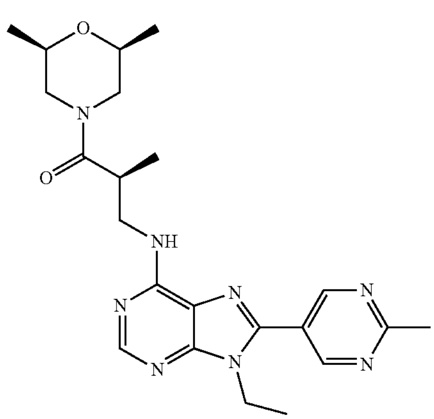 | N-{(2S)-3-[(cis)-2,6-dimethylmorpholin-4-yl]-2-methyl-3-oxopropyl}-9-ethyl-8-(2-methylpyrimidin-5-yl)-9H-purin-6-amine | Calc'd 439; found 439 |

TABLE 2-continued

| Compound | Structure | IUPAC Name | Exact Mass [M + H]+ |
|---|---|---|---|
| 2-55 | 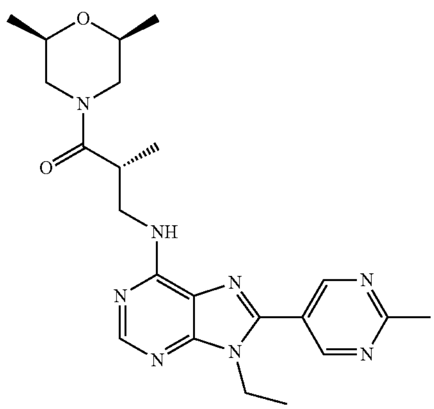 | N-{(2R)-3-[(cis)-2,6-dimethylmorpholin-4-yl]-2-methyl-3-oxopropyl}-9-ethyl-8-(2-methylpyrimidin-5-yl)-9H-purin-6-amine | Calc'd 439; found 439 |
| 2-56 | 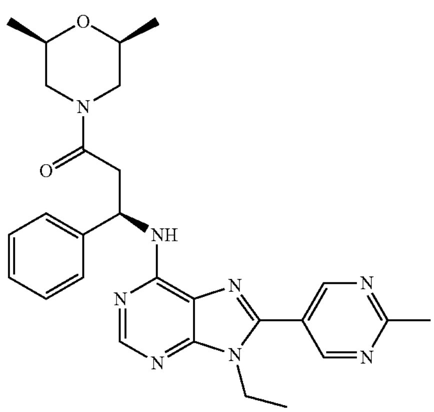 | N-{(1R)-3-[(cis)-2,6-dimethylmorpholin-4-yl]-3-oxo-1-phenylpropyl}-9-ethyl-8-(2-methylpyrimidin-5-yl)-9H-purin-6-amine | Calc'd 501; found 501 |
| 2-57 | 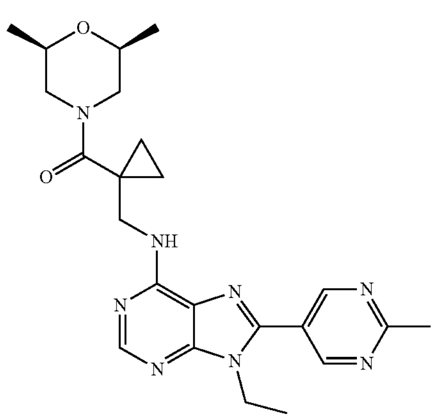 | N-[(1-{[(cis)-2,6-dimethylmorpholin-4-yl]carbonyl}cyclopropyl)methyl]-9-ethyl-8-(2-methylpyrimidin-5-yl)-9H-purin-6-amine | Calc'd 451; found 451 |

TABLE 2-continued

| Compound | Structure | IUPAC Name | Exact Mass [M + H]+ |
|---|---|---|---|
| 2-58 | 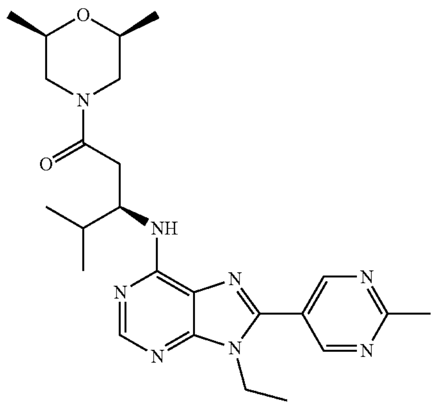 | N-[(1R)-3-[(cis)-2,6-dimethylmorpholin-4-yl]-1-(1-methylethyl)-3-oxopropyl]-9-ethyl-8-(2-methylpyrimidin-5-yl)-9H-purin-6-amine | Calc'd 467; found 467 |
| 2-59 | 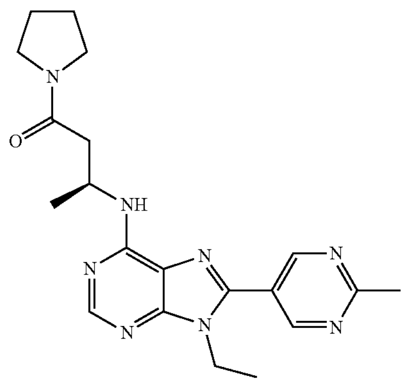 [SMILES: CCn1c(-c2cnc(C)nc2)nc2c(N[C@@H](C)CC(=O)N3CCCC3)ncnc21] | 9-ethyl-N-[(1S)-1-methyl-3-oxo-3-pyrrolidin-1-ylpropyl]-8-(2-methylpyrimidin-5-yl)-9H-purin-6-amine | Calc'd 395; found 395 |
| 2-60 | 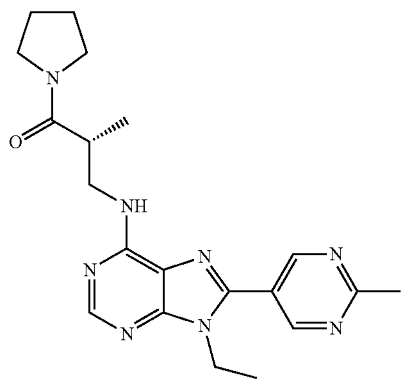 [SMILES: CCn1c(-c2cnc(C)nc2)nc2c(NC[C@@H](C)C(=O)N3CCCC3)ncnc21] | 9-ethyl-N-[(2R)-2-methyl-3-oxo-3-pyrrolidin-1-ylpropyl]-8-(2-methylpyrimidin-5-yl)-9H-purin-6-amine | Calc'd 395; found 395 |
| 2-61 | 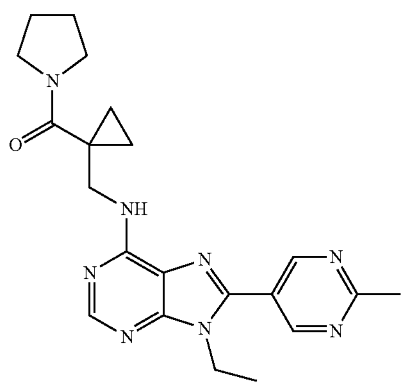 [SMILES: CCn1c(-c2cnc(C)nc2)nc2c(NCC3(C(=O)N4CCCC4)CC3)ncnc21] | 9-ethyl-8-(2-methylpyrimidin-5-yl)-N-{[1-(pyrrolidin-1-ylcarbonyl)cyclopropyl]methyl}-9H-purin-6-amine | Calc'd 407; found 407 |

TABLE 2-continued

| Compound | Structure | IUPAC Name | Exact Mass [M + H]+ |
|---|---|---|---|
| 2-62 | 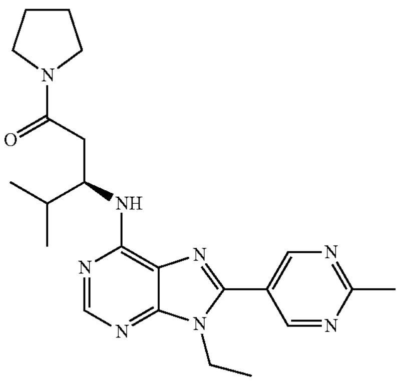 [SMILES: CCn1c(-c2cnc(C)nc2)nc2c(N[C@H](CC(=O)N3CCCC3)C(C)C)ncnc21] | 9-ethyl-N-[(1R)-1-(1-methylethyl)-3-oxo-3-pyrrolidin-1-ylpropyl]-8-(2-methylpyrimidin-5-yl)-9H-purin-6-amine | Calc'd 423; found 423 |

Compound Examples of Table 3

Example III-9 Preparation of Compound 3-1

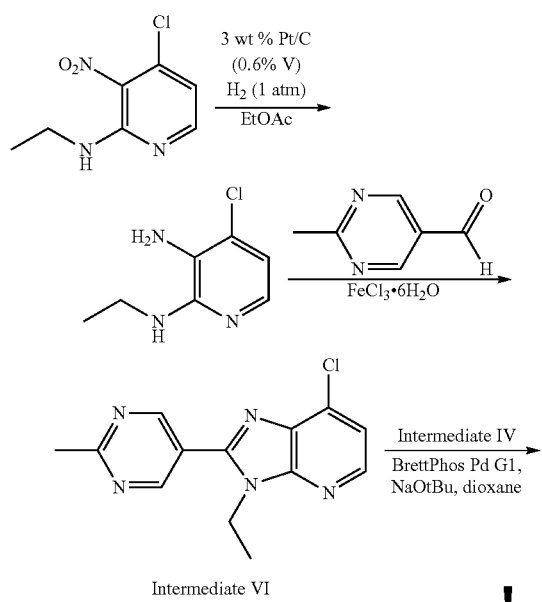

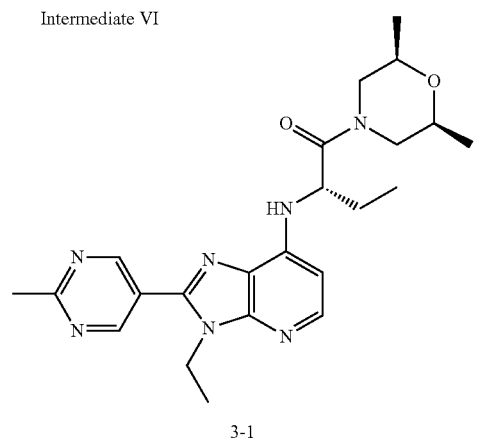

3-1

Step 1 4-Chloro-N2-ethylpyridine-2,3-diamine

4-Chloro-N-ethyl-3-nitropyridin-2-amine (1.00 g, 4.96 mmol, commercially available from HDH Pharma Building Blocks) was dissolved in EtOAc (50 ml) under an atmosphere of argon and platinum on carbon (3% by weight), doped with vanadium (0.6% by weight) (0.103 g, 0.496 mmol) was added. The flask was then purged with hydrogen gas (×3) and the reaction was allowed to stir under a hydrogen atmosphere (1 atm) at RT for 68 h. The reaction mixture was then filtered over Celite (a trademarked version of diatomaceous earth) eluting with MeOH and DCM. The mixture was then concentrated in vacuo to give 4-chloro-N2-ethylpyridine-2,3-diamine which was used in the next step without further purification. MS ESI calc'd. for $C_7H_{11}ClN_3$ [M+1]$^+$ 172; found 172.

Step 2 7-Chloro-3-ethyl-2-(2-methylpyrimidin-5-yl)-3H-imidazo[4,5-b]pyridine (Intermediate VI)

4-chloro-N2-methylpyridine-2,3-diamine (840 mg, 5.33 mmol) and iron (III) chloride hexahydrate (360 mg, 1.33 mmol) were dissolved in DMF (26 ml). 2-Methylpyrimidine-5-carbaldehyde (716 mg, 5.86 mmol) was then added and the reaction was allowed to stir vigorously at 80° C. open to air for 18 h. The reaction mixture was then diluted with 3:1 chloroform:IPA and washed with water. The combined organic layers were washed with brine, dried over MgSO$_4$, and concentrated in vacuo while loading onto silica gel. Purification by column chromatography (silica gel, eluting with a gradient of 0-60% 3:1 EtOAc:EtOH in hexanes) gave 7-chloro-3-ethyl-2-(2-methylpyrimidin-5-yl)-3H-imidazo[4,5-b]pyridine (Intermediate IV). MS ESI calc'd. for $C_{13}H_{13}ClN_5$ [M+1]+274; found 274.

Step 3 Compound 3-1

Intermediate IV (130 mg, 0.48 mmol), chloro[2-(dicyclohexylphosphino)-3,6-dimethoxy-2',4',6'-triisopropyl-1,1'-biphenyl][2-(2-aminoethyl)phenyl]palladium(II) (BrettPhos Pd G1) (37.9 mg, 0.047 mmol), Intermediate IV (95 mg, 0.40 mmol) and sodium tert-butoxide (137 mg, 1.43 mmol) were taken up in dry 1,4-dioxane (5.0 ml) and heated at 50° C. overnight. The mixture was filtered through Celite (a trademarked version of diatomaceous earth) and concentrated in vacuo while loading onto silica gel. Purification by column chromatography (silica gel, eluting with a gradient of 50-100% 3:1 EtOAc:EtOH in hexanes with 2% $NH_4$ added) gave the desired product; however, small satellite peaks were still present by NMR analysis. The product was then taken up in DMF (2.0 ml) and was purified by reverse phase mass triggered preparative HPLC (eluting with a gradient of 0-100% MeCN in water with 0.1% TFA modifier). The product-containing fractions were combined and taken up in 3:1 chloroform:IPA and washed with saturated aqueous $NaHCO_3$. The combined organic layers were washed with brine, dried over $MgSO_4$, and concentrated in vacuo to give compound 3-1. $^1H$ NMR (500 MHz, DMSO-d6) δ 9.12 (s, 2H), 7.94 (br s, 1H), 6.51 (t, J=5.5, 1H), 4.32 (t, J=8, 2H), 4.24-4.22 (m, 1H), 4.11-4.06 (m, 1H), 3.51-3.49 (m, 1H), 3.42-3.40 (m, 1H), 3.74 (s, 3H), 2.29-2.25 (m, 1H), 1.79-1.77 (m, 1H), 1.70-1.64 (m, 1H), 1.32-1.29 (m, 6H), 1.08-0.93 (m, 6H). MS ESI calc'd. for $C_{23}H_{32}N_7O_2$ $[M+1]^+$ 438; found 438.

Example III-2 Preparation of Compound 3-2

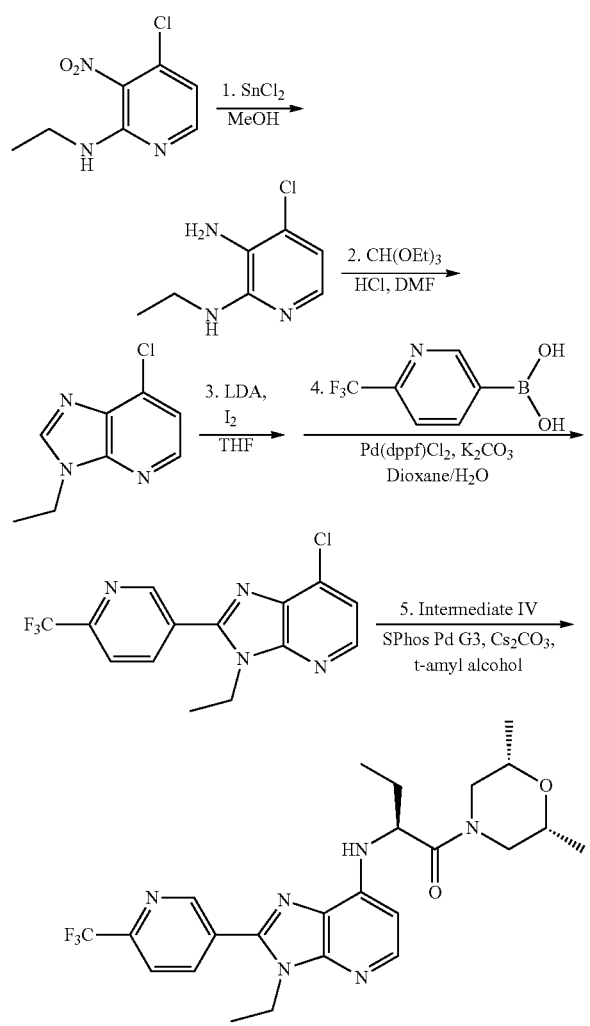

Step 1 4-Chloro-$N^2$-ethylpyridine-2,3-diamine

To a solution of 4-chloro-N-ethyl-3-nitropyridin-2-amine (0.80 g, 4.0 mmol) in MeOH (20 mL) was added tin(II) chloride dihydrate (0.90 g, 4.0 mmol) at RT. The resulting mixture was then heated to 50° C. where it was stirred for 2 h. After cooling to RT, the reaction mixture was concentrated under reduced pressure. The residue was then diluted with aqueous sodium carbonate (50 mL, 3M), and the solids were removed via filtration. The filtrate was then extracted with EtOAc (3×50 mL), and the combined organic layers were washed with brine, dried over anhydrous $Na_2SO_4$, and filtered. The filtrate was concentrated under reduced pressure, and the residue thus obtained was purified by column chromatography (silica gel, eluting with a 0-40% gradient of EtOAc in Hexanes) to afford 4-chloro-$N^2$-ethylpyridine-2,3-diamine. MS (ESI) Calc'd for $(C_7H_{11}ClN_3)$ $[M+H]^+$ 172 found 172.

Step 2 7-Chloro-3-ethyl-3H-imidazo[4,5-b]pyridine

To a solution of 4-chloro-$N^2$-ethylpyridine-2,3-diamine (0.50 g, 2.9 mmol) in DMF (10 mL) at RT were added triethoxymethane (0.86 g, 5.8 mmol) and aqueous HCl (37% by weight, 1 drop), after which the resulting mixture was stirred for 12 h. The reaction mixture was then quenched with water (20 mL), and extracted with EtOAc (3×50 mL). The combined organic layers were washed with brine (50 mL), dried over anhydrous $Na_2SO_4$, and filtered. The filtrate was concentrated under reduced pressure, and the residue thus obtained was purified by column chromatography (silica gel, eluting with a gradient of 0-80% EtOAc in hexanes) to afford 7-chloro-3-ethyl-3H-imidazo[4,5-b]pyridine. MS (ESI) Calc'd for $(C_8H_9ClN_3)$ $[M+H]^+$ 182; found 182.

Step 3 7-Chloro-3-ethyl-2-iodo-3H-imidazo[4,5-b]pyridine

To a solution of diisopropylamine (0.33 g, 3.2 mmol) in THF (20 mL) was added n-butyllithium (1.29 mL, 2.5 mol/L in Hexane, 3.22 mmol) dropwise at −78° C. under an atmosphere of nitrogen. The resulting solution was stirred at −78° C. for 30 min, after which 7-chloro-3-ethyl-3H-imidazo[4,5-b]pyridine (0.45 g, 2.48 mmol) was added drop-wise as a solution in THF (20 mL). The resulting solution was further stirred for 30 min at −78° C., after which iodine (0.82 g, 3.22 mmol) was added drop-wise as a solution in THF (20 mL). The resulting solution was further stirred for 30 min at −78° C., after which it was allowed to warm to RT. The reaction mixture was then quenched by the addition of saturated aqueous $NH_4Cl$ (50 mL), and the resulting mixture was extracted with EtOAc (3×50 mL). The combined organic layers were washed with brine (50 mL), dried over anhydrous $Na_2SO_4$, and filtered. The filtrate was concentrated under reduced pressure, and the residue thus obtained was purified by column chromatography (silica gel, eluting with a gradient of 0-100% EtOAc in Hexanes) to afford 7-chloro-3-ethyl-2-iodo-3H-imidazo[4,5-b]pyridine. MS (ESI) Calc'd for $(C_8H_8ClIN_3)$ $[M+H]^+$ 308; found 308.

Step 4 7-Chloro-3-ethyl-2-(6-(trifluoromethyl)pyridin-3-yl)-3H-imidazo[4,5-b]pyridine To a solution of 7-chloro-3-ethyl-2-iodo-3H-imidazo[4,5-b]pyridine (100 mg, 0.33 mmol) in a mixture of dioxane (3 mL) and $H_2O$ (0.6 mL) were added (6-(trifluoromethyl)

pyridine-3-yl)boronic acid (68.3 mg, 0.36 mmol), K₂CO₃ (135 mg, 0.98 mmol) and Pd(dppf)Cl₂ (24 mg, 0.03 mmol) at RT. The resulting mixture was degassed with nitrogen and stirred for 3 h at 90° C. After cooling to RT, the reaction mixture was quenched with water (10 mL). The resulting mixture was extracted with EtOAc (3×10 mL). The combined organic layers was washed with brine (10 mL), dried over anhydrous Na₂SO₄ and filtered. The filtrate was concentrated under reduced pressure, and the residue obtained was purified by column chromatography (silica gel, eluting with a gradient of 0-100% EtOAc in Hexanes) to afford 7-chloro-3-ethyl-2-(6-(trifluoromethyl)pyridin-3-yl)-3H-imidazo[4,5-b]. MS (ESI) Calc'd for (C14H11ClF3N₄) [M+H]⁺, 327; found 327.

Step 5 Compound 3-2

To a solution of 7-chloro-3-ethyl-2-(6-(trifluoromethyl) pyridin-3-yl)-3H-imidazo[4,5-b]pyridine (50 mg, 0.15 mmol)) in t-amyl alcohol (2 mL) at RT were added Intermediate IV (as the free base) (46 mg, 0.23 mmol), cesium carbonate (100 mg, 0.31 mmol), and (2-dicyclohexylphosphino-2',6'-dimethoxybiphenyl) [2-(2'-amino-1,1'-biphenyl)]palladium(II) methanesulfonate (SPhos Pd G3) (12 mg, 0.02 mmol). The resulting mixture was stirred for 20 h at 100° C. under atmosphere of nitrogen. The reaction mixture was then cooled to RT and water (10 mL) was added, after which the mixture was extracted with EtOAc (3×8 mL). The combined organic layers were washed with brine (10 mL), dried over anhydrous Na₂SO₄, and filtered. The filtrate was concentrated under reduced pressure, and the residue thus obtained was purified by column chromatography (silica gel, eluting with a gradient of 0-100% EtOAc in hexanes) to afford compound 3-2. ¹H NMR (300 MHz, CD₃OD) δ: 9.15 (s, 1H), 8.42 (d, J=8.1 Hz, 1H), 8.03-7.97 (m, 2H), 6.56-6.49 (m, 1H), 5.40-5.05 (m, 1H), 4.40 (q, J=7.2 Hz, 2H), 4.36-4.28 (m, 1H), 4.08-4.04 (m, 1H), 3.51-3.40 (m, 2H), 2.86-2.81 (m, 1H), 2.38-2.30 (m, 1H), 1.92-1.75 (m, 2H), 1.38 (t, J=7.2 Hz, 3H), 1.17-1.00 (m, 9H). MS (ESI) Calc'd for (C₂₄H₃₀F₃N₆O₂) [M+H]⁺, 491; found 491.

Example III-3 Preparation of Compound 3-3

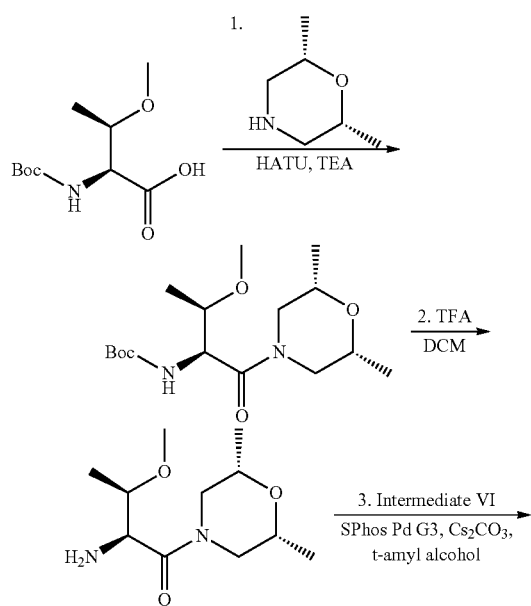

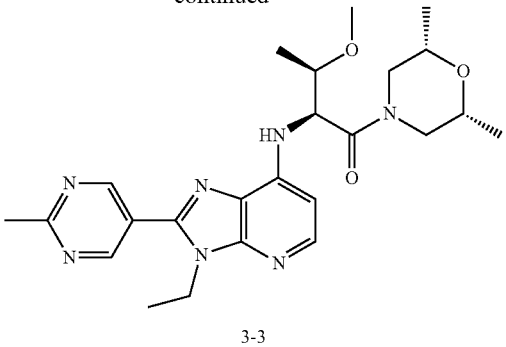

3-3

Step 1 tert-Butyl-((2S,3R)-1-((cis)-2,6-dimethylmorpholino)-3-methoxy-1-oxobutan-2-yl)carbamate To a solution of (2S,3R)-2-((tert-butoxycarbonyl) amino)-3-methoxybutanoic acid (0.50 g, 2.1 mmol, commercially available from Matrix Scientific) in DCM (10 mL) at RT were added TEA (0.30 mL, 2.1 mmol), HATU (815 mg, 2.14 mmol), and cis-2,6-dimethylmorpholine (247 mg, 2.14 mmol). The resulting mixture was stirred for 1 h under an atmosphere of N₂. The reaction mixture was then quenched with water (20 mL). The resulting mixture was extracted with DCM (3×50 mL), and the combined organic layers were washed with brine (50 mL), dried over anhydrous Na₂SO₄, and filtered. The filtrate was concentrated under reduced pressure, and the residue thus obtained was purified by column chromatography (silica gel, eluting with a gradient of 0-50% EtOAc in hexanes) to provide tert-butyl ((2S,3R)-1-((2R,6S)-2,6-dimethylmorpholino)-3-methoxy-1-oxobutan-2-yl)carbamate. MS (ESI) Calc'd for (C₁₆H₃₁N₂O₅) [M+H]⁺ 331; found 331.

Step 2 (2S,3R)-2-Amino-1-((cis)-2,6-dimethylmorpholino)-3-methoxybutan-1-one

To a solution of tert-butyl-((2S,3R)-1-((2R,6S)-2,6-dimethylmorpholino)-3-methoxy-1-oxobutan-2-yl)carbamate (0.65 g, 2.0 mmol) in DCM (5 mL) at RT was added TFA (2.5 mL). The reaction solution was stirred for 1 h at RT, after which the solution was concentrated under reduced pressure. The residue was then diluted in DCM (10 mL), and the residue thus obtained was purified by column chromatography (silica gel, eluting with a gradient of 0-30% MeOH (with 1% TEA added) in DCM) to afford (2S,3R)-2-amino-1-((2R,6S)-2,6-dimethylmorpholino)-3-methoxybutan-1-one. MS (ESI) Calc'd for (C₁₁H₂₃N₂O₃) [M+H]⁺ 231; found 231.

Step 3 Compound 3-3

To a solution of Intermediate VI (119 mg, 0.43 mmol) in tert-amyl alcohol (2 mL) at RT were added (2S,3R)-2-amino-1-(cis-2,6-dimethylmorpholino)-3-methoxybutan-1-one (100 mg, 0.43 mmol), cesium carbonate (280 mg, 0.87 mmol), and (2-dicyclohexylphosphino-2',6'-dimethoxybiphenyl) [2-(2'-amino-1,1'-biphenyl)]palladium(II) methanesulfonate (SPhos Pd G3) (34 mg, 0.043 mmol). The resulting mixture was stirred for 20 h at 100° C. under atmosphere of nitrogen. The reaction mixture was then cooled to RT and water (10 mL) was added, after which the mixture was extracted with EtOAc (3×8 mL). The combined organic layers were washed with brine (10 mL), dried over anhydrous Na₂SO₄, and filtered. The filtrate was concentrated under reduced pressure, and the residue obtained was purified by column chromatography (silica gel, eluting with a gradient of 0-100% EtOAc in hexanes) to afford compound 3-3. ¹H NMR (300 MHz, CD₃OD) δ: 9.08 (s, 2H), 7.98-7.95 (m, 1H), 6.57-6.52 (m, 1H), 5.35-5.20 (m, 1H), 4.37 (q, J=7.2 Hz, 2H), 4.30-4.10 (m, 2H), 3.79-3.77 (m, 1H), 3.61-3.45 (m, 5H), 2.88-2.78 (m, 1H), 2.76 (s, 3H), 2.42-2.25 (m, 1H), 1.40 (t, J=7.2 Hz, 3H), 1.30-1.00 (m, 9H). MS (ESI) Calc'd for (C₂₄H₃₄N₇O₃) [M+H]⁺ 468; found 468.

Compound 3-4 was prepared in an analogous fashion to Example III-3, except that 2-((tert-butoxycarbonyl)amino)-2-cyclopropylacetic acid was used in place of (2S,3R)-2-((tert-butoxycarbonyl) amino)-3-methoxybutanoic acid. Chiral resolution of the final compound was achieved via Prep-Chiral HPLC (Column: Chiralpak IA 2×25 cm, 5 um; Mobile Phase A: Hex-HPLC, Mobile Phase B: IPA-HPLC; Flow rate: 15 mL/min; Gradient: 40 B isocratic over 15 min) to afford compound 3-4 (faster-eluting enantiomer, 8 min).

TABLE 3

| Compound | Structure | IUPAC Name | Exact Mass [M + H]+ |
|---|---|---|---|
| 3-1 | 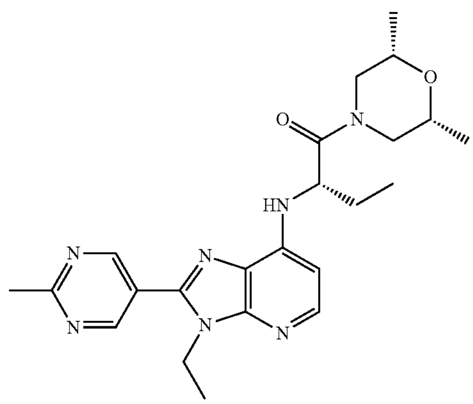 | N-[(1S)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine | Calc'd 438; found 438 |
| 3-2 | 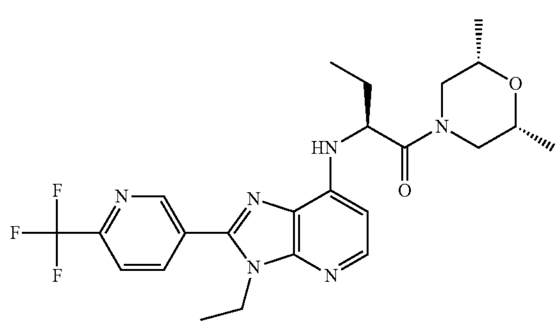 [SMILES: CC[C@H](Nc1ccnc2c1nc(-c1ccc(C(F)(F)F)nc1)n2CC)C(=O)N1C[C@@H](C)O[C@@H](C)C1] | N-[(1S)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine | Calc'd 491; found 491 |
| 3-3 | 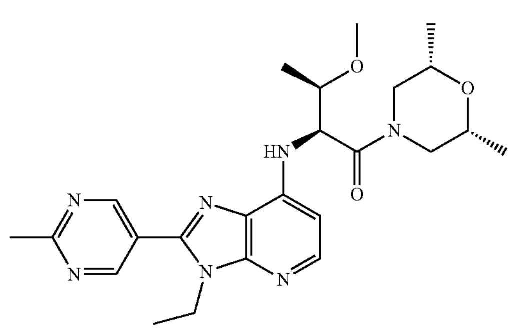 | N-[(1S,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine | Calc'd 468; found 468 |

TABLE 3-continued

| Compound | Structure | IUPAC Name | Exact Mass [M + H]+ |
|---|---|---|---|
| 3-4 | 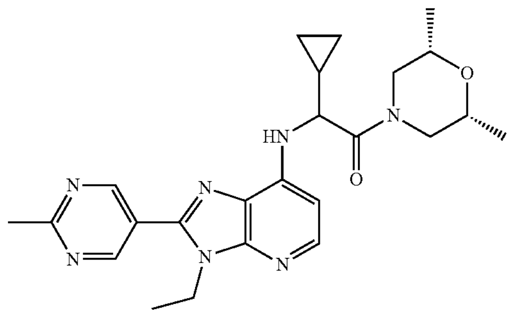 | N-{(R or S)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine | Calc'd 450; found 450 |

Compound Examples of Table 4

Example IV-1 Preparation of Compound 4-1

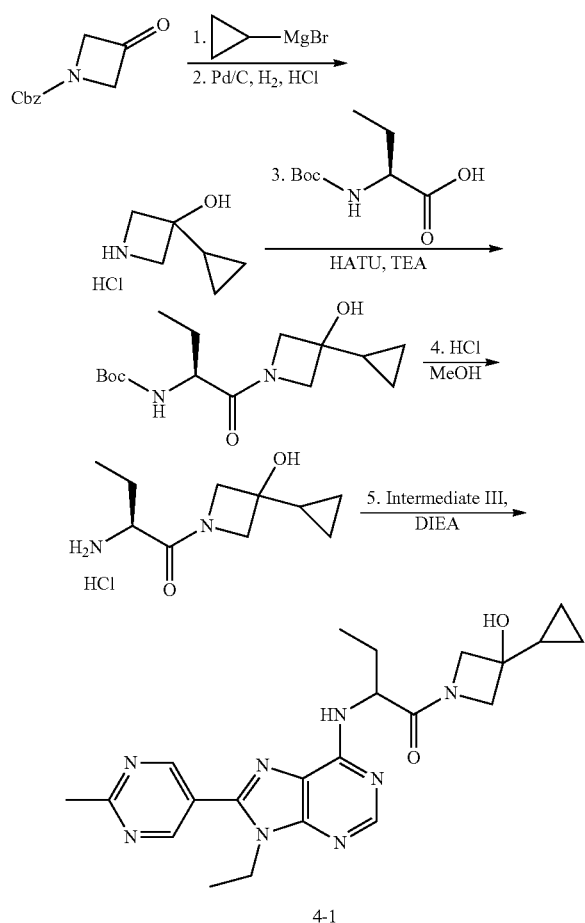

Step 1 Benzyl-3-cyclopropyl-3-hydroxyazetidine-1-carboxylate

To a solution of benzyl 3-oxoazetidine-1-carboxylate (commercially available from Shanghai Jinyi Fine Chemical Co., Ltd) (4.00 g, 19.5 mmol) in THF (20 mL) was added cyclopropylmagnesium bromide (1M solution in THF, 58.5 mL, 58.5 mmol) at −78° C. The resulting solution was allowed to warm to RT where it was stirred for 1 h. The reaction solution was then quenched with water (10 mL), and the resulting mixture was extracted with EtOAc (3×30 mL). The combined organic layers were dried over anhydrous $Na_2SO_4$ and filtered. The filtrate was concentrated under reduced pressure, and the residue obtained was purified by a column chromatography (silica gel, eluting with a gradient of 0%-30% EtOAc in hexanes) to afford benzyl-3-cyclopropyl-3-hydroxyazetidine-1-carboxylate. MS (ESI) Calc'd for $(C_{14}H_{18}NO_3)$ [M+H]$^+$ 248; found 248.

Step 2: 3-Cyclopropylazetidin-3-ol hydrochloride

To a solution of benzyl-3-cyclopropyl-3-hydroxyazetidine-1-carboxylate (2.50 g, 10.1 mmol) in MeOH (15 mL) were added HCl (12 M, 0.84 mL, 10 mmol) and Pd/C (10% by weight, 1.08 g, 1.01 mmol) at RT. The reaction mixture was evacuated and back-filled with hydrogen gas (×3) and was subsequently stirred under hydrogen (1 atm) at RT for 5 h. The reaction mixture was then filtered through a pad of Celite (a trademarked version of diatomaceous earth) and the filtrate was concentrated under reduced pressure to afford 3-cyclopropylazetidin-3-ol hydrochloride which was used in the next step without further purification. MS (ESI) Calc'd for $(C_6H_{12}NO)$ [M+H]$^+$ 114; found 114.

Step 3: (S)-tert-Butyl(1-(3-cyclopropyl-3-hydroxyazetidin-1-yl)-1-oxobutan-2-yl)carbamate To a solution of (S)-2-((tert-butoxycarbonyl)amino)butanoic acid (0.50 g, 2.5 mmol, commercially available from Sichuan Ampebiochem Co., Ltd) in DCM (5 mL) were added HATU (1.12 g, 2.95 mmol) and TEA (1.03 mL, 7.38 mmol) at RT. The resulting solution was stirred for 20 min at RT, after which 3-cyclopropylazetidin-3-ol hydrochloride (0.37 g, 2.5 mmol) was added. The resulting solution was stirred for another 3 h at RT. The reaction solution was then quenched with water (5 mL), and the resulting mixture was extracted with EtOAc (3×10 mL). The combined organic layers were washed with brine (2×10 mL), dried over anhydrous $Na_2CO_3$, and filtered. The filtrate was concentrated under reduced pressure, and the residue obtained was purified by column chromatography (silica gel, eluting with a gradient of 0-30% EtOAc in hexanes) to afford (S)-tertbutyl (1-(3-cyclopropyl-3-hydroxyazetidin-1-yl)-1-oxobutan-2-yl)carbamate. MS (ESI) Calc'd for ($C_{15}H_{27}N_2O_4$) $[M+H]^+$ 299; found 299.

Step 4: (S)-2-Amino-1-(3-cyclopropyl-3-hydroxyazetidin-1-yl)butan-1-one

A solution of (S)-tert-butyl (1-(3-cyclopropyl-3-hydroxyazetidin-1-yl)-1-oxobutan-2-yl)carbamate (0.50 g, 1.7 mmol) in HCl (saturated solution in MeOH, 10 mL) was stirred for 5 h at 25° C. The resulting solution was concentrated under reduced pressure to afford (S)-2-amino-1-(3-cyclopropyl-3-hydroxyazetidin-1-yl)butan-1-one as the hydrogen chloride salt which was used in the next step without further purification. MS (ESI) Calc'd for ($C_{10}H_{19}N_2O_2$) $[M+H]^+$ 199; found 199.

Step 5: Compound 4-1

To a solution of (S)-2-amino-1-(3-cyclopropyl-3-hydroxyazetidin-1-yl)butan-1-one hydrochloride (171 mg, 0.73 mmol) in t-BuOH (5 mL) were added Intermediate III (0.20 g, 0.73 mmol) and DIEA (0.64 mL, 3.6 mmol) at RT. The resulting solution was stirred for 6 h at 80° C. After cooling to RT, the reaction solution was concentrated under reduced pressure. The residue obtained was purified by reverse-phase, preparative HPLC (Column: XBridge Prep C18 OBD, 5 um, 19×150 mm; eluting with a gradient of 25-50% MeCN in aqueous $NH_4HCO_3$ (10 mM); Flow rate: 15 mL/min) to afford 3-cyclopropyl-1-(2-{[9-ethyl-8-(2-methylpyrimidin-5-yl)-9H-purin-6-yl]amino}butanoyl)azetidin-3-ol, which was discovered to have racemized at some point during the synthesis. The racemate was separated by reverse-phase, preparative Chiral HPLC (Column: IA 2.2× 150 mm, 5 um; eluting with 70% EtOH in Hexanes; Flow rate: 20 mL/min) to provide compound 4-1 (faster eluting enantiomer, 6.0 min): $^1$H NMR (400 MHz, $CD_3OD$) δ: 9.03 (s, 2H), 8.26 (s, 1H), 4.63-4.58 (m, 1H), 4.45-4.43 (m, 1H), 4.32-4.27 (m, 3H), 4.06-3.97 (m, 1H), 3.79-3.64 (m, 2H), 2.72 (s, 3H), 1.81-1.76 (m, 2H), 1.33-1.31 (m 3H), 1.15-1.10 (m, 1H), 1.00-0.95 (m, 3H), 0.61-0.58 (m, 2H), 0.41-0.38 (in 2H). MS (ESI) Calc'd for ($C_{22}H_{29}N_8O_2$) $[M+H]^+$ 437; found 437.

Example IV-2 Preparation of Compound 4-2

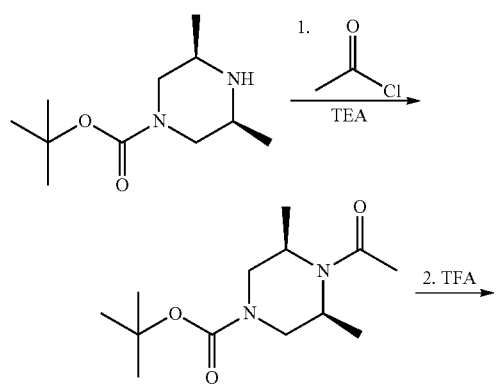

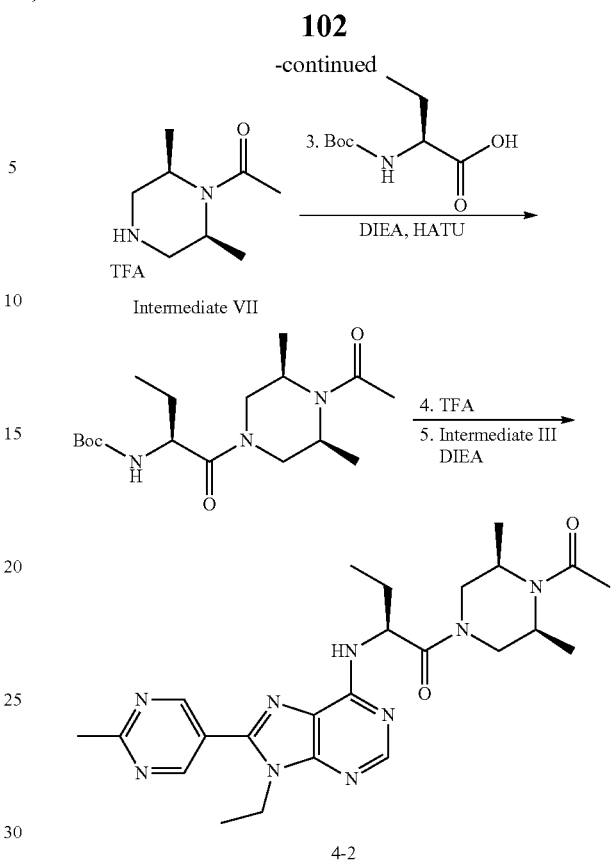

4-2

Step 1: cis-tert-butyl-4-acetyl-3,5-dimethylpiperazine-1-carboxylate

To a solution of cis-tert-butyl 3,5-dimethylpiperazine-1-carboxylate (commercially available from Guangzhou Kerui) (100 mg, 0.47 mmol) in DCM (1 mL) was added TEA (0.06 mL, 0.47 mmol) at RT, after which the solution was cooled to 0° C. and acetyl chloride (0.03 mL, 0.47 mmol) was added. The resulting solution was allowed to come to RT and stirred for 2 h. The reaction mixture was then diluted with water (1 mL), and the resulting mixture was extracted with EtOAc (3×5 mL). The combined organic layers were washed with brine (5 mL), dried over anhydrous $Na_2SO_4$, and filtered. The filtrate was concentrated under reduced pressure, and the residue obtained was purified by column chromatography (silica gel, eluting with a gradient of 0-5% MeOH in DCM) to afford cis-tert-butyl-4-acetyl-3,5-dimethylpiperazine-1-carboxylate. MS (ESI) Calc'd for ($C_{13}H_{25}N_2O_3$) $[M+H]^+$ 256; found 256.

Step 2: 1-cis-2,6-Dimethylpiperazin-1-yl)ethanone

To a solution of cis-tert-butyl 4-acetyl-3,5-dimethylpiperazine-1-carboxylate (100 mg, 0.39 mmol) in DCM (5 mL) was added TFA (2.0 mL, 27 mmol), after which the solution was allowed to stir for 4 h at RT. The resulting solution was concentrated under reduced pressure to afford 1-cis-2,6-dimethylpiperazin-1-yl)ethanone 2,2,2-trifluoroacetate which was used in the next step directly without further purification. MS (ESI) Calc'd for ($C_8H_{17}N_2O$) $[M+H]^+$ 156; found 156.

Step 3: tert-Butyl-(S)-1-(cis-4-acetyl-3,5-dimethyl-piperazin-1-yl)-1-oxobutan-2-ylcarbamate To a solution of (S)-2-((tert-butoxycarbonyl)amino)butanoic acid (75 mg, 0.37 mmol) in DCM (2 mL) were added HATU (169 mg, 0.44 mmol) and DIEA (0.18 mL, 1.11 mmol) at 20° C. The reaction solution was stirred for 15 min at 20° C., after which 1-cis-2,6-dimethylpiperazin-1-yl)ethanone 2,2,2-trifluoroacetate (100 mg, 0.37 mmol) was added. The resulting solution was stirred for another 14 h at RT, after which the reaction solution was quenched with water (3 mL). The resulting mixture was extracted with EtOAc (3×10 mL), and the combined organic layers were washed with brine (2×10 mL), dried over anhydrous $Na_2SO_4$, and filtered. The filtrate was concentrated under reduced pressure, and the residue obtained was purified by column chromatography (silica gel, eluting with a gradient of 0-10% MeOH in DCM) to afford tert-butyl-(S)-1-cis-4-acetyl-3,5-dimethyl-piperazin-1-yl)-1-oxobutan-2-ylcarbamate. MS (ESI) Calc'd for ($C_{17}H_{32}N_3O_4$) [M+H]$^+$ 342; found 342.

Step 4: (S)-1-(cis-4-Acetyl-3,5-dimethylpiperazin-1-yl)-2-aminobutan-1-one

To a solution of tert-butyl-((S)-1-(cis-4-acetyl-3,5-dimethylpiperazin-1-yl)-1-oxobutan-2-yl)carbamate (121 mg, 0.35 mmol) in DCM (5 mL) was added TFA (2.0 mL, 27 mmol) at RT, after which the reaction was allowed to stir for 4 h. The resulting solution was concentrated under reduced pressure to afford (S)-1-cis-4-acetyl-3,5-dimethylpiperazin-1-yl)-2-aminobutan-1-one 2,2,2-trifluoroacetate which was used in the next step without further purification. MS (ESI) Calc'd for ($C_{12}H_{23}N_3O_2$) [M+H]$^+$ 242; found 242.

Step 5: Compound 4-2

To a solution of (S)-1-(cis-4-acetyl-3,5-dimethylpiperazin-1-yl)-2-aminobutan-1-one 2,2,2-trifluoroacetate (125 mg, 0.35 mmol) in t-BuOH (3 mL) were added Intermediate III (0.10 g, 0.36 mmol) and DIEA (0.13 mL, 0.73 mmol) at RT. The resulting solution was stirred for 4 h at 80° C. The reaction solution was then cooled to RT and concentrated under reduced pressure. The residue obtained was purified by reverse-phase, preparative HPLC (Column: X Bridge C18, 19×150 mm, 5 um; eluting with a gradient of 2%-20% MeCN in aqueous $NH_4CO_3$ (10 mM)) to afford 4-2. $^1$H NMR (300 MHz, $CD_3OD$): δ 9.09 (s, 2H), 8.31-8.25 (m, 1H), 5.28 (brs, 1H), 4.64-4.62 (m, 1H), 4.42-4.33 (m, 3H), 4.29-4.05 (m, 2H), 3.46 (brs, 1H), 2.91 (brs, 1H), 2.79 (s, 3H), 2.13 (s, 3H), 2.05-1.78 (m, 2H), 1.42-1.30 (m, 6H), 1.29-0.99 (m, 6H). MS (ESI) Calc'd for ($C_{24}H_{33}N_9O_2$) [M+H]$^+$ 480; found 480.

Example IV-3 Preparation of Compound 4-3

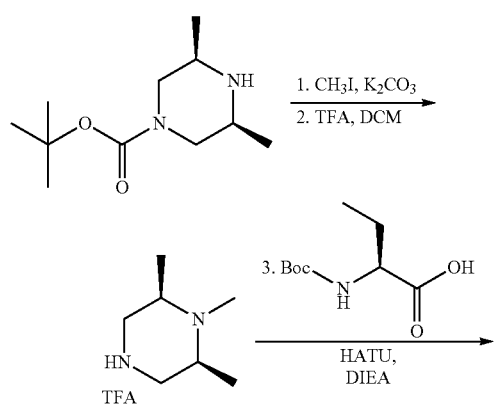

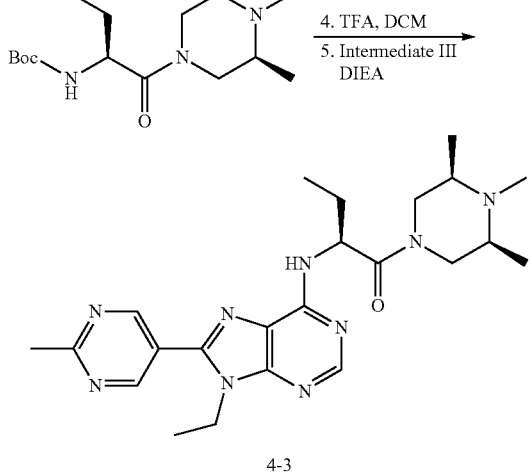

4-3

Step 1: cis-tert-Butyl-3,4,5-trimethylpiperazine-1-carboxylate

To a solution of cis-tert-butyl-3,5-dimethylpiperazine-1-carboxylate (0.50 g, 2.33 mmol) in DCM (5 mL) were added $K_2CO_3$ (0.65 g, 4.67 mmol) and iodomethane (0.15 mL, 2.33 mmol) at RT. The resulting mixture was stirred for 2 h at RT, after which the reaction mixture was diluted with water (1 mL). The resulting mixture was extracted with EtOAc (3×5 mL), and the combined organic layers were washed with brine (5 mL), dried over anhydrous $Na_2SO_4$, and filtered. The filtrate was concentrated under reduced pressure, and the residue obtained was purified by column chromatography (silica gel, eluting with a gradient of 0-5% MeOH in DCM) to afford cis-tert-butyl-3,4,5-trimethylpiperazine-1-carboxylate. MS (ESI) Calc'd for ($C_{12}H_{25}N_2O_2$) [M+H]$^+$ 229; found 229.

Step 2: cis-1,2,6-Trimethylpiperazine

To a solution of cis-tert-butyl 3,4,5-trimethylpiperazine-1-carboxylate (160 mg, 0.70 mmol) in DCM (5 mL) was added TFA (2.0 mL, 27 mmol), after which the resulting mixture was allowed to stir at RT for 4 h. The solution was then concentrated under reduced pressure to afford cis-1,2,6-trimethylpiperazine 2,2,2-trifluoroacetate salt which was used in the next step without further purification. MS (ESI) Calc'd for ($C_7H_{17}N_2$) [M+H]$^+$ 129; found 129.

Step 3: tert-Butyl-(S)-1-oxo-1-(cis-3,4,5-trimethylpiperazine-1-yl)butan-2-ylcarbamate To a solution of (S)-2-((tert-butoxycarbonyl)amino)butanoic acid (131 mg, 0.65 mmol) in DCM (5 mL) were added HATU (0.29 g, 0.77 mmol) and DIEA (0.32 mL, 1.93 mmol). The solution was allowed to stir at RT for 15 min, after which cis-1,2,6-trimethylpiperazine 2,2,2-trifluoroacetate (156 mg, 0.64 mmol) was added. The resulting solution was stirred for another 14 h at RT. The reaction solution was then quenched with water (3 mL), and the resulting mixture was extracted with EtOAc (3×10 mL). The combined organic layers were washed with brine (2×10 mL), dried over anhydrous $Na_2SO_4$, and filtered. The filtrate was concentrated under reduced pressure, and the residue obtained was purified by a column chromatography (silica gel, eluting with a gradient of 0-10% MeOH in DCM) to afford tert-butyl-((S)-1-oxo-1-(cis-3,4,5-trimethylpiperazin-1-yl)butan-2-yl)carbamate. MS (ESI) Calc'd for $(C_{16}H_{32}N_3O_3)$ $[M+H]^+$ 314; found 314.

Step 4: (S)-1-(cis-4-Acetyl-3,5-dimethylpiperazin-1-yl)-2-aminobutan-1-one

To a solution of tert-butyl-((S)-1-oxo-1-(cis-3,4,5-trimethylpiperazin-1-yl)butan-2-yl)carbamate (120 mg, 0.38 mmol) in DCM (5 mL) was added TFA (2.0 mL, 27 mmol), and the resulting mixture was allowed to stir at RT for 4 h. The resulting solution was concentrated under reduced pressure to afford (S)-2-amino-1-(cis-3,4,5-trimethylpiperazin-1-yl)butan-1-one 2,2,2-trifluoroacetate which was used in the next step without further purification. MS (ESI) Calc'd for $(C_{11}H_{24}N_3O)$ $[M+H]^+$ 214; found 214.

Step 5: Compound 4-3

To a solution of (S)-2-amino-1-(cis-3,4,5-trimethylpiperazin-1-yl)butan-1-one 2,2,2-trifluoroacetate (120 mg, 0.36 mmol) in t-BuOH (3 mL) were added Intermediate III (0.10 g, 0.36 mmol) and DIEA (0.13 mL, 0.73 mmol) at RT. The resulting solution was stirred for 4 h at 80° C. The reaction mixture was then cooled to RT concentrated under reduced pressure. The residue obtained was purified by reverse-phase, preparative HPLC (Column: X Bridge C18, 19×150 mm, 5 um; eluting with a gradient of 2-20% MeCN in aqueous $NH_4HCO_3$ (10 mM)) to afford 4-3. $^1$H NMR (300 MHz, $CD_3OD$): δ 9.09 (s, 2H), 8.29 (s, 1H), 5.29 (brs, 1H), 4.39-4.32 (m, 3H), 4.19-4.02 (m, 1H), 3.04-2.96 (m, 1H), 2.79 (s, 3H), 2.55-2.44 (m, 1H), 2.29-2.26 (m, 3H), 2.23-2.13 (m, 1H), 1.99-1.77 (m, 3H), 1.42-1.35 (m, 3H), 1.21-0.81 (m, 9H). MS (ESI) Calc'd for $(C_{23}H_{34}N_9O)$ $[M+H]^+$ 452; found 452.

Example IV-4 Preparation of Compound 4-4

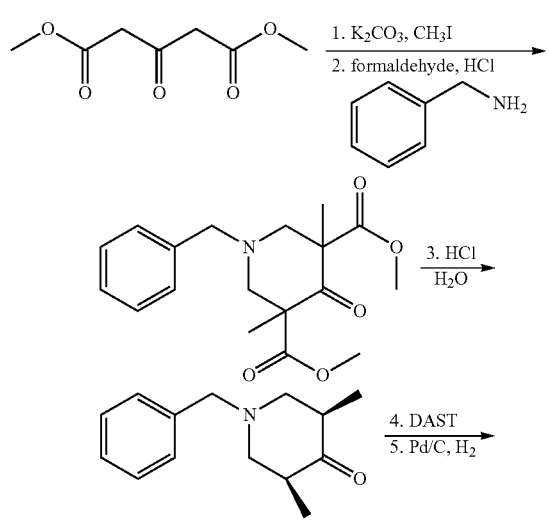

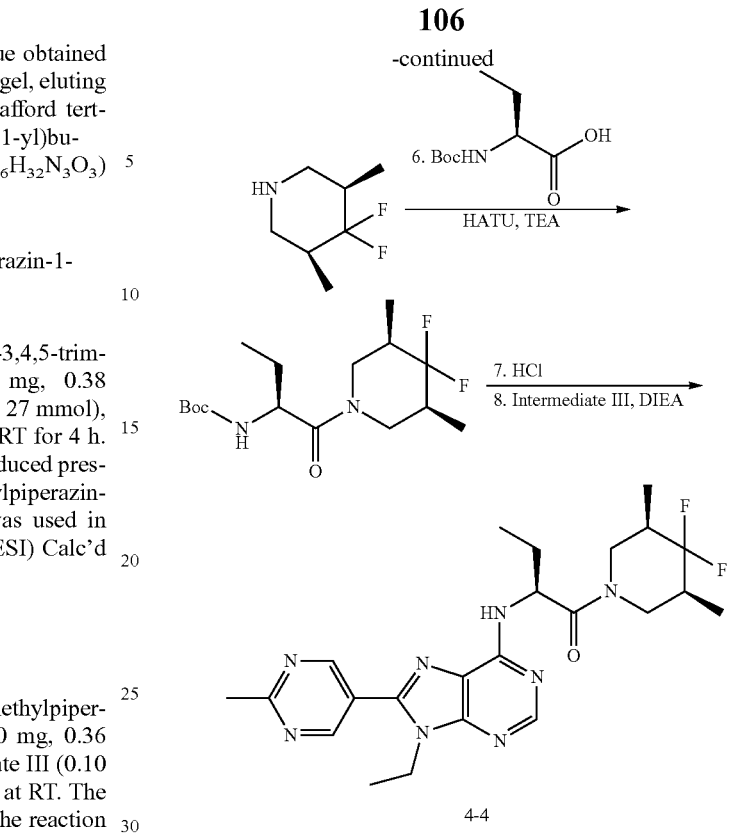

4-4

Step 1: Dimethyl-2,4-dimethyl-3-oxopentanedioate

To a solution of dimethyl-3-oxopentanedioate (26.0 g, 149 mmol) in THF (150 mL) was added $K_2CO_3$ (51.6 g, 373 mmol) at RT. The resulting mixture was stirred for 20 min at 45° C., after which iodomethane (42.4 g, 299 mmol) was added and the solution was allowed to stir at 60° C. for 1 h. The reaction mixture was then cooled to RT and filtered, and the filter cake was washed with THF (500 mL). The filtrate was concentrated under reduced pressure to afford dimethyl-2,4-dimethyl-3-oxopentanedioate which was used for next step directly without further purification. MS (ESI) calc'd for $(C_9H_{15}O_5)$ $[M+H]^+$ 203; found 203.

Step 2: Dimethyl-1-benzyl-3,5-dimethyl-4-oxopiperidine-3,5-dicarboxylate

To a solution of dimethyl-2,4-dimethyl-3-oxopentanedioate (23.0 g, 114 mmol) in MeOH (300 mL) at 9° C. were added sequentially aqueous HCl (1 M, 23.0 mL, 22.8 mmol), benzylamine (12.2 g, 114 mmol), and formaldehyde (37% wt. in water, 18.7 mL, 227 mmol). The resulting solution was then stirred for 4 h at RT. The reaction solution was then concentrated under reduced pressure to afford dimethyl-1-benzyl-3,5-dimethyl-4-oxopiperidine-3,5-dicarboxylate which was used in the next step without further purification. MS (ESI) calc'd for $(C_{18}H_{24}NO_5)$ $[M+H]^+$ 334; found 334.

Step 3: cis-1-Benzyl-3,5-dimethylpiperidin-4-one

A solution of dimethyl-1-benzyl-3,5-dimethyl-4-oxopiperidine-3,5-dicarboxylate (22.0 g, 39.6 mmol) in aqueous HCl (1 M, 330 mL, 330 mmol) was stirred for 72 hours at 100° C. After cooling to 10° C., the reaction solution was quenched with aqueous NaOH (2 M, 50 mL, 100 mmol).

The resulting solution was extracted with DCM (3×100 mL), and the combined organic layers were washed with brine (60 mL), dried over anhydrous MgSO$_4$, and filtered. The filtrate was concentrated under reduced pressure, and the residue obtained was purified by column chromatography (silica gel using, eluting with a gradient of 5-20% EtOAc in hexanes) to afford cis-1-benzyl-3,5-dimethylpiperidin-4-one. MS (ESI) calc'd for (C$_{14}$H$_{20}$NO) [M+H]$^+$ 218; found 218.

Step 4:
cis-1-Benzyl-4,4-difluoro-3,5-dimethylpiperidine

To a solution of cis-1-benzyl-3,5-dimethylpiperidin-4-one (3.00 g, 13.8 mmol) in DCM (40 mL) was added DAST (9.12 mL, 69.0 mmol) at RT. The resulting solution was heated to 40° C. and stirred for 14 h. After cooling to the RT, the reaction solution was quenched with saturated aqueous NaHCO$_3$ (100 mL). The resulting mixture was extracted with DCM (3×50 mL), and the combined organic layers were washed with brine (50 mL), dried over anhydrous MgSO$_4$, and filtered. The filtrate was concentrated under reduced pressure, and the residue obtained was purified by column chromatography (silica gel, eluting with a gradient of 5-20% EtOAc in Hexanes) to afford cis-1-benzyl-4,4-difluoro-3,5-dimethylpiperidine. MS (ESI) calc'd for (C$_{14}$H$_{20}$F$_2$N) [M+H]$^+$ 240; found 240.

Step 5: cis-4,4-Difluoro-3,5-dimethylpiperidine

To a solution of cis-1-benzyl-4,4-difluoro-3,5-dimethylpiperidine (0.60 g, 2.51 mmol) in MeOH (10 mL) was added Pd/C (20% wt., 0.33 g, 0.63 mmol) at RT. The reaction mixture was evacuated and backfilled with hydrogen gas (×3), after which it was stirred under hydrogen (1 atm) at RT for 20 h. The reaction mixture was then filtered, and the filtrate was concentrated under reduced pressure to afford cis-4,4-difluoro-3,5-dimethylpiperidine which was used in the next step without further purification. MS (ESI) calc'd for (C$_{17}$H$_{14}$F$_2$N) [M+H]$^+$ 150; found 150.

Step 6. tert-Butyl-((S)-1-(cis-4,4-difluoro-3,5-dimethylpiperidin-1-yl)-1-oxobutan-2-yl)carbamate To a solution of (S)-2-((tert-butoxycarbonyl)amino)butanoic acid (0.34 g, 1.68 mmol) in MeCN (10 mL) were added HATU (0.64 g, 1.68 mmol) and TEA (0.34 g, 3.35 mmol) at RT. The reaction was allowed to stir at RT for 1 h, after which cis-4,4-difluoro-3,5-dimethylpiperidine (0.25 g, 1.68 mmol) was added. The resulting solution was stirred for another 2 h at RT. Water (30 mL) was then poured into the reaction solution, and the resulting mixture was extracted with EtOAc (3×20 mL). The combined organic layers were washed by brine (30 mL), dried over anhydrous Na$_2$SO$_4$, and filtered. The filtrate was concentrated under reduced pressure to afford tert-butyl-((S)-1-(cis-4, 4-difluoro-3,5-dimethylpiperidin-1-yl)-1-oxobutan-2-yl)carbamate which used in the next step without further purification. MS (ESI) calc'd for (C$_{16}$H$_{29}$F$_2$N$_2$O$_3$) [M+H]$^+$ 335; found 335.

Step 7: (S)-2-Amino-1-(cis-4,4-difluoro-3,5-dimethylpiperidin-1-yl)butan-1-one hydrochloride HCl gas was bubbled through a solution of tert-butyl ((S)-1-(cis-4,4-difluoro-3,5-dimethylpiperidin-1-yl)-1-oxobutan-2-yl)carbamate (0.32 g, 0.96 mmol) in EtOAc (15 mL), after which the resulting mixture was stirred for 4 h at RT. The solution was then concentrated under reduced pressure to afford (S)-2-amino-1-(cis-4,4-difluoro-3,5-dimethylpiperidin-1-yl)butan-1-one hydrochloride which was used in the next step without further purification. MS (ESI) calc'd for (C$_{11}$H$_{21}$F$_2$N$_2$O) [M+H]$^+$ 235; found 235.

Step 8: Compound 4-4

To a RT solution of (S)-2-amino-1-(cis-4,4-difluoro-3,5-dimethylpiperidin-1-yl)butan-1-one hydrochloride (100 mg, 0.37 mmol) in t-BuOH (5 mL) were added Intermediate III (101 mg, 0.37 mmol) and DIEA (0.13 mL, 0.74 mmol). The resulting solution was heated to 80° C. where it was stirred for 48 h. The reaction mixture was then cooled to RT and was concentrated under reduced pressure. The residue obtained was purified by column chromatography (silica gel, eluting with a gradient of 0-10% EtOAc in hexanes) to afford the crude product. The crude product was further purified by reverse-phase, preparative HPLC (Column: X Bridge C18, 19×150 mm, 5 um; eluting with a gradient of 28-65% MeCN in aqueous NH$_4$HCO$_3$ (10 mM); Flow rate: 20 mL/min) to afford compound 4-4. $^1$H NMR (300 MHz, DMSO-d6): δ 9.19 (s, 2H), 8.25 (s, 1H), 7.93-7.71 (m, 1H), 5.18 (s, 1H), 4.42-4.15 (m, 4H), 2.96-2.88 (m, 1H), 2.75 (s, 3H), 1.81 (s, 3H), 1.33-1.15 (m, 4H), 1.01-0.68 (m, 10H). MS (ESI) calc'd for (C$_{23}$H$_{31}$F$_2$N$_8$O) [M+H]$^+$ 473; found 473.

Example IV-5 Preparation of Compounds 4-5 and 4-6

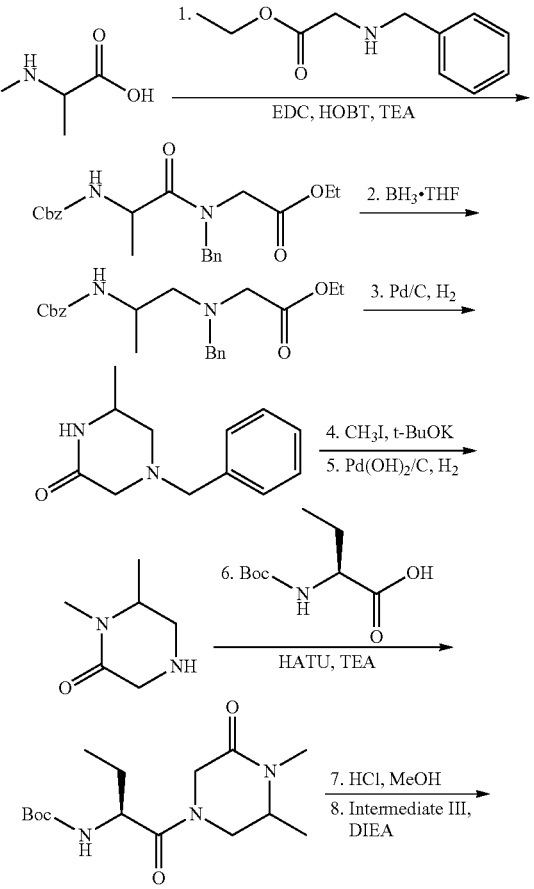

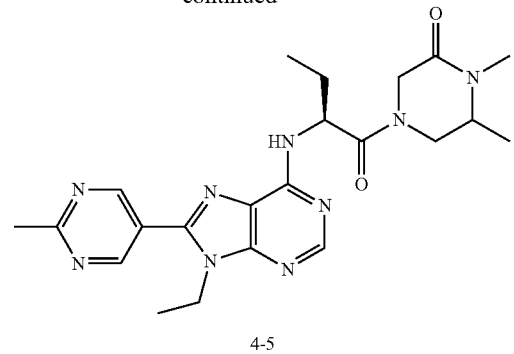

4-5

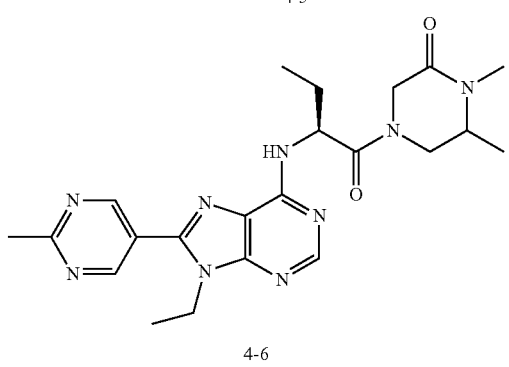

4-6

Step 1: Ethyl-2-(N-benzyl-2-(((benzyloxy)carbonyl)amino)propanamido)acetate

To a stirred solution of 2-(((benzyloxy)carbonyl)amino) propanoic acid (9.0 g, 40.3 mmol) in DCM (200 ml) were added ethyl 2-(benzylamino)acetate (7.79 g, 40.3 mmol), HOBT (6.79 g, 44.3 mmol), EDC (8.50 g, 44.3 mmol) and TEA (11.24 ml, 81 mmol). The solution was stirred for 10 h at RT, after which the solution was diluted with DCM (400 mL). The organic layer was then extracted with water (3×200 mL), washed with brine (200 mL), dried over anhydrous $Na_2SO_4$ and filtered. The filtrate was concentrated in vacuo, and the residue obtained was purified by column chromatography (silica gel, eluting with a gradient of 10-25% EtOAc in hexanes) to give ethyl 2-(N-benzyl-2-(((benzyloxy)carbonyl)amino)propanamido)acetate. MS (ESI) Calc'd for ($C_{22}H_{27}N_2O_5$) [M+H]$^+$ 399; found 399.

Step 2: Ethyl-2-(benzyl(2-(((benzyloxy)carbonyl)amino)propyl)amino)acetate

To a solution of ethyl-2-(N-benzyl-2-(((benzyloxy)carbonyl)amino) propanamido)acetate (11.1 g, 27.9 mmol) in THF (200 mL) was added $BH_3THF$ solution (1M, 84 mL, 84 mmol). The resulting solution was stirred for 10 h at RT. The reaction solution was then quenched with the EtOH (100 mL), and the resulting solution was stirred for 15 min. The solution was concentrated under reduced pressure, and the residue obtained was dissolved in EtOAc (500 mL). The organic layer was then washed with brine (150 mL), dried over anhydrous $Na_2SO_4$, and filtered. The filtrate was concentrated under reduced pressure, and the residue obtained was purified by column chromatography (silica gel, eluting with a gradient of 10-30% EtOAc in hexanes) to afford ethyl-2-(benzyl(2-(((benzyloxy)carbonyl) amino)propyl) amino)acetate. MS (ESI) Calc'd for ($C_{22}H_{29}N_2O_4$) [M+H] 385; found 385.

Step 3: 4-Benzyl-6-methylpiperazin-2-one

Pd/C (10% by weight, 1.11 g, 1.04 mmol) was added into the solution of ethyl 2-(benzyl(2-(((benzyloxy)carbonyl) amino)propyl)amino)acetate (8.0 g, 21 mmol) in MeOH (150 ml). The solution was evacuated and backfilled with hydrogen gas (×3). The solution was then stirred for 2 h at RT under an atmosphere of hydrogen (1 atm). The solution was then filtered, and the filtrate was concentrated in vacuo. The residue obtained was purified by column chromatography (silica gel, eluting with a gradient of 20-50% EtOAc in hexanes) to give 4-benzyl-6-methylpiperazin-2-one. MS (ESI) Calc'd for ($C_{12}H_{17}N_2O$) [M+H]$^+$ 205; found 205.

Step 4: 4-Benzyl-1,6-dimethylpiperazin-2-one

To a solution of iodomethane (167 mg, 1.18 mmol) in DMF (5 mL) at 0° C. were added 4-benzyl-6-methylpiperazin-2-one (0.20 g, 0.98 mmol) and potassium tert-butoxide (0.22 g, 2.0 mmol). The resulting mixture was allowed to warm to RT and was stirred for 5 h. The pH value of the solution was then adjusted to 8 by the addition of aqueous acetic acid (1M). The solution was then concentrated under reduced pressure, and the residue obtained was purified by column chromatography (silica gel, eluting with a gradient of 20-50% EtOAc in hexanes) to afford 4-benzyl-1,6-dimethylpiperazin-2-one. MS (ESI) Calc'd for ($C_{13}H_{19}N_2O$) [M+H]$^+$ 219; found 219.

Step 5: 1,6-Dimethylpiperazin-2-one

Pd(OH)$_2$ (61 mg, 0.086 mmol) was added into the solution of 4-benzyl-1,6-dimethylpiperazin-2-one (188 mg, 0.861 mmol) in MeOH (20 ml). The solution was evacuated and backfilled with hydrogen gas (×3), after which it was stirred for 3 h at RT under an atmosphere of hydrogen (1 atm). The solution was then filtered through a pad of Celite (a trademarked version of diatomaceous earth) and the filter cake was washed with EtOAc (50 mL). The filtrate was concentrated in vacuo to give 1,6-dimethylpiperazin-2-one which was used in the next step without further purification. MS (ESI) Calc'd for ($C_6H_{13}N_2O$) [M+H]$^+$ 129; found 129.

Step 6: tert-Butyl((2S)-1-(3,4-dimethyl-5-oxopiperazin-1-yl)-1-oxobutan-2-yl) carbamate To a stirred solution of 1,6-dimethylpiperazin-2-one (91 mg, 0.71 mmol) in THF (5 ml) were added TEA (0.2 ml, 1.4 mmol), HATU (320 mg, 0.85 mmol) and (S)-2-((tert-butoxycarbonyl)amino)butanoic acid (173 mg, 0.852 mmol). The solution was stirred for 2 h at RT, after which the solution was concentrated in vacuo. The residue obtained was purified by column chromatography (silica gel, eluting with a gradient of 0-80% EtOAc in hexanes) to give tert-butyl ((2S)-1-(3,4-dimethyl-5-oxopiperazin-1-yl)-1-oxobutan-2-yl)carbamate. MS (ESI) Calc'd for ($C_{15}H_{28}N_3O_4$) [M+H]$^+$ 314; found 314.

Step 7: 4-((S)-2-Aminobutanoyl)-1,6-dimethylpiperazin-2-one

To a stirred solution of HCl in MeOH (10 ml) was added tert-butyl ((2S)-1-(3,4-dimethyl-5-oxopiperazin-1-yl)-1-oxobutan-2-yl)carbamate (137 mg, 0.437 mmol), after which the solution was stirred for 5 h at RT. The solution was then concentrated under reduced pressure, and the residue obtained was dissolved in DCM (50 mL). The PH of the solution was then adjusted to 8 via the addition of TEA, after which the solution was concentrated under reduced pressure. The residue obtained was purified by column chromatography (silica gel, eluting with a gradient of 0-10% MeOH in DCM) to afford 4-((S)-2-aminobutanoyl)-1,6-dimethylpiperazin-2-one. MS (ESI) Calc'd for ($C_{10}H_{20}N_3O_2$) [M+H]$^+$ 214; found 214.

Step 8: Compounds 4-5 and 4-6

To a solution of Intermediate III (40 mg, 0.15 mmol) and DIEA (0.127 ml, 0.728 mmol) in t-BuOH (3 ml) was added 4-((S)-2-aminobutanoyl)-1,6-dimethylpiperazin-2-one (62.1 mg, 0.29 mmol). The resulting solution was stirred for 36 h at 80° C. After cooling to RT, the solution was quenched with the addition of water (30 mL). The resulting mixture was extracted with EtOAc (5×30 mL). The combined organic layers were washed with brine (50 mL), dried over anhydrous $Na_2SO_4$, and filtered. The filtrate was concentrated in vacuo, and the residue obtained was purified by column chromatography (silica gel, eluting with a gradient of 5%-10% MeOH in DCM) to afford the crude product, which was further purified by reverse-phase, preparative HPLC (XSelect CSH Prep C18 OBD Column, 5 um, 19×150 mm; eluting with a gradient of 18%-25% MeCN in aqueous $NH_4CO_3$ (10 mM); Flow rate: 20 mL/min) to afford 4-5 (faster eluting isomer) $^1$H NMR (300 MHz, DMSO-d6, 353K) δ 9.07 (s, 2H), 8.25 (s, 1H), 7.32 (d, J=8.4 Hz, 1H), 6.69-6.50 (m, 1H), 5.37-5.09 (m, 1H), 4.33-4.26 (m, 2H), 4.17-3.83 (m, 2H), 3.83-3.29 (m, 2H), 2.81 (s, 3H), 2.74 (s, 3H), 1.92-1.76 (m, 2H), 1.34-1.29 (m, 3H), 1.23-0.94 (m, 6H). MS (ESI) Calc'd for ($C_{22}H_{30}N_9O_2$) [M+H]$^+$ 452; found 452; and 4-6 (slower eluting isomer): $^1$H NMR (300 MHz, DMSO-d$_6$, 353K) δ 9.09 (s, 2H), 8.26 (s, 1H), 7.21 (d, J=8.4 Hz, 1H), 5.60-4.88 (m, 1H), 4.42-4.20 (m, 3H), 4.18-3.72 (m, 2H), 3.70-3.35 (m, 2H), 2.84 (s, 3H), 2.74 (s, 3H), 2.00-1.76 (m, 2H), 1.35-1.30 (t, J=7.2 Hz, 3H), 1.15 (d, J=6.6 Hz, 3H), 0.97-0.93 (m, 3H). MS (ESI) calc'd for ($C_{22}H_{30}N_9O_2$) [M+H]$^+$ 452; found 452.

Example IV-6 Preparation of Compound 4-7

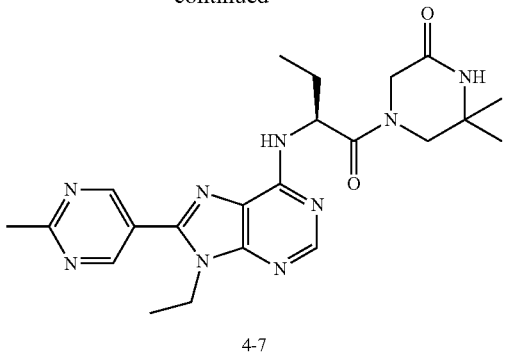

4-7

Step 1:
Benzyl-(1-amino-2-methylpropan-2-yl)carbamate

A solution of benzyl-(2-cyanopropane-2-yl)carbamate[4] (2.20 g, 10.1 mmol) in THF (20 mL) was added to a mixture of lithium aluminum hydride (383 mg, 10.1 mmol) in THF (20 mL) at 0° C. The resulting mixture was allowed to come to RT and was stirred for 3 h. The reaction was then quenched by the addition of saturated aqueous magnesium sulfate solution (20 mL), after which the solution was filtered. The filtrate was extracted with ether (3×30 mL), and the combined organic layers were concentrated under reduced pressure to afford benzyl-(1-amino-2-methylpropan-2-yl)carbamate, which was used in the next step directly without further purification. MS (ESI) calc'd for ($C_{12}H_{19}N_2O_2$) [M+H]$^+$, 223; found 223.

[4]For the preparation of benzyl-(2-cyanopropan-2-yl)carbamate, see Potassium salt of an HIV integrase inhibitor. Belyk, K., et al. PCT US Appl. (2006); US 2006/0122205.

Step 2: Ethyl-2-((2-(((benzyloxy)carbonyl)amino)-2-methylpropyl)amino)acetate

To a solution of benzyl-(1-amino-2-methylpropan-2-yl)carbamate (0.20 g, 4.1 mmol) in EtOAc (10 mL) were added ethyl-2-bromoacetate (1.01 g, 6.07 mmol) and TEA (0.41 g, 4.1 mmol), after which the reaction mixture was stirred for 5 h at RT. The reaction mixture was then quenched with water (10 mL), and the resulting mixture was extracted with EtOAc (3×10 mL). The combined organic layers were washed with brine (10 mL), dried over anhydrous $Na_2SO_4$, and filtered. The filtrate was concentrated under reduced pressure, and the residue obtained was purified by column chromatography (silica gel, eluting with a gradient of 0-50% EtOAc in hexanes) to afford ethyl-2-((2-(((benzyloxy)carbonyl)amino)-2-methylpropyl) amino)acetate. MS (ESI) calc'd for ($C_{16}H_{25}N_2O_4$) [M+H]$^+$, 309; found 309.

Step 3: 6,6-Dimethylpiperazin-2-one

To a solution of ethyl 2-((2-(((benzyloxy)carbonyl) amino)-2-methylpropyl)amino)acetate (0.40 g, 1.30 mmol) in MeOH (15 ml) was added Pd/C (10% wt., 1.38 g, 1.30 mmol). The solution was evacuated and backfilled with hydrogen gas (×3), after which it was stirred for 3 h at RT under an atmosphere of hydrogen (1 atm). The reaction mixture was then filtered, and the filtrate was concentrated under reduced pressure to afford 6,6-dimethylpiperazin-2-one, which was used in the next step without further purification. MS (ESI) calc'd for ($C_6H_{13}N_2O$) [M+H]$^+$ 129; found 129.

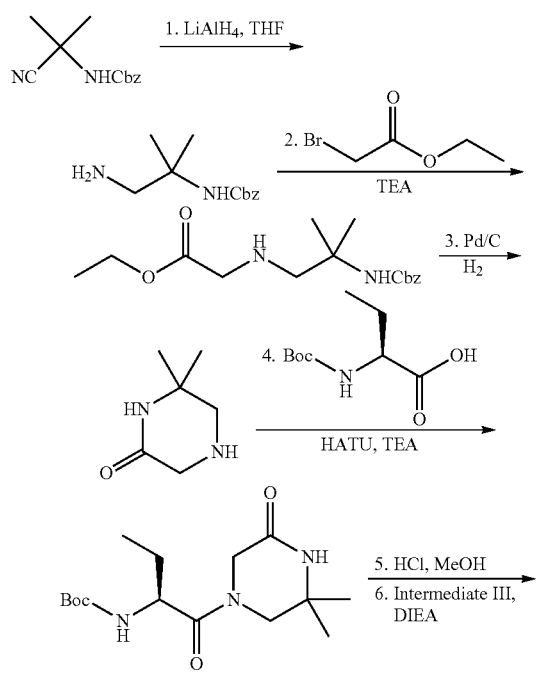

Step 4: (S)-tert-Butyl(1-(3,3-dimethyl-5-oxopiperazin-1-yl)-1-oxobutan-2-yl) carbamate To a solution of (S)-2-((tert-butoxycarbonyl)amino)butanoic acid (0.22 g, 1.1 mmol) in DCM (10 mL) were added TEA (0.22 g, 2.2 mmol) and HATU (0.50 g, 1.3 mmol), after which the solution was stirred for 30 min at RT. 6,6-dimethylpiperazin-2-one (140 mg, 1.1 mmol) was then added, and the resulting solution was further stirred for another 5 h at RT. The resulting mixture was then quenched with water (5 mL), and the resulting mixture was extracted with DCM (3×10 mL). The combined organic layers were washed with brine (10 mL), dried over anhydrous $Na_2SO_4$, and filtered. The filtrate was concentrated under reduced pressure, and the residue obtained was purified by column chromatography (silica gel, eluting with a gradient of 0-30% MeOH in DCM to afford (S)-tert-butyl-(1-(3,3-dimethyl-5-oxopiperazin-1-yl)-1-oxobutan-2-yl)carbamate. MS (ESI) calc'd for $(C_{15}H_{28}N_3O_4)$ $[M+H]^+$ 314; found 314.

Step 5: (S)-4-(2-Aminobutanoyl)-6,6-dimethylpiperazin-2-one hydrochloride (S)-tert-butyl (1-(3,3-dimethyl-5-oxopiperazin-1-yl)-1-oxobutan-2-yl)carbamate (2.5 g, 0.80 mmol) was added to a solution of HCl in MeOH (1 M, 2.5 mL, 2.5 mmol) at 0° C. The resulting mixture was stirred for 2 h at RT, after which the reaction mixture was concentrated under reduced pressure to afford (S)-4-(2-aminobutanoyl)-6,6-dimethylpiperazin-2-one hydrochloride, which was used in the next step without further purification. MS (ESI) calc'd for $(C_{10}H_{20}N_3O_2)$ $[M+H]^+$ 214. found 214.

Step 6: Compound 4-7

To a solution of (S)-4-(2-aminobutanoyl)-6,6-dimethylpiperazin-2-one hydrochloride (120 mg, 0.48 mmol) and DIEA (0.31 g, 2.40 mmol) in IPA (5 mL) was added Intermediate III (132 mg, 0.48 mmol) at RT. The resulting solution was stirred for 5 h at 80° C. The reaction mixture was then cooled to RT and quenched by the addition of water (5 mL). The mixture was extracted with EtOAc (3×5 mL), and the combined organic layers were dried over anhydrous $Na_2SO_4$ and filtered. The filtrate was concentrated under reduced pressure, and the residue obtained was purified by reverse-phase, preparative HPLC (Column: XBridge Prep C18 OBD Column, 19×150 mm 5 um; eluting with a gradient of 15%-60% MeCN in aqueous $NH_4HCO_3$ (10 mM)) to afford 4-7. $^1$H NMR (300 MHz, $CDCl_3$): δ 9.04 (s, 2H), 8.38 (s, 1H), 6.70-6.35 (m, 1H), 6.10-6.07 (m, 1H), 5.60-5.23 (m, 1H), 4.74-3.99 (m, 4H), 3.63-3.49 (m, 1H), 2.87 (s, 3H), 2.06-1.95 (m, 1H), 1.88-1.82 (m, 1H), 1.50-1.47 (m, 3H), 1.45-1.21 (m, 6H), 1.09-1.02 (m, 3H). MS (ESI) calc'd for $(C_{22}H_{30}N_9O_2)$ $[M+H]^+$ 452; found 452.

TABLE 4

| Compound | Structure | IUPAC Name | Exact Mass [M + H]+ |
| --- | --- | --- | --- |
| 4-1 | 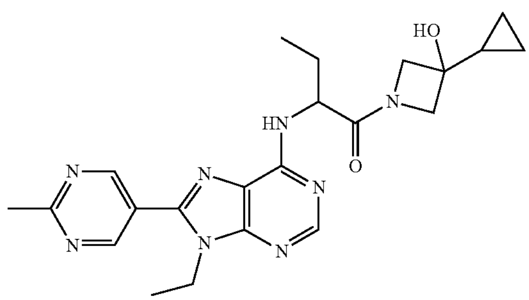 [SMILES: CCC(Nc1ncnc2c1nc(-c1cnc(C)nc1)n2CC)C(=O)N1CC(O)(C2CC2)C1] | (S or R)-3-cyclopropyl-1-(2-{[9-ethyl-8-(2-methylpyrimidin-5-yl)-9H-purin-6-yl]amino}butanoyl)azetidin-3-ol | Calc'd 437; found 437 |
| 4-2 | 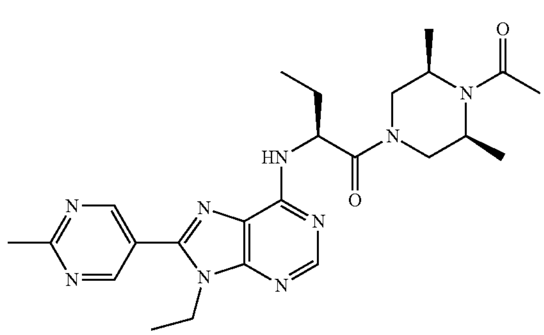 [SMILES: CC[C@H](Nc1ncnc2c1nc(-c1cnc(C)nc1)n2CC)C(=O)N1C[C@@H](C)N(C(C)=O)[C@@H](C)C1] | N-[(1S)-1-{[cis-4-acetyl-3,5-dimethylpiperazin-1-yl]carbonyl}propyl]-9-ethyl-8-(2-methylpyrimidin-5-yl)-9H-purin-6-amine | Calc'd 480; found 480 |

TABLE 4-continued

| Compound | Structure | IUPAC Name | Exact Mass [M + H]+ |
|---|---|---|---|
| 4-3 | 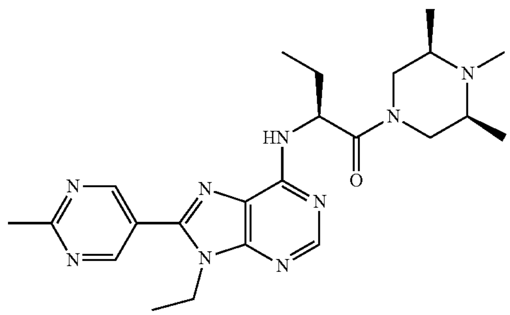 | 9-ethyl-8-(2-methylpyrimidin-5-yl)-N-[(1S)-1-{[cis-3,4,5-trimethylpiperazin-1-yl]carbonyl}propyl]-9H-purin-6-amine | Calc'd 452; found 452 |
| 4-4 | 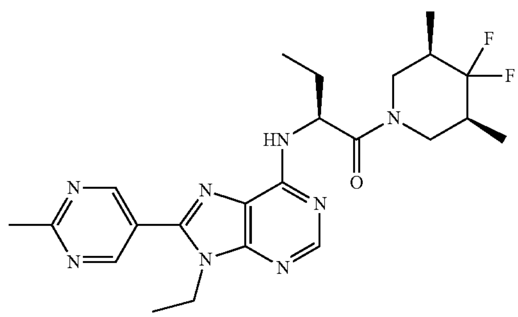 [SMILES: CC[C@H](Nc1ncnc2c1nc(-c1cnc(C)nc1)n2CC)C(=O)N1C[C@@H](C)C(F)(F)[C@@H](C)C1] | N-[(1S)-1-{[cis-4,4-difluoro-3,5-dimethylpiperidin-1-yl]carbonyl}propyl]-9-ethyl-8-(2-methylpyrimidin-5-yl)-9H-purin-6-amine | Calc'd 473; found 473 |
| 4-5 | 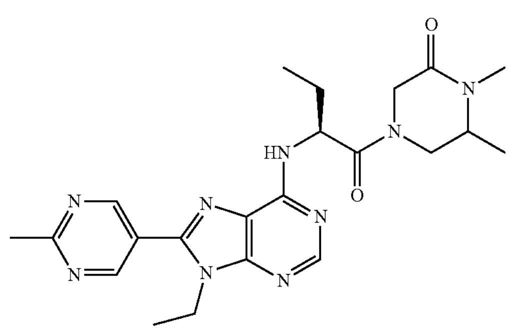 | (S or R)-4-[(2S)-2-{[9-ethyl-8-(2-methylpyrimidin-5-yl)-9H-purin-6-yl]amino}butanoyl]-1,6-dimethylpiperazin-2-one | Calc'd 452; found 452 |
| 4-6 | 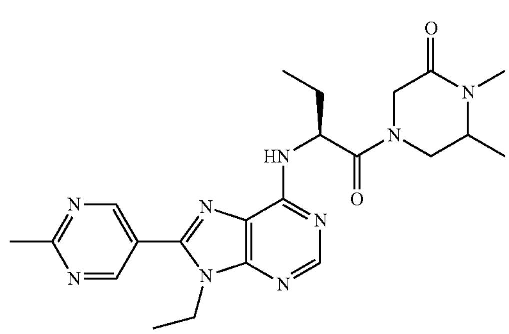 | (S or R)-4-[(2S)-2-{[9-ethyl-8-(2-methylpyrimidin-5-yl)-9H-purin-6-yl]amino}butanoyl]-1,6-dimethylpiperazin-2-one | Calc'd 452; found 452 |

TABLE 4-continued

| Compound | Structure | IUPAC Name | Exact Mass [M + H]+ |
|---|---|---|---|
| 4-7 | 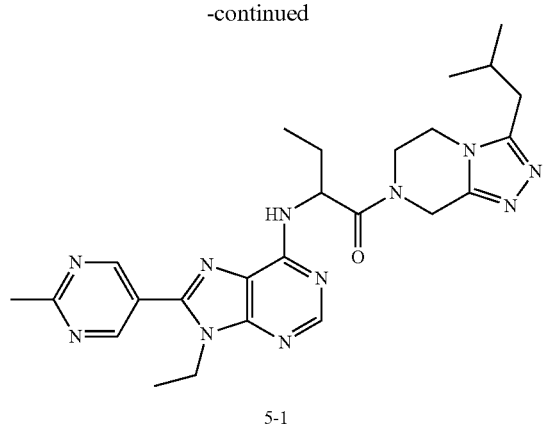 | 4-[(2S)-2-{[9-ethyl-8-(2-methylpyrimidin-5-yl)-9H-purin-6-yl]amino}butanoyl]-6,6-dimethylpiperazin-2-one | Calc'd 452; found 452 |

Compound Examples of Table 5

Example V-1 Preparation of Compound 5-1

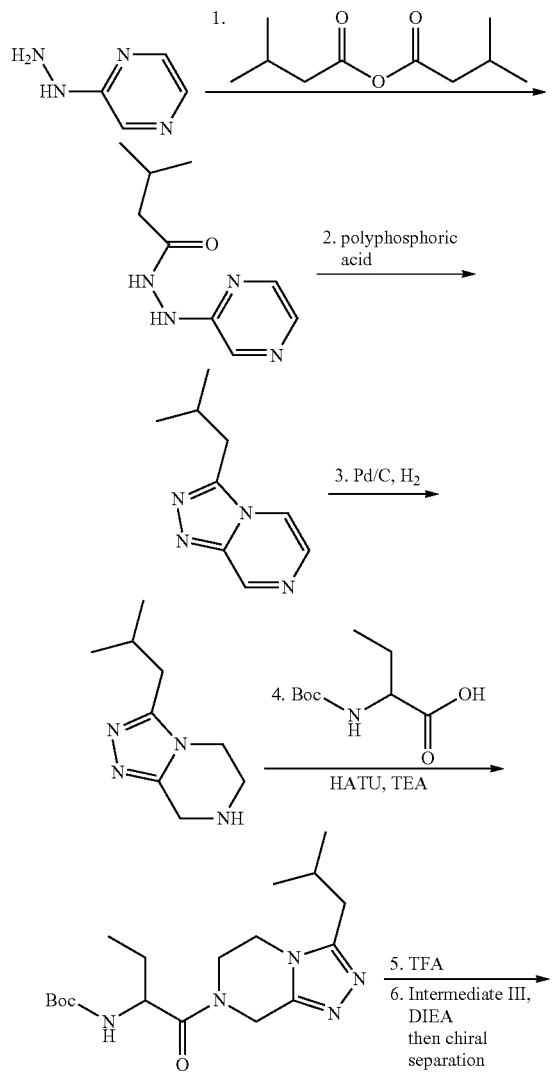

5-1

Step 1: 3-Methyl-N'-(pyrazin-2-yl)butanehydrazide

To a solution of 2-hydrazinylpyrazine (3.00 g, 27.2 mmol) in ethanol (30 mL) was added 3-methylbutanoic anhydride (7.61 g, 40.9 mmol) at 0° C., and the resulting mixture was stirred for 1 h at 0° C. The reaction solution was then quenched b the addition of water (100 mL), and the resulting mixture was extracted with EtOAc (3×100 mL). The combined organic layers were washed with brine (100 mL), dried over anhydrous $Na_2SO_4$, and filtered. The filtrate was concentrated under reduced pressure to afford 3-methyl-N-(pyrazin-2-yl)butanehydrazide, which was used in the next step without further purification. MS (ESI) Calc'd for ($C_9H_{15}N_4O$) [M+H]+ 195; found 195.

Step 2: 3-Isobutyl-[1,2,4]triazolo[4,3-a]pyrazine

A solution of 3-methyl-N-(pyrazin-2-yl)butanehydrazide (4.00 g, 20.6 mmol) in polyphosphoric acid (50 mL) was stirred for 12 h at 100° C. After cooling to RT, the reaction mixture was poured into ice water (100 mL). The PH value of the resulting solution was adjusted to 8 via the addition of $NaHCO_3$ powder. The resulting mixture was extracted with EtOAc (3×100 mL), and the combined organic layers were washed with brine (100 mL), dried over anhydrous $Na_2SO_4$, and filtered. The filtrate was concentrated under reduced pressure, and the residue obtained was purified by column chromatography (silica gel, eluting with a gradient of 0-70%

EtOAc in hexanes) to afford 3-isobutyl-[1,2,4]triazolo[4,3-a]pyrazine. MS (ESI) Calc'd for ($C_9H_{13}N_4$) [M+H]+ 177; found 177.

Step 3: 3-Isobutyl-5,6,7,8-tetrahydro-[1,2,4]triazolo[4,3-a]pyrazine

To a solution of 3-isobutyl-[1,2,4]triazolo[4,3-a]pyrazine (0.70 g, 4.0 mmol) in MeOH (5 mL) was added Pd/C (10% by weight, 0.42 g, 4.0 mmol) at RT. The solution was evacuated and backfilled with hydrogen gas (×3), after which it was stirred for 40 min at RT under an atmosphere of hydrogen (1 atm). The reaction mixture was then filtered, and the filtrate was concentrated under reduced pressure to afford 3-isobutyl-5,6,7,8-tetrahydro-[1,2,4]triazolo[4,3-a]pyrazine which was used in the next step without further purification. MS (ESI) Calc'd for ($C_9H_{17}N_4$) [M+H]+ 181; found 181.

Step 4: tert-Butyl(1-(3-isobutyl-5,6-dihydro-[1,2,4]triazolo[4,3-a]pyrazin-7(8H)-yl)-1-oxobutan-2-yl)carbamate To a solution of 2-((tert-butoxycarbonyl)amino)butanoic acid (124 mg, 0.61 mmol) in DMF (3 mL) were added HATU (0.23 g, 0.61 mmol), TEA (0.12 mL, 0.83 mmol), and 3-isobutyl-5,6,7,8-tetrahydro-[1,2,4]triazolo[4,3-a]pyrazine (100 mg, 0.55 mmol), and the resulting mixture was stirred at RT for 1 h. The reaction mixture was then quenched by the addition of water (20 mL), and the resulting mixture was extracted with EtOAc (3×20 mL). The combined organic layers were washed with brine (20 mL), dried over anhydrous $Na_2SO_4$, and filtered. The filtrate was concentrated under reduced pressure to afford tert-butyl (1-(3-isobutyl-5,6-dihydro-[1,2,4]triazolo[4,3-a]pyrazin-7(8H)-yl)-1-oxobutan-2-yl)carbamate, which was used in the next step without further purification. MS (ESI) Calc'd for ($C_{18}H_{32}N_5O_3$) [M+H]+ 366; found 366.

Step 5: 2-Amino-1-(3-isobutyl-5,6-dihydro-[1,2,4]triazolo[4,3-a]pyrazin-7(8H)-yl) butan-1-one 2,2,2-trifluoroacetate To a solution of tert-butyl (1-(3-isobutyl-5,6-dihydro-[1,2,4]triazolo[4,3-a]pyrazin-7(8H)-yl)-1-oxobutan-2-yl)carbamate (100 mg, 0.27 mmol) in DCM (2 mL), was added TFA (2 mL), and the resulting mixture was stirred RT for 30 min. The reaction solution was then concentrated under reduced pressure to afford 2-amino-1-(3-isobutyl-5,6-dihydro-[1,2,4]triazolo[4,3-a]pyrazin-7(8H)-yl)butan-1-one 2,2,2-trifluoroacetate, which was used in the next step without further purification. MS (ESI) Calc'd for ($C_{13}H_{24}N_5O$) [M+H]+ 266. found 266.

Step 6: Compound 5-1

To a solution of 2-amino-1-(3-isobutyl-5,6-dihydro-[1,2,4]triazolo[4,3-a] pyrazin-7(8H)-yl)butan-1-one 2,2,2-trifluoroacetate (100 mg, 0.26 mmol) in IPA (2 mL), were added DIEA (0.14 mL, 0.79 mmol) and Intermediate III (43.4 mg, 0.16 mmol) at RT. The resulting mixture was stirred at 85° C. for 36 h. The reaction mixture was then cooled to RT and was quenched by the addition of water (5 mL). The resulting mixture was extracted with EtOAc (3×10 mL), and the combined organic layers were washed with brine (10 mL), dried over anhydrous $Na_2SO_4$, and filtered. The filtrate was concentrated under reduced pressure, and the residue obtained was purified by column chromatography (silica gel, eluting with a gradient of 0-10% MeOH in DCM) to afford the racemic product. Chiral resolution of the racemic mixture was achieved via preparative chiral HPLC (Column: Chiralpak IB 2×25 cm, 5 um; eluting with 50% ethanol in hexanes (isocratic); Flow rate: 17 mL/min) to afford 5-1 (slower eluting enantiomer, 14 min): 1H NMR (300 MHz, DMSO-$d_6$, 353K) δ: 9.08 (s, 2H), 8.22 (s, 1H), 7.50-7.45 (m, 1H), 5.50-5.45 (min, 1H), 4.95-4.85 (min, 2H), 4.40-4.25 (m, 2H), 4.10-3.80 (min, 4H), 2.75 (s, 3H), 2.55-2.50 (m, 2H), 2.10-1.95 (m, 1H), 1.90-1.75 (m, 2H), 1.35-1.15 (m, 3H), 0.98-0.80 (m, 9H). MS (ESI) Calc'd for ($C_{25}H_{34}N_{11}O$) [M+H]+ 504; found 504.

Example V-2 Preparation of Compound 5-2

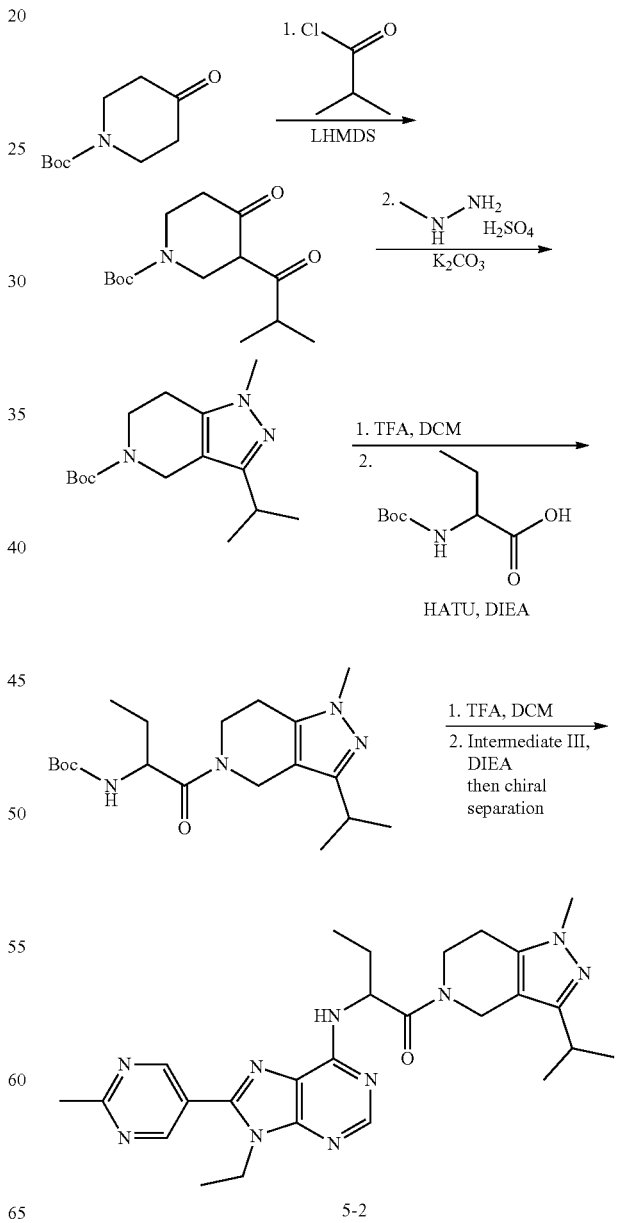

5-2

Step 1: tert-Butyl-3-isobutyl-4-oxopiperidine-1-carboxylate

To a solution of tert-butyl 4-oxopiperidine-1-carboxylate (2.00 g, 10.0 mmol) in THF (30 mL) was added LHMDS (1 M in THF, 13.0 mL, 13.0 mmol) at −20° C. under atmosphere of nitrogen. The resulting solution was stirred for 15 min at −20° C., followed by addition of isobutyryl chloride (1.39 g, 13.0 mmol) at −20° C. The resulting mixture was allowed to come to RT and was stirred for 1 h. The reaction mixture was then quenched by the addition of saturated aqueous $NH_4Cl$ (50 mL), and the resulting mixture was extracted with EtOAc (3×50 mL). The combined organic layers were washed with brine (30 mL), dried over anhydrous $Na_2SO_4$, and filtered. The filtrate was concentrated under reduced pressure to afford tert-butyl 3-isobutyryl-4-oxopiperidine-1-carboxylate, which was used in the next step without further purification. MS (ESI) Calc'd for ($C_{14}H_{24}NO_4$) [M+H]$^+$ 270; found 270.

Step 2: tert-Butyl-3-isopropyl-1-methyl-6, 7-dihydro-1H-pyrazolo[4,3-c]pyridine-5(4H)-carboxylate To a solution of tert-butyl 3-isobutyryl-4-oxopiperidine-1-carboxylate (1.30 g, 3.86 mmol) in EtOH (20 mL) were added $K_2CO_3$ (1.60 g, 11.6 mmol) and methylhydrazine sulfate (0.83 g, 5.8 mmol) at RT. The resulting mixture was stirred for 2 h at 85° C., after which it was cooled to RT and quenched by the addition of water (50 mL). The resulting mixture was extracted with EtOAc (3×50 mL), and the combined organic layers were washed with brine (30 mL), dried over anhydrous $Na_2SO_4$, and filtered. The filtrate was concentrated under reduced pressure, and the residue obtained was purified by column chromatography (silica gel, eluting with a gradient of 0-80% EtOAc in hexanes) to afford tert-butyl 3-isopropyl-1-methyl-6,7-dihydro-1H-pyrazolo[4,3-c]pyridine-5(4H)-carboxylate. MS (ESI) Calc'd for ($C_{15}H_{26}N_3O_2$) [M+H]$^+$ 280; found 280.

Step 3: 3-Isopropyl-1-methyl-4,5,6,7-tetrahydro-1H-pyrazolo[4,3-c]pyridine 2,2,2-trifluoroacetate To a solution of tert-butyl 3-isopropyl-1-methyl-6,7-dihydro-1H-pyrazolo[4,3-c]pyridine-5(4H)-carboxylate (0.50 g, 1.8 mmol) in DCM (5 mL), was added TFA (5 mL), and the resulting mixture was allowed to stir at RT for 30 min. The reaction solution was then concentrated under reduced pressure to afford 3-isopropyl-1-methyl-4,5,6,7-tetrahydro-H-pyrazolo[4,3-c]pyridine 2,2,2-trifluoroacetate, which was used in the next step without further purification. MS (ESI) Calc'd for ($C_{10}H_{18}N_3$) [M+H]$^+$ 180; found 180.

Step 4: tert-Butyl 1-(3-isopropyl-1-methyl-6,7-dihydro-1H-pyrazolo[4,3-c]pyridine-5(4H)-yl)-1-oxobutan-2-ylcarbamate To a solution of 2-((tert-butoxycarbonyl)amino)butanoic acid (0.28 g, 1.36 mmol) in DMF (20 mL) were added HATU (0.67 g, 1.77 mmol) and TEA (0.89 g, 8.85 mmol), 3-isopropyl-1-methyl-4,5,6,7-tetrahydro-1H-pyrazolo[4,3-c]pyridine 2,2,2-trifluoroacetate (0.40 g, 1.36 mmol), and the resulting mixture was stirred for 1 h at RT. The reaction mixture was then quenched by the addition of water (50 mL), and the resulting mixture was extracted with EtOAc (3×30 mL). The combined organic layers were washed with brine (20 mL), dried over anhydrous $Na_2SO_4$, and filtered. The filtrate was concentrated under reduced pressure, and the residue obtained was purified by column chromatography (silica gel, eluting with a gradient 0-50% EtOAc in hexanes) to afford tert-butyl (1-(3-isopropyl-1-methyl-6,7-dihydro-1H-pyrazolo[4,3-c]pyridin-5(4H)-yl)-1-oxobutan-2-yl)carbamate. MS (ESI) Calc'd for ($C_{19}H_{33}N_4O_3$) [M+H]$^+$ 365; found 365.

Step 5: 2-Amino-1-(3-isopropyl-1-methyl-6,7-dihydro-1H-pyrazolo[4,3-c]pyridine-5(4H)-yl)butan-1-one 2,2,2-trifluoroacetate To a solution of tert-butyl (1-(3-isopropyl-1-methyl-6,7-dihydro-1H-pyrazolo[4,3-c]pyridin-5(4H)-yl)-1-oxobutan-2-yl)carbamate (0.50 g, 1.23 mmol) in DCM (5 mL), was added TFA (5 mL), and the resulting solution was stirred for 1 h at RT. The reaction mixture was then concentrated under reduced pressure to afford 2-amino-1-(3-isopropyl-1-methyl-6,7-dihydro-1H-pyrazolo[4,3-c]pyridin-5(4H)-yl)butan-1-one 2,2,2-trifluoroacetate, which was used in the next step without further purification. MS (ESI) Calc'd for ($C_{14}H_{25}N_4O$) [M+H]$^+$ 265; found 265.

Step 6: Compound 5-2

To a solution of 2-amino-1-(3-isopropyl-1-methyl-6,7-dihydro-1H-pyrazolo[4,3-c]pyridin-5(4H)-yl)butan-1-one 2,2,2-trifluoroacetate (50.0 mg, 0.13 mmol) in IPA (3 mL), were added DIEA (0.12 mL, 0.66 mmol) and Intermediate III (36.3 mg, 0.13 mmol) at RT. The resulting mixture was stirred for 12 h at 80° C. After cooling to RT, the reaction mixture was then quenched by the addition of water (20 mL). The resulting mixture was extracted with EtOAc (3×10 mL), and the combined organic layers were washed with brine (10 mL), dried over anhydrous $Na_2SO_4$, and filtered. The filtrate was concentrated under reduced pressure, and the residue obtained was purified by column chromatography (silica gel, eluting with a gradient of 0-100% EtOAc in hexanes) to afford the racemic product. Chiral resolution of the racemic mixture was achieved via preparative, chiral HPLC (Column: Chiralpak IB 2×25 cm, 5 um; eluting with 30% ethanol in hexanes; Flow rate: 20 mL/min) to afford compound 5-2 (slower eluting enantiomer, 11 min): $^1$H NMR (300 MHz, DMSO-d6, 353 K): δ: 9.10 (s, 2H), 8.28 (s, 1H), 7.21-7.18 (m, 1H), 5.53 (brs, 1H), 4.64-4.40 (m, 2H), 4.30 (q, J=7.2 Hz, 2H), 3.93-3.77 (m, 2H), 3.59 (s, 3H), 2.89-2.70 (m, 6H), 1.98-1.81 (m, 2H), 1.35 (t, J=7.2 Hz, 3H), 1.22-1.10 (m, 6H), 0.99-0.90 (m, 3H). MS (ESI) Calc'd for ($C_{26}H_{35}N_{10}O$) [M+H]$^+$ 503; found 503.

TABLE 5

| Compound | Structure | IUPAC Name | Exact Mass [M + H]+ |
|---|---|---|---|
| 5-1 | 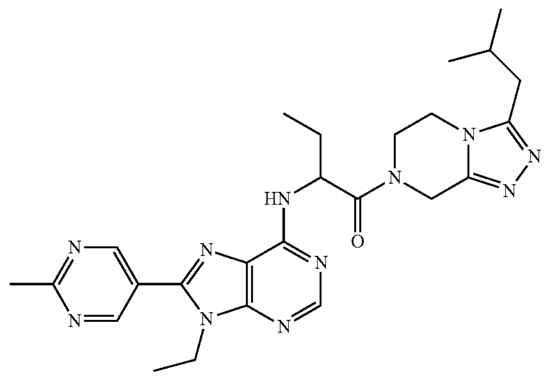 [SMILES: CCC(Nc1ncnc2c1nc(-c1cnc(C)nc1)n2CC)C(=O)N1CCn2c(CC(C)C)nnc2C1] | (S or R)-9-ethyl-N-(1-{[3-(2-methylpropyl)-5,6-dihydro[1,2,4]triazolo[4,3-a]pyrazin-7(8H)-yl]carbonyl}propyl)-8-(2-methylpyrimidin-5-yl)-9H-purin-6-amine | Calc'd 504; found 504 |
| 5-2 | 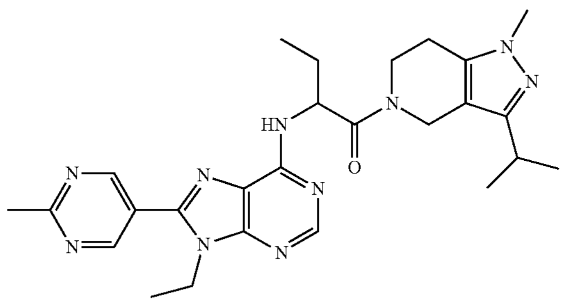 [SMILES: CCC(Nc1ncnc2c1nc(-c1cnc(C)nc1)n2CC)C(=O)N1CCc2c(c(C(C)C)nn2C)C1] | (S or R)-9-ethyl-N-(1-{[1-methyl-3-(1-methylethyl)-1,4,6,7-tetrahydro-5H-pyrazolo[4,3-c]pyridin-5-yl]carbonyl}propyl)-8-(2-methylpyrimidin-5-yl)-9H-purin-6-amine | Calc'd 503; found 503 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes.

This assay was developed and further optimized from a kit produced by Upstate (Millipore catalog #33-047) and has been configured for HTS (high throughput screening) and SAR screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (Eu)-labeled anti-GST, GST-tagged GRP1-PH domain, biotin-PIP3 and streptavidin conjugated APC. The native PIP3 produced by PI3-Kinase activity disrupts in a competitive manner the biotin-PIP3 from the PH domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM ATP in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (alpha 14-602, beta 14-603, gamma 14-558 and delta 14-604 from Upstate; Millipore), dithiothreitol (Sigma, D-5545), Adenosine-5' triphosphate (InVitrogen, Cat#AS001A), native PIP3 (PI(3,4,5)P3, diC8, H+, CELLSIGNALS, INC. Cat #907) DMSO (Sigma, 472301).

PI3Kinase Reaction Buffer is prepared by dilution the stock 1:4 with de-ionized water. DTT, PIP2 and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptor. Plates are incubated at RT for 15 minutes. Reactions are initiated by addition of 1.25 ul of 2× substrate solution (PIP2 and ATP in 1× reaction buffer) using BioRaptor. Plates are incubated in humidified chamber at RT for one hour. Reactions are quenched by addition of 0.625 uL of stop solution to all wells using the BioRaptor. The quenched reactions are then processed to detect product formation by adding 0.625 uL of Detection Solution to all wells using the BioRaptor (Detection mix C, Detection Mix A, and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio−CtrlB)/(CtrlA−CtrlB) where CtrlA=PI3Kinase reaction+known reference inhibitor and CtrlB=PI3K+DMSO. An $IC_{50}$ was then calculated fitting the % inhibition data to the equation: % inhibition=min+(Max−min)/1+([inhibitor]/IC50)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound Number | Form Screened | PI3Kdelta IC50 (nM) | Selectivity versus PI3Kalpha |
|---|---|---|---|
| 1-1 | Neutral | 320 | >10 |
| 1-2 | Neutral | 240 | >10 |
| 1-3 | Neutral | 26 | >10 |
| 1-4 | Neutral | 4.0 | >10 |
| 1-5 | Neutral | 9.0 | >10 |
| 1-6 | Neutral | 5.2 | >10 |
| 1-7 | Neutral | 24 | >10 |
| 1-8 | Neutral | 6.5 | >10 |
| 2-1 | Neutral | 15 | >10 |
| 2-2 | Neutral | 59 | >10 |
| 2-3 | Neutral | 590 | >10 |
| 2-4 | Neutral | 99 | >10 |
| 2-5 | Neutral | 230 | >10 |
| 2-6 | Neutral | 6.1 | >10 |
| 2-7 | Neutral | 2.8 | >10 |
| 2-8 | Neutral | 31 | >10 |
| 2-9 | Neutral | 23 | >10 |
| 2-10 | Neutral | 62 | >10 |
| 2-11 | Neutral | 60 | >10 |
| 2-12 | Neutral | 11 | >10 |
| 2-13 | Neutral | 26 | >10 |
| 2-14 | Neutral | 7.0 | >10 |
| 2-15 | Neutral | 37 | >10 |
| 2-16 | Neutral | 112 | >10 |
| 2-17 | Neutral | 74 | >10 |
| 2-18 | Neutral | 31 | >10 |
| 2-19 | Neutral | 50 | >10 |
| 2-20 | Neutral | 14 | >10 |
| 2-21 | Neutral | 14 | >10 |
| 2-22 | Neutral | 17 | >10 |
| 2-23 | Neutral | 9.3 | >10 |
| 2-24 | Neutral | 27 | >10 |
| 2-25 | Neutral | 21 | >10 |
| 2-26 | Neutral | 32 | >10 |
| 2-27 | Neutral | 11 | >10 |
| 2-28 | Neutral | 22 | >10 |
| 2-29 | Neutral | 11 | >10 |
| 2-30 | Neutral | 19 | >10 |
| 2-31 | Neutral | 37 | >10 |
| 2-32 | Neutral | 83 | >10 |
| 2-33 | Neutral | 9.8 | >10 |
| 2-34 | Neutral | 12 | >10 |
| 2-35 | Neutral | 39 | >10 |
| 2-36 | Neutral | 9.1 | >10 |
| 2-37 | Neutral | 64 | >10 |
| 2-38 | Neutral | 10 | >10 |
| 2-39 | Neutral | 12 | >10 |
| 2-40 | Neutral | 4.1 | >10 |
| 2-41 | Neutral | 110 | >10 |
| 2-42 | Neutral | 5.3 | >10 |
| 2-43 | Neutral | 87 | >10 |
| 2-44 | Neutral | 140 | >10 |
| 2-45 | Neutral | 26 | >10 |
| 2-46 | Neutral | 27 | >10 |
| 2-47 | Neutral | 12 | >10 |
| 2-48 | Neutral | 55 | >10 |
| 2-49 | Neutral | 4.1 | >10 |
| 2-50 | Neutral | 8.7 | >10 |
| 2-51 | Neutral | 420 | >10 |
| 2-52 | Neutral | 3.7 | >10 |
| 2-53 | Neutral | 37 | >10 |
| 2-54 | Neutral | 250 | >10 |
| 2-55 | Neutral | 20 | >10 |
| 2-56 | Neutral | 610 | >10 |
| 2-57 | Neutral | 24 | >10 |
| 2-58 | Neutral | 290 | >10 |
| 2-59 | Neutral | 63 | >10 |
| 2-60 | Neutral | 29 | >10 |
| 2-61 | Neutral | 93 | >10 |
| 2-62 | Neutral | 100 | >10 |
| 3-1 | Neutral | 17 | >10 |
| 3-2 | Neutral | 6.2 | >10 |
| 3-3 | Neutral | 8.6 | >10 |
| 3-4 | Neutral | 5.2 | >10 |
| 4-1 | Neutral | 30 | >10 |
| 4-2 | Neutral | 21 | >10 |
| 4-3 | Neutral | 5.5 | >10 |
| 4-4 | Neutral | 4.8 | >10 |
| 4-5 | Neutral | 6.1 | >10 |
| 4-6 | Neutral | 26 | >10 |
| 4-7 | Neutral | 19 | >10 |
| 5-1 | Neutral | 38 | >10 |
| 5-2 | Neutral | 39 | >10 |

What is claimed is:

1. A compound of formula I or a pharmaceutically acceptable salt or stereoisomer thereof:

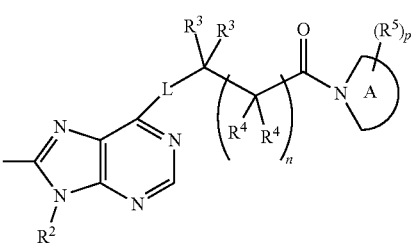

L is O or NH;
$R^1$ is $C_{1-6}$alkyl, $C_{1-6}$haloalkyl, or a 5- to 6-membered heteroaryl ring, wherein the 5- to 6-membered heteroaryl ring is substituted by 0, 1, 2, or 3 groups independently selected from fluoro, chloro, $C_{1-6}$alkyl, and $C_{1-6}$haloalkyl;

$R^2$ is hydrogen or $C_{1-6}$alkyl;

$R^3$ is each independently selected from hydrogen, $C_{1-10}$alkyl, aryl$C_{0-10}$ alkyl, $C_{3-8}$ cycloalkyl$C_{0-10}$ alkyl, —($C_{1-10}$ alkyl)OH, $C_{1-10}$ alkoxy$C_{0-10}$ alkyl, and ($C_{0-10}$ alkyl)$_{1-2}$ amino$C_{0-10}$ alkyl, and $C_{0-10}$ alkylcarbonylamino$C_{0-10}$ alkyl, wherein two $R^3$ may join together with the carbon to which they are attached to form a 3- to 8-membered ring;

$R^4$ is each independently selected from hydrogen and $C_{1-10}$alkyl, wherein two $R^4$ may join together with the carbon to which they are attached to form a 3- to 8-membered ring;

n is 0, 1, 2, 3, or 4;

p is 0, 1, 2, 3, or 4;

$R^5$ is each independently selected from hydrogen, halogen, $C_{1-10}$alkyl, oxo, cyano, $C_{1-10}$ alkoxy$C_{0-10}$ alkyl (oxy)$_{0-1}$, $C_{1-6}$alkylcarbonyl, $C_{1-6}$haloalkyl, cycloalkyl$C_{0-10}$ alkyl, and —($C_{1-10}$ alkyl)OH;

wherein the group

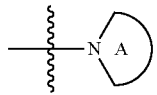

is selected from
1) $C_{3-12}$heterocycloalkyl having at least one nitrogen, wherein the $C_{3-12}$heterocycloalkyl is bonded to the illustrated carbonyl via a nitrogen atom; and
2) spiroheterocyclic ring having at least one nitrogen, wherein the spiroheterocyclic ring is bonded to the illustrated carbonyl via a nitrogen atom.

2. The compound according to claim 1, wherein $R^1$ is selected from difluoromethyl, trifluoromethyl, difluoroethyl, 2,2,2-trifluoroethyl, pyrimidinyl, pyridinyl, and pyrazolyl, wherein pyrimidinyl, pyridinyl and pyrazolyl are substituted by 0, 1, 2, or 3 groups independently selected from fluoro, chloro, $C_{1-6}$alkyl, and $C_{1-6}$haloalkyl.

3. The compound according to claim 2, wherein $R^2$ is selected from methyl, ethyl, propyl, butyl and tert-butyl.

4. The compound according to claim 3, wherein L is O or NH.

5. The compound according to claim 3, wherein L is NH.

6. The compound according to claim 1, wherein $R^3$ is each independently selected from hydrogen, $C_{1-10}$alkyl, aryl$C_{0-10}$ alkyl, $C_{3-8}$ cycloalkyl, —($C_{1-10}$ alkyl)OH, $C_{1-10}$ alkoxy$C_{0-10}$ alkyl, and ($C_{0-10}$ alkyl)$_{1-2}$ amino$C_{0-10}$ alkyl, and wherein two $R^3$ substituents join together with the carbon to which they are attached to form a cyclopropyl or cyclopentyl ring.

7. The compound according to claim 6, wherein $R^3$ is each independently selected from hydrogen, ethyl, methyl, methylphenyl, cyclopropyl, acetamide, 2,2-dimethylpropyl, phenyl, isobutyl, propyl, methoxymethyl, hydroxymethyl, cyclopentyl, isopropyl, hydroxyisopropyl, dimethylaminoamethyl, 2-methoxypropyl, and methoxyeth-1yl.

8. The compound according to claim 6, wherein two $R^3$ substituents join together with the carbon to which they are attached to form a cyclopropyl ring.

9. The compound according to claim 6, wherein $R^4$ is each independently hydrogen, methyl or ethyl, or two $R^4$ join together with the carbon to which they are attached to form a cyclopropyl ring.

10. The compound according to claim 1, wherein the group

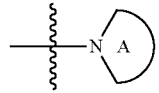

is selected from morpholinyl, piperidinyl, piperazinyl, azetidinyl, thiomorpholinyl, azepanyl, hexahydro-5H-thieno[2,3-c]pyrrolyl, hexahydropyrrolo[1,2-a]pyrazin-2(1H)-yl, pyrrolidinyl, octahydroisoquinolinyl, octahydroisoquinolin-2yl, (cis)-octahydroisoquinolin-2yl, 2-azaspiro[3.4]oct-2yl, thiazolidinyl (1,3-thiazolidinyl), 1,4-oxazepanyl, 8-oxa-5-azaspiro[3.5]non-5yl; 4-oxa-7-azaspiro[2.5]oct-7-yl, 5,6-dihydro[1,2,4]triazolo[4,3-a]pyrazin-7(8H)-yl, 1,4,6,7-tetrahydro-5H-pyrazolo[4,3-c]pyridin-5-yl, and 2-oxa-5-azabicyclo[2.2.1]hept-5yl.

11. The compound according to claim 7, wherein n is 0, 1 or 2; and p is 0, 1, 2 or 3.

12. The compound according to claim 11, wherein each $R^5$ is each independently selected from hydroxy, isopropyl, isobutyl, methylcarbonyl, hydrogen, methyl, fluoro, oxo, methoxy, methoxyethyloxy, difluoromethyl, cyano, cyclopropyl, isopropyl, methoxymethyl, and hydroxymethyl.

13. The compound or a pharmaceutically acceptable salt, wherein the compound is selected from
8-(1-ethyl-5-methyl-1H-pyrazol-4-yl)-9-methyl-6-[1-(morpholin-4-ylcarbonyl)propoxy]-9H-purine;
R-8-(1-ethyl-5-methyl-1H-pyrazol-4-yl)-9-methyl-6-[1-(morpholin-4-ylcarbonyl)propoxy]-9H-purine;
S-8-(1-ethyl-5-methyl-1H-pyrazol-4-yl)-9-methyl-6-[1-(morpholin-4-ylcarbonyl)propoxy]-9H-purine;
8-(1-ethyl-5-methyl-1H-pyrazol-4-yl)-9-methyl-6-[1-(piperidin-1-ylcarbonyl)propoxy]-9H-purine;
R-8-(1-ethyl-5-methyl-1H-pyrazol-4-yl)-9-methyl-6-[1-(piperidin-1-ylcarbonyl)propoxy]-9H-purine;
S-8-(1-ethyl-5-methyl-1H-pyrazol-4-yl)-9-methyl-6-[1-(piperidin-1-ylcarbonyl)propoxy]-9H-purine;
N-[1-(azetidin-1-ylcarbonyl)propyl]-8-(1-ethyl-5-methyl-1H-pyrazol-4-yl)-9-methyl-9H-purin-6-amine;
R—N-[1-(azetidin-1-ylcarbonyl)propyl]-8-(1-ethyl-5-methyl-1H-pyrazol-4-yl)-9-methyl-9H-purin-6-amine;
S—N-[1-(azetidin-1-ylcarbonyl)propyl]-8-(1-ethyl-5-methyl-1H-pyrazol-4-yl)-9-methyl-9H-purin-6-amine;
N-(1-{[2,6-dimethylmorpholin-4-yl]carbonyl}propyl)-8-(1-ethyl-5-methyl-1H-pyrazol-4-yl)-9-methyl-9H-purin-6-amine;
R—N-(1-{[(cis)-2,6-dimethylmorpholin-4-yl]carbonyl}propyl)-8-(1-ethyl-5-methyl-1H-pyrazol-4-yl)-9-methyl-9H-purin-6-amine;
S—N-(1-{[(cis)-2,6-dimethylmorpholin-4-yl]carbonyl}propyl)-8-(1-ethyl-5-methyl-1H-pyrazol-4-yl)-9-methyl-9H-purin-6-amine;
N-{1-[(4,4-difluoropiperidin-1-yl)carbonyl]propyl}-8-(1-ethyl-5-methyl-1H-pyrazol-4-yl)-9-methyl-9H-purin-6-amine;
R—N-{1-[(4,4-difluoropiperidin-1-yl)carbonyl]propyl}-8-(1-ethyl-5-methyl-1H-pyrazol-4-yl)-9-methyl-9H-purin-6-amine;
S—N-{1-[(4,4-difluoropiperidin-1-yl)carbonyl]propyl}-8-(1-ethyl-5-methyl-1H-pyrazol-4-yl)-9-methyl-9H-purin-6-amine;
8-(1-ethyl-5-methyl-1H-pyrazol-4-yl)-9-methyl-N-[1-(morpholin-4-ylcarbonyl)propyl]-9H-purin-6-amine;

R-8-(1-ethyl-5-methyl-1H-pyrazol-4-yl)-9-methyl-N-[1-(morpholin-4-ylcarbonyl)propyl]-9H-purin-6-amine;
S-8-(1-ethyl-5-methyl-1H-pyrazol-4-yl)-9-methyl-N-[1-(morpholin-4-ylcarbonyl)propyl]-9H-purin-6-amine;
8-(1-ethyl-5-methyl-1H-pyrazol-4-yl)-9-methyl-N-(1-methyl-2-morpholin-4-yl-2-oxoethyl)-9H-purin-6-amine;
R-8-(1-ethyl-5-methyl-1H-pyrazol-4-yl)-9-methyl-N-(1-methyl-2-morpholin-4-yl-2-oxoethyl)-9H-purin-6-amine;
S-8-(1-ethyl-5-methyl-1H-pyrazol-4-yl)-9-methyl-N-(1-methyl-2-morpholin-4-yl-2-oxoethyl)-9H-purin-6-amine;
9-ethyl-8-(2-methylpyrimidin-5-yl)-N-[1-(morpholin-4-ylcarbonyl)propyl]-9H-purin-6-amine;
R-9-ethyl-8-(2-methylpyrimidin-5-yl)-N-[1-(morpholin-4-ylcarbonyl)propyl]-9H-purin-6-amine;
S-9-ethyl-8-(2-methylpyrimidin-5-yl)-N-[1-(morpholin-4-ylcarbonyl)propyl]-9H-purin-6-amine;
N-[1-benzyl-2-morpholin-4-yl-2-oxoethyl]-8-(1-ethyl-5-methyl-1H-pyrazol-4-yl)-9-methyl-9H-purin-6-amine;
N-[(1R)-1-benzyl-2-morpholin-4-yl-2-oxoethyl]-8-(1-ethyl-5-methyl-1H-pyrazol-4-yl)-9-methyl-9H-purin-6-amine;
N-[(1S)-1-benzyl-2-morpholin-4-yl-2-oxoethyl]-8-(1-ethyl-5-methyl-1H-pyrazol-4-yl)-9-methyl-9H-purin-6-amine;
N-{1-[(4,4-difluoropiperidin-1-yl)carbonyl]cyclopropyl}-9-ethyl-8-(2-methylpyrimidin-5-yl)-9H-purin-6-amine;
8-(difluoromethyl)-N-[1-{[2,6-dimethylmorpholin-4-yl]carbonyl}propyl]-9-ethyl-9H-purin-6-amine;
8-(difluoromethyl)-N-[(1S)-1-{[(cis)-2,6-dimethylmorpholin-4-yl]carbonyl}propyl]-9-ethyl-9H-purin-6-amine;
8-(difluoromethyl)-N-[(1R)-1-{[(cis)-2,6-dimethylmorpholin-4-yl]carbonyl}propyl]-9-ethyl-9H-purin-6-amine;
8-(difluoromethyl)-N-{2-[2,6-dimethylmorpholin-4-yl]-1-methyl-2-oxoethyl-2-oxoethyl}-9-ethyl-9H-purin-6-amine;
8-(difluoromethyl)-N-{(1S)-2-[(cis)-2,6-dimethylmorpholin-4-yl]-1-methyl-2-oxoethyl}-9-ethyl-9H-purin-6-amine;
8-(difluoromethyl)-N-{(1R)-2-[(cis)-2,6-dimethylmorpholin-4-yl]-1-methyl-2-oxoethyl}-9-ethyl-9H-purin-6-amine;
N-[1-{[2,6-dimethylmorpholin-4-yl]carbonyl}propyl]-9-ethyl-8-(2-methylpyrimidin-5-yl)-9H-purin-6-amine;
N-[(1S)-1-{[(cis)-2,6-dimethylmorpholin-4-yl]carbonyl}propyl]-9-ethyl-8-(2-methylpyrimidin-5-yl)-9H-purin-6-amine;
N-[(1R)-1-{[(cis)-2,6-dimethylmorpholin-4-yl]carbonyl}propyl]-9-ethyl-8-(2-methylpyrimidin-5-yl)-9H-purin-6-amine;
N-[1-{[2,6-dimethylmorpholin-4-yl]carbonyl}propyl]-9-ethyl-8-[6-(trifluoromethyl)pyridin-3-yl]-9H-purin-6-amine;
N-[(1S)-1-{[(cis)-2,6-dimethylmorpholin-4-yl]carbonyl}propyl]-9-ethyl-8-[6-(trifluoromethyl)pyridin-3-yl]-9H-purin-6-amine;
N-[(1R)-1-{[(cis)-2,6-dimethylmorpholin-4-yl]carbonyl}propyl]-9-ethyl-8-[6-(trifluoromethyl)pyridin-3-yl]-9H-purin-6-amine;
N-{1-[(1,1-dioxidothiomorpholin-4-yl)carbonyl]propyl}-9-ethyl-8-(2-methylpyrimidin-5-yl)-9H-purin-6-amine;
N-{(1S)-1-[(1,1-dioxidothiomorpholin-4-yl)carbonyl]propyl}-9-ethyl-8-(2-methylpyrimidin-5-yl)-9H-purin-6-amine;
N-{(1R)-1-[(1,1-dioxidothiomorpholin-4-yl)carbonyl]propyl}-9-ethyl-8-(2-methylpyrimidin-5-yl)-9H-purin-6-amine;
9-ethyl-N-{1-[(4-methoxyazepan-1-yl)carbonyl]propyl}-8-(2-methylpyrimidin-5-yl)-9H-purin-6-amine;
9-ethyl-N-{(1S)-1-[(4-methoxyazepan-1-yl)carbonyl]propyl}-8-((R)-2-methylpyrimidin-5-yl)-9H-purin-6-amine;
9-ethyl-N-{(1S)-1-[(4-methoxyazepan-1-yl)carbonyl]propyl}-8-((S)-2-methylpyrimidin-5-yl)-9H-purin-6-amine;
9-ethyl-N-{(1R)-1-[(4-methoxyazepan-1-yl)carbonyl]propyl}-8-((R)-2-methylpyrimidin-5-yl)-9H-purin-6-amine;
9-ethyl-N-{(1R)-1-[(4-methoxyazepan-1-yl)carbonyl]propyl}-8-((S)-2-methylpyrimidin-5-yl)-9H-purin-6-amine;
9-ethyl-N-[1-{[4-(2-methoxyethoxy)piperidin-1-yl]carbonyl}propyl]-8-(2-methylpyrimidin-5-yl)-9H-purin-6-amine;
9-ethyl-N-[(1S)-1-{[4-(2-methoxyethoxy)piperidin-1-yl]carbonyl}propyl]-8-(2-methylpyrimidin-5-yl)-9H-purin-6-amine;
9-ethyl-N-[(1R)-1-{[4-(2-methoxyethoxy)piperidin-1-yl]carbonyl}propyl]-8-(2-methylpyrimidin-5-yl)-9H-purin-6-amine;
N-[1-{[3-(difluoromethyl)azetidin-1-yl]carbonyl}propyl]-9-ethyl-8-(2-methylpyrimidin-5-yl)-9H-purin-6-amine;
N-[(1S)-1-{[3-(difluoromethyl)azetidin-1-yl]carbonyl)}propyl]-9-ethyl-8-(2-methylpyrimidin-5-yl)-9H-purin-6-amine;
N-[(1R)-1-{[3-(difluoromethyl)azetidin-1-yl]carbonyl}propyl]-9-ethyl-8-(2-methylpyrimidin-5-yl)-9H-purin-6-amine;
N-{1-[(3,3-difluoropiperidin-1-yl)carbonyl]propyl}-9-ethyl-8-(2-methylpyrimidin-5-yl)-9H-purin-6-amine;
N-{(1S)-1-[(3,3-difluoropiperidin-1-yl)carbonyl]propyl}-9-ethyl-8-(2-methylpyrimidin-5-yl)-9H-purin-6-amine;
N-{(1R)-1-[(3,3-difluoropiperidin-1-yl)carbonyl]propyl}-9-ethyl-8-(2-methylpyrimidin-5-yl)-9H-purin-6-amine;
1-[2-{[9-ethyl-8-(2-methylpyrimidin-5-yl)-9H-purin-6-yl]amino}butanoyl]piperidine-4-carbonitrile;
1-[(2S)-2-{[9-ethyl-8-(2-methylpyrimidin-5-yl)-9H-purin-6-yl]amino}butanoyl]piperidine-4-carbonitrile;
1-[(2R)-2-{[9-ethyl-8-(2-methylpyrimidin-5-yl)-9H-purin-6-yl]amino}butanoyl]piperidine-4-carbonitrile;
N-{1-[(1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aR, 6aR-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aR, 6aS-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aS, 6aR-1,1-dioxidohexahydro-5H-thieno[2,3-c]pyrrol-5-yl)carbonyl]propyl}-9-ethyl-8-(2-methylpyrimidin-5-yl)-9H-purin-6-amine;
N-{(1S)-1-[((3aS, 6aS-1,1-dioxidohexahydro-5H-thieno[2,3-c]pyrrol-5-yl)carbonyl]propyl}-9-ethyl-8-(2-methylpyrimidin-5-yl)-9H-purin-6-amine;

N-{(1R)-1-[((3aS, 6aR)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

N-{(1R)-1-[((3aR, 6aS)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

N-{(1R)-1-[((3aS, 6aS)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

N-{(1R)-1-[((3aR, 6aR)-1,1-dioxidohexahydro-5H-thieno[2,3-c]pyrrol-5-yl)carbonyl]propyl}-9-ethyl-8-(2-methylpyrimidin-5-yl)-9H-purin-6-amine;

9-ethyl-N-[1-{[3-fluoropyrrolidin-1-yl]carbonyl}propyl]-8-(2-methylpyrimidin-5-yl)-9H-purin-6-amine;

9-ethyl-N-[(1S)-1-{[(3S)-3-fluoropyrrolidin-1-yl]carbonyl}propyl]-8-(2-methylpyrimidin-5-yl)-9H-purin-6-amine;

9-ethyl-N-[(1S)-1-{[(3R)-3-fluoropyrrolidin-1-yl]carbonyl}propyl]-8-(2-methylpyrimidin-5-yl)-9H-purin-6-amine;

9-ethyl-N-[(1R)-1-{[(3S)-3-fluoropyrrolidin-1-yl]carbonyl}propyl]-8-(2-methylpyrimidin-5-yl)-9H-purin-6-amine;

9-ethyl-N-[(1R)-1-{[(3R)-3-fluoropyrrolidin-1-yl]carbonyl}propyl]-8-(2-methylpyrimidin-5-yl)-9H-purin-6-amine;

9-ethyl-N-{1-[(3-methoxyazetidin-1-yl)carbonyl]propyl}-8-(2-methylpyrimidin-5-yl)-9H-purin-6-amine;

9-ethyl-N-{(1S)-1-[(3-methoxyazetidin-1-yl)carbonyl]propyl}-8-(2-methylpyrimidin-5-yl)-9H-purin-6-amine;

9-ethyl-N-{(1R)-1-[(3-methoxyazetidin-1-yl)carbonyl]propyl}-8-(2-methylpyrimidin-5-yl)-9H-purin-6-amine;

9-ethyl-8-(2-methylpyrimidin-5-yl)-N-{1-[(3-methylpyrrolidin-1-yl)carbonyl]propyl}-9H-purin-6-amine;

9-ethyl-8-(2-methylpyrimidin-5-yl)-N-{(1S)-1-[(S-3-methylpyrrolidin-1-yl)carbonyl]propyl}-9H-purin-6-amine;

9-ethyl-8-(2-methylpyrimidin-5-yl)-N-{(1S)-1-[(R-3-methylpyrrolidin-1-yl)carbonyl]propyl}-9H-purin-6-amine;

9-ethyl-8-(2-methylpyrimidin-5-yl)-N-{(1R)-1-[(S-3-methylpyrrolidin-1-yl)carbonyl]propyl}-9H-purin-6-amine;

9-ethyl-8-(2-methylpyrimidin-5-yl)-N-{(1R)-1-[(R-3-methylpyrrolidin-1-yl)carbonyl]propyl}-9H-purin-6-amine;

9-ethyl-N-{1-[(3-methoxypyrrolidin-1-yl)carbonyl]propyl}-8-(2-methylpyrimidin-5-yl)-9H-purin-6-amine;

9-ethyl-N-{(1S)-1-[(S-3-methoxypyrrolidin-1-yl)carbonyl]propyl}-8-(2-methylpyrimidin-5-yl)-9H-purin-6-amine;

9-ethyl-N-{(1S)-1-[(R-3-methoxypyrrolidin-1-yl)carbonyl]propyl}-8-(2-methylpyrimidin-5-yl)-9H-purin-6-amine;

9-ethyl-N-{(1R)-1-[(S-3-methoxypyrrolidin-1-yl)carbonyl]propyl}-8-(2-methylpyrimidin-5-yl)-9H-purin-6-amine;

9-ethyl-N-{(1R)-1-[(R-3-methoxypyrrolidin-1-yl)carbonyl]propyl}-8-(2-methylpyrimidin-5-yl)-9H-purin-6-amine;

9-ethyl-8-(2-methylpyrimidin-5-yl)-N-{1-[(cis)-octahydroisoquinolin-2(1H)-ylcarbonyl]propyl}-9H-purin-6-amine;

9-ethyl-8-(2-methylpyrimidin-5-yl)-N-{(1R)-1-[(cis)-octahydroisoquinolin-2(1H)-ylcarbonyl]propyl}-9H-purin-6-amine;

9-ethyl-8-(2-methylpyrimidin-5-yl)-N-{(1S)-1-[(cis)-octahydroisoquinolin-2(1H)-ylcarbonyl]propyl}-9H-purin-6-amine;

N-[1-(2-azaspiro[3.4]oct-2-ylcarbonyl)propyl]-9-ethyl-8-(2-methylpyrimidin-5-yl)-9H-purin-6-amine;

N-[(1R)-1-(2-azaspiro[3.4]oct-2-ylcarbonyl)propyl]-9-ethyl-8-(2-methylpyrimidin-5-yl)-9H-purin-6-amine;

N-[(1S)-1-(2-azaspiro[3.4]oct-2-ylcarbonyl)propyl]-9-ethyl-8-(2-methylpyrimidin-5-yl)-9H-purin-6-amine;

N-{1-[(2-cyclopropylpyrrolidin-1-yl)carbonyl]propyl}-9-ethyl-8-(2-methylpyrimidin-5-yl)-9H-purin-6-amine;

N-{(1S)-1-[(R-2-cyclopropylpyrrolidin-1-yl)carbonyl]propyl}-9-ethyl-8-(2-methylpyrimidin-5-yl)-9H-purin-6-amine;

N-{(1S)-1-[(S-2-cyclopropylpyrrolidin-1-yl)carbonyl]propyl}-9-ethyl-8-(2-methylpyrimidin-5-yl)-9H-purin-6-amine;

N-{(1R)-1-[(R-2-cyclopropylpyrrolidin-1-yl)carbonyl]propyl}-9-ethyl-8-(2-methylpyrimidin-5-yl)-9H-purin-6-amine;

N-{(1R)-1-[(S-2-cyclopropylpyrrolidin-1-yl)carbonyl]propyl}-9-ethyl-8-(2-methylpyrimidin-5-yl)-9H-purin-6-amine;

9-ethyl-N-{1-[(3-methylpiperidin-1-yl)carbonyl]propyl}-8-(2-methylpyrimidin-5-yl)-9H-purin-6-amine;

9-ethyl-N-{(1S)-1-[((R)-3-methylpiperidin-1-yl)carbonyl]propyl}-8-(2-methylpyrimidin-5-yl)-9H-purin-6-amine;

9-ethyl-N-{(1S)-1-[((S)-3-methylpiperidin-1-yl)carbonyl]propyl}-8-(2-methylpyrimidin-5-yl)-9H-purin-6-amine;

9-ethyl-N-{(1R)-1-[(R-3-methylpiperidin-1-yl)carbonyl]propyl}-8-(2-methylpyrimidin-5-yl)-9H-purin-6-amine;

9-ethyl-N-{(1R)-1-[(R-3-methylpiperidin-1-yl)carbonyl]propyl}-8-(2-methylpyrimidin-5-yl)-9H-purin-6-amine;

9-ethyl-8-(2-methylpyrimidin-5-yl)-N-{1-[(-2-methyl-1,3-thiazolidin-3-yl)carbonyl]propyl}-9H-purin-6-amine;

9-ethyl-8-(2-methylpyrimidin-5-yl)-N-{(1S)-1-[(S-2-methyl-1,3-thiazolidin-3-yl)carbonyl]propyl}-9H-purin-6-amine;

9-ethyl-8-(2-methylpyrimidin-5-yl)-N-{(1S)-1-[(R-2-methyl-1,3-thiazolidin-3-yl)carbonyl]propyl}-9H-purin-6-amine;

9-ethyl-8-(2-methylpyrimidin-5-yl)-N-{(1R)-1-[(S-2-methyl-1,3-thiazolidin-3-yl)carbonyl]propyl}-9H-purin-6-amine;

9-ethyl-8-(2-methylpyrimidin-5-yl)-N-{(1R)-1-[(R-2-methyl-1,3-thiazolidin-3-yl)carbonyl]propyl}-9H-purin-6-amine;

9-ethyl-8-(2-methylpyrimidin-5-yl)-N-[1-(1,4-oxazepan-4-ylcarbonyl)propyl]-9H-purin-6-amine;

9-ethyl-8-(2-methylpyrimidin-5-yl)-N-[(1S)-1-(1,4-oxazepan-4-ylcarbonyl)propyl]-9H-purin-6-amine;

9-ethyl-8-(2-methylpyrimidin-5-yl)-N-[(1R)-1-(1,4-oxazepan-4-ylcarbonyl)propyl]-9H-purin-6-amine;

9-ethyl-N-[1-{[3-methylmorpholin-4-yl]carbonyl}propyl]-8-(2-methylpyrimidin-5-yl)-9H-purin-6-amine;

9-ethyl-N-[(1S)-1-{[(3S)-3-methylmorpholin-4-yl]carbonyl}propyl]-8-(2-methylpyrimidin-5-yl)-9H-purin-6-amine;

9-ethyl-N-[(1S)-1-{[(3R)-3-methylmorpholin-4-yl]carbonyl}propyl]-8-(2-methylpyrimidin-5-yl)-9H-purin-6-amine;

9-ethyl-N-[(1R)-1-{[(3S)-3-methylmorpholin-4-yl]carbonyl}propyl]-8-(2-methylpyrimidin-5-yl)-9H-purin-6-amine 9-ethyl-N-[(1R)-1-{[(3R)-3-methylmorpholin-4-yl]carbonyl}propyl]-8-(2-methylpyrimidin-5-yl)-9H-purin-6-amine;

9-ethyl-8-(2-methylpyrimidin-5-yl)-N-[1-(8-oxa-5-azaspiro[3.5]non-5-ylcarbonyl)propyl]-9H-purin-6-amine;

9-ethyl-8-(2-methylpyrimidin-5-yl)-N-[(1S)-1-(8-oxa-5-azaspiro[3.5]non-5-ylcarbonyl)propyl]-9H-purin-6-amine;

9-ethyl-8-(2-methylpyrimidin-5-yl)-N-[(1R)-1-(8-oxa-5-azaspiro[3.5]non-5-ylcarbonyl)propyl]-9H-purin-6-amine;

N-{1-[(2-cyclopropylmorpholin-4-yl)carbonyl]propyl}-9-ethyl-8-(2-methylpyrimidin-5-yl)-9H-purin-6-amine;

N-{(1S)-1-[(S-2-cyclopropylmorpholin-4-yl)carbonyl]propyl}-9-ethyl-8-(2-methylpyrimidin-5-yl)-9H-purin-6-amine;

N-{(1S)-1-[(R-2-cyclopropylmorpholin-4-yl)carbonyl]propyl}-9-ethyl-8-(2-methylpyrimidin-5-yl)-9H-purin-6-amine;

N-{(1R)-1-[(R-2-cyclopropylmorpholin-4-yl)carbonyl]propyl}-9-ethyl-8-(2-methylpyrimidin-5-yl)-9H-purin-6-amine;

N-{(1R)-1-[(S-2-cyclopropylmorpholin-4-yl)carbonyl]propyl}-9-ethyl-8-(2-methylpyrimidin-5-yl)-9H-purin-6-amine;

9-ethyl-8-(2-methylpyrimidin-5-yl)-N-[1-(4-oxa-7-azaspiro[2.5]oct-7-ylcarbonyl)propyl]-9H-purin-6-amine;

9-ethyl-8-(2-methylpyrimidin-5-yl)-N-[(1S)-1-(4-oxa-7-azaspiro[2.5]oct-7-ylcarbonyl)propyl]-9H-purin-6-amine;

9-ethyl-8-(2-methylpyrimidin-5-yl)-N-[(1R)-1-(4-oxa-7-azaspiro[2.5]oct-7-ylcarbonyl)propyl]-9H-purin-6-amine;

N-{1-[(3-cyclopropylmorpholin-4-yl)carbonyl]propyl}-9-ethyl-8-(2-methylpyrimidin-5-yl)-9H-purin-6-amine;

N-{(1S)-1-[(S-3-cyclopropylmorpholin-4-yl)carbonyl]propyl}-9-ethyl-8-(2-methylpyrimidin-5-yl)-9H-purin-6-amine;

N-{(1S)-1-[(R-3-cyclopropylmorpholin-4-yl)carbonyl]propyl}-9-ethyl-8-(2-methylpyrimidin-5-yl)-9H-purin-6-amine;

N-{(1R)-1-[(S-3-cyclopropylmorpholin-4-yl)carbonyl]propyl}-9-ethyl-8-(2-methylpyrimidin-5-yl)-9H-purin-6-amine;

N-{(1R)-1-[(R-3-cyclopropylmorpholin-4-yl)carbonyl]propyl}-9-ethyl-8-(2-methylpyrimidin-5-yl)-9H-purin-6-amine;

9-ethyl-8-(2-methylpyrimidin-5-yl)-N-{1-[2-oxa-5-azabicyclo[2.2.1]hept-5-ylcarbonyl]propyl}-9H-purin-6-amine;

9-ethyl-8-(2-methylpyrimidin-5-yl)-N-{(1S)-1-[(1S,4S)-2-oxa-5-azabicyclo[2.2.1]hept-5-ylcarbonyl]propyl}-9H-purin-6-amine;

9-ethyl-8-(2-methylpyrimidin-5-yl)-N-{(1S)-1-[(1R,4R)-2-oxa-5-azabicyclo[2.2.1]hept-5-ylcarbonyl]propyl}-9H-purin-6-amine;

9-ethyl-8-(2-methylpyrimidin-5-yl)-N-{(1S)-1-[(1R,4S)-2-oxa-5-azabicyclo[2.2.1]hept-5-ylcarbonyl]propyl}-9H-purin-6-amine;

9-ethyl-8-(2-methylpyrimidin-5-yl)-N-{(1S)-1-[(1S,4R)-2-oxa-5-azabicyclo[2.2.1]hept-5-ylcarbonyl]propyl}-9H-purin-6-amine;

9-ethyl-8-(2-methylpyrimidin-5-yl)-N-{(1R)-1-[(1S,4S)-2-oxa-5-azabicyclo[2.2.1]hept-5-ylcarbonyl]propyl}-9H-purin-6-amine;

9-ethyl-8-(2-methylpyrimidin-5-yl)-N-{(1R)-1-[(1R,4R)-2-oxa-5-azabicyclo[2.2.1]hept-5-ylcarbonyl]propyl}-9H-purin-6-amine;

9-ethyl-8-(2-methylpyrimidin-5-yl)-N-{(1R)-1-[(1R,4S)-2-oxa-5-azabicyclo[2.2.1]hept-5-ylcarbonyl]propyl}-9H-purin-6-amine;

9-ethyl-8-(2-methylpyrimidin-5-yl)-N-{(1R)-1-[(1S,4R)-2-oxa-5-azabicyclo[2.2.1]hept-5-ylcarbonyl]propyl}-9H-purin-6-amine;

9-ethyl-N-[1-{[3-(1-methylethyl)morpholin-4-yl]carbonyl}propyl]-8-(2-methylpyrimidin-5-yl)-9H-purin-6-amine;

9-ethyl-N-[(1R)-1-{[3-(1-methylethyl)morpholin-4-yl]carbonyl}propyl]-8-(2-methylpyrimidin-5-yl)-9H-purin-6-amine;

9-ethyl-N-[(1S)-1-{[3-(1-methylethyl)morpholin-4-yl]carbonyl}propyl]-8-(2-methylpyrimidin-5-yl)-9H-purin-6-amine;

N-{1-[(2,2-dimethylmorpholin-4-yl)carbonyl]propyl}-9-ethyl-8-(2-methylpyrimidin-5-yl)-9H-purin-6-amine;

N-{(1R)-1-[(2,2-dimethylmorpholin-4-yl)carbonyl]propyl}-9-ethyl-8-(2-methylpyrimidin-5-yl)-9H-purin-6-amine;

N-{(1S)-1-[(2,2-dimethylmorpholin-4-yl)carbonyl]propyl}-9-ethyl-8-(2-methylpyrimidin-5-yl)-9H-purin-6-amine;

N-{1-[(3,3-dimethylmorpholin-4-yl)carbonyl]propyl}-9-ethyl-8-(2-methylpyrimidin-5-yl)-9H-purin-6-amine;

N-{(1S)-1-[(3,3-dimethylmorpholin-4-yl)carbonyl]propyl}-9-ethyl-8-(2-methylpyrimidin-5-yl)-9H-purin-6-amine;

N-{(1R)-1-[(3,3-dimethylmorpholin-4-yl)carbonyl]propyl}-9-ethyl-8-(2-methylpyrimidin-5-yl)-9H-purin-6-amine;

9-ethyl-N-[1-{[2-(methoxymethyl)morpholin-4-yl]carbonyl}propyl]-8-(2-methylpyrimidin-5-yl)-9H-purin-6-amine;

9-ethyl-N-[(1S)-1-{[2-(methoxymethyl)morpholin-4-yl]carbonyl}propyl]-8-(2-methylpyrimidin-5-yl)-9H-purin-6-amine;

9-ethyl-N-[(1R)-1-{[2-(methoxymethyl)morpholin-4-yl]carbonyl}propyl]-8-(2-methylpyrimidin-5-yl)-9H-purin-6-amine;

N-[1-{[2,6-dimethylmorpholin-4-yl]carbonyl}propyl]-9-ethyl-8-(2-methylpyrimidin-5-yl)-9H-purin-6-amine;

N-[(1S)-1-{[(trans)-2,6-dimethylmorpholin-4-yl]carbonyl}propyl]-9-ethyl-8-(2-methylpyrimidin-5-yl)-9H-purin-6-amine;

N-[(1R)-1-{[(trans)-2,6-dimethylmorpholin-4-yl]carbonyl}propyl]-9-ethyl-8-(2-methylpyrimidin-5-yl)-9H-purin-6-amine;

{4-[2-{[9-ethyl-8-(2-methylpyrimidin-5-yl)-9H-purin-6-yl]amino}butanoyl]-morpholin-3-yl}methanol;

{4-[(2S)-2-{[9-ethyl-8-(2-methylpyrimidin-5-yl)-9H-purin-6-yl]amino}butanoyl]-R-morpholin-3-yl}methanol;
{4-[(2S)-2-{[9-ethyl-8-(2-methylpyrimidin-5-yl)-9H-purin-6-yl]amino}butanoyl]-S-morpholin-3-yl}methanol;
{4-[(2R)-2-{[9-ethyl-8-(2-methylpyrimidin-5-yl)-9H-purin-6-yl]amino}butanoyl]-R-morpholin-3-yl}methanol;
{4-[(2R)-2-{[9-ethyl-8-(2-methylpyrimidin-5-yl)-9H-purin-6-yl]amino}butanoyl]-S-morpholin-3-yl}methanol;
9-ethyl-N-[1-(hexahydropyrrolo[1,2-a]pyrazin-2(1H)-ylcarbonyl)propyl]-8-(2-methylpyrimidin-5-yl)-9H-purin-6-amine;
9-ethyl-N-[(1R)-1-(S)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(R)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(S)-(hexahydropyrrolo[1,2-a]pyrazin-2(1H)-ylcarbonyl)propyl]-8-(2-methylpyrimidin-5-yl)-9H-purin-6-amine;
9-ethyl-N-[(1S)-1-(R)-(hexahydropyrrolo[1,2-a]pyrazin-2(1H)-ylcarbonyl)propyl]-8-(2-methylpyrimidin-5-yl)-9H-purin-6-amine;
N-{2-[2,6-dimethylmorpholin-4-yl]-1methy-2-oxoethyl}-9-ethyl-8-(2-methylpyrimidin-5-yl)-9H-purin-6-amine;
N-{(1S)-2-[(cis)-2,6-dimethylmorpholin-4-yl]-1-methyl-2-oxoethyl}-9-ethyl-8-(2-methylpyrimidin-5-yl)-9H-purin-6-amine;
N-{(1R)-2-[(cis)-2,6-dimethylmorpholin-4-yl]-1-methyl-2-oxoethyl}-9-ethyl-8-(2-methylpyrimidin-5-yl)-9H-purin-6-amine;
N-{1-cyclopropyl-2-[2,6-dimethylmorpholin-4-yl]-2-oxoethyl}-9-ethyl-8-(2-methylpyrimidin-5-yl)-9H-purin-6-amine;
N-{(1S)-1-cyclopropyl-2-[(cis)-2,6-dimethylmorpholin-4-yl]-2-oxoethyl}-9-ethyl-8-(2-methylpyrimidin-5-yl)-9H-purin-6-amine;
N-{(1R)-1-cyclopropyl-2-[(cis)-2,6-dimethylmorpholin-4-yl]-2-oxoethyl}-9-ethyl-8-(2-methylpyrimidin-5-yl)-9H-purin-6-amine;
4-[2,6-dimethylmorpholin-4-yl]-3-{[9-ethyl-8-(2-methylpyrimidin-5-yl)-9H-purin-6-yl]amino}-4-oxobutanamide;
(3 S)-4-[(cis)-2,6-dimethylmorpholin-4-yl]-3-{[9-ethyl-8-(2-methylpyrimidin-5-yl)-9H-purin-6-yl]amino}-4-oxobutanamide;
(3R)-4-[(cis)-2,6-dimethylmorpholin-4-yl]-3-{[9-ethyl-8-(2-methylpyrimidin-5-yl)-9H-purin-6-yl]amino}-4-oxobutanamide;
N-[1-{[2,6-dimethylmorpholin-4-yl]carbonyl}-2,2-dimethylpropyl]-9-ethyl-8-(2-methylpyrimidin-5-yl)-9H-purin-6-amine;
N-[(1S)-1-{[(cis)-2,6-dimethylmorpholin-4-yl]carbonyl}-2,2-dimethylpropyl]-9-ethyl-8-(2-methylpyrimidin-5-yl)-9H-purin-6-amine;
N-[(1R)-1-{[(cis)-2,6-dimethylmorpholin-4-yl]carbonyl}-2,2-dimethylpropyl]-9-ethyl-8-(2-methylpyrimidin-5-yl)-9H-purin-6-amine;
N-{2-[2,6-dimethylmorpholin-4-yl]-2-oxo-1-phenylethyl)}-9-ethyl-8-(2-methylpyrimidin-5-yl)-9H-purin-6-amine;
N-{(1S)-2-[(cis)-2,6-dimethylmorpholin-4-yl]-2-oxo-1-phenylethyl}-9-ethyl-8-(2-methylpyrimidin-5-yl)-9H-purin-6-amine;
N-{(1R)-2-[(cis)-2,6-dimethylmorpholin-4-yl]-2-oxo-1-phenylethyl}-9-ethyl-8-(2-methylpyrimidin-5-yl)-9H-purin-6-amine;
N-[1-{[2,6-dimethylmorpholin-4-yl]carbonyl}-3-methylbutyl]-9-ethyl-8-(2-methylpyrimidin-5-yl)-9H-purin-6-amine;
N-[(1S)-1-{[(cis)-2,6-dimethylmorpholin-4-yl]carbonyl}-3-methylbutyl]-9-ethyl-8-(2-methylpyrimidin-5-yl)-9H-purin-6-amine;
N-[(1R)-1-{[(cis)-2,6-dimethylmorpholin-4-yl]carbonyl}-3-methylbutyl]-9-ethyl-8-(2-methylpyrimidin-5-yl)-9H-purin-6-amine;
N-[1-{[2,6-dimethylmorpholin-4-yl]carbonyl}butyl]-9-ethyl-8-(2-methylpyrimidin-5-yl)-9H-purin-6-amine;
N-[(1S)-1-{[(cis)-2,6-dimethylmorpholin-4-yl]carbonyl}butyl]-9-ethyl-8-(2-methylpyrimidin-5-yl)-9H-purin-6-amine;
N-[(1R)-1-{[(cis)-2,6-dimethylmorpholin-4-yl]carbonyl}butyl]-9-ethyl-8-(2-methylpyrimidin-5-yl)-9H-purin-6-amine;
N-[2-[2,6-dimethylmorpholin-4-yl]-1-(methoxymethyl)-2-oxoethyl]-9-ethyl-8-(2-methylpyrimidin-5-yl)-9H-purin-6-amine;
N-[(1S)-2-[(cis)-2,6-dimethylmorpholin-4-yl]-1-(methoxymethyl)-2-oxoethyl]-9-ethyl-8-(2-methylpyrimidin-5-yl)-9H-purin-6-amine;
N-[(1R)-2-[(cis)-2,6-dimethylmorpholin-4-yl]-1-(methoxymethyl)-2-oxoethyl]-9-ethyl-8-(2-methylpyrimidin-5-yl)-9H-purin-6-amine;
3-[2,6-dimethylmorpholin-4-yl]-2-{[9-ethyl-8-(2-methylpyrimidin-5-yl)-9H-purin-6-yl]amino}-3-oxopropan-1-ol;
(2S)-3-[(cis)-2,6-dimethylmorpholin-4-yl]-2-{[9-ethyl-8-(2-methylpyrimidin-5-yl)-9H-purin-6-yl]amino}-3-oxopropan-1-ol;
(2R)-3-[(cis)-2,6-dimethylmorpholin-4-yl]-2-{[9-ethyl-8-(2-methylpyrimidin-5-yl)-9H-purin-6-yl]amino}-3-oxopropan-1-ol;
N-{1-cyclopentyl-2-[2,6-dimethylmorpholin-4-yl]-2-oxoethyl}-9-ethyl-8-(2-methylpyrimidin-5-yl)-9H-purin-6-amine;
N-{(1S)-1-cyclopentyl-2-[(cis)-2,6-dimethylmorpholin-4-yl]-2-oxoethyl}-9-ethyl-8-(2-methylpyrimidin-5-yl)-9H-purin-6-amine;
N-{(1R)-1-cyclopentyl-2-[(cis)-2,6-dimethylmorpholin-4-yl]-2-oxoethyl}-9-ethyl-8-(2-methylpyrimidin-5-yl)-9H-purin-6-amine;
N-[1-{[2,6-dimethylmorpholin-4-yl]carbonyl}-2-methylpropyl]-9-ethyl-8-(2-methylpyrimidin-5-yl)-9H-purin-6-amine;
N-[(1S)-1-{[(cis)-2,6-dimethylmorpholin-4-yl]carbonyl}-2-methylpropyl]-9-ethyl-8-(2-methylpyrimidin-5-yl)-9H-purin-6-amine;
N-[(1R)-1-{[(cis)-2,6-dimethylmorpholin-4-yl]carbonyl}-2-methylpropyl]-9-ethyl-8-(2-methylpyrimidin-5-yl)-9H-purin-6-amine;
4-[2,6-dimethylmorpholin-4-yl]-3-{[9-ethyl-8-(2-methylpyrimidin-5-yl)-9H-purin-6-yl]amino}-2-methyl-4-oxobutan-2-ol;
(3 S)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol;

(3R)-4-[(cis)-2,6-dimethylmorpholin-4-yl]-3-{[9-ethyl-8-(2-methylpyrimidin-5-yl)-9H-purin-6-yl]amino}-2-methyl-4-oxobutan-2-ol;

3-[2,6-dimethylmorpholin-4-yl]-N-2-[9-ethyl-8-(2-methylpyrimidin-5-yl)-9H-purin-6-yl]-N~1~,N~1~-dimethyl-3-oxopropane-1,2-diamine;

(2S)-3-[(cis)-2,6-dimethylmorpholin-4-yl]-N-2-[9-ethyl-8-(2-methylpyrimidin-5-yl)-9H-purin-6-yl]-N~1~,N~1~-dimethyl-3-oxopropane-1,2-diamine;

(2R)-3-[(cis)-2,6-dimethylmorpholin-4-yl]-N-2-[9-ethyl-8-(2-methylpyrimidin-5-yl)-9H-purin-6-yl]-N~1~,N~1~-dimethyl-3-oxopropane-1,2-diamine;

N-[1-{[2,6-dimethylmorpholin-4-yl]carbonyl}-2-methoxypropyl]-9-ethyl-8-(2-methylpyrimidin-5-yl)-9H-purin-6-amine;

N-[(1S,2R)-1-{[(cis)-2,6-dimethylmorpholin-4-yl]carbonyl}-2-methoxypropyl]-9-ethyl-8-(2-methylpyrimidin-5-yl)-9H-purin-6-amine;

N-[(1S,2S)-1-{[(cis)-2,6-dimethylmorpholin-4-yl]carbonyl}-2-methoxypropyl]-9-ethyl-8-(2-methylpyrimidin-5-yl)-9H-purin-6-amine;

N-[(1R,2R)-1-{[(cis)-2,6-dimethylmorpholin-4-yl]carbonyl}-2-methoxypropyl]-9-ethyl-8-(2-methylpyrimidin-5-yl)-9H-purin-6-amine;

N-[(1R,2S)-1-{[(cis)-2,6-dimethylmorpholin-4-yl]carbonyl}-2-methoxypropyl]-9-ethyl-8-(2-methylpyrimidin-5-yl)-9H-purin-6-amine;

N-{3-[2,6-dimethylmorpholin-4-yl]-1-methyl-3-oxopropyl}-9-ethyl-8-(2-methylpyrimidin-5-yl)-9H-purin-6-amine;

N-{(1S)-3-[(cis)-2,6-dimethylmorpholin-4-yl]-1-methyl-3-oxopropyl}-9-ethyl-8-(2-methylpyrimidin-5-yl)-9H-purin-6-amine;

N-{(1R)-3-[(cis)-2,6-dimethylmorpholin-4-yl]-1-methyl-3-oxopropyl}-9-ethyl-8-(2-methylpyrimidin-5-yl)-9H-purin-6-amine;

N-{3-[2,6-dimethylmorpholin-4-yl]-2-methyl-3-oxopropyl}-9-ethyl-8-(2-methylpyrimidin-5-yl)-9H-purin-6-amine;

N-{(2R)-3-[(cis)-2,6-dimethylmorpholin-4-yl]-2-methyl-3-oxopropyl}-9-ethyl-8-(2-methylpyrimidin-5-yl)-9H-purin-6-amine;

N-{(2S)-3-[(cis)-2,6-dimethylmorpholin-4-yl]-2-methyl-3-oxopropyl}-9-ethyl-8-(2-methylpyrimidin-5-yl)-9H-purin-6-amine;

N-{3-[2,6-dimethylmorpholin-4-yl]-3-oxo-1-phenylpropyl}-9-ethyl-8-(2-methylpyrimidin-5-yl)-9H-purin-6-amine;

N-{(1R)-3-[(cis)-2,6-dimethylmorpholin-4-yl]-3-oxo-1-phenylpropyl}-9-ethyl-8-(2-methylpyrimidin-5-yl)-9H-purin-6-amine;

N-{(1S)-3-[(cis)-2,6-dimethylmorpholin-4-yl]-3-oxo-1-phenylpropyl}-9-ethyl-8-(2-methylpyrimidin-5-yl)-9H-purin-6-amine;

N-[(1-{[(cis)-2,6-dimethylmorpholin-4-yl]carbonyl}cyclopropyl)methyl]-9-ethyl-8-(2-methylpyrimidin-5-yl)-9H-purin-6-amine;

N-[3-[2,6-dimethylmorpholin-4-yl]-1-(1-methylethyl)-3-oxopropyl]-9-ethyl-8-(2-methylpyrimidin-5-yl)-9H-purin-6-amine;

N-[3-[(cis)-2,6-dimethylmorpholin-4-yl]-1-(1-methylethyl)-3-oxopropyl]-9-ethyl-8-(2-methylpyrimidin-5-yl)-9H-purin-6-amine;

N-[(1R)-3-[(cis)-2,6-dimethylmorpholin-4-yl]-1-(1-methylethyl)-3-oxopropyl]-9-ethyl-8-(2-methylpyrimidin-5-yl)-9H-purin-6-amine;

N-[(1S)-3-[(cis)-2,6-dimethylmorpholin-4-yl]-1-(1-methylethyl)-3-oxopropyl]-9-ethyl-8-(2-methylpyrimidin-5-yl)-9H-purin-6-amine;

9-ethyl-N-[1-methyl-3-oxo-3-pyrrolidin-1-ylpropyl]-8-(2-methylpyrimidin-5-yl)-9H-purin-6-amine;

9-ethyl-N-[(1S)-1-methyl-3-oxo-3-pyrrolidin-1-ylpropyl]-8-(2-methylpyrimidin-5-yl)-9H-purin-6-amine, 9-ethyl-N-[(1R)-1-methyl-3-oxo-3-pyrrolidin-1-ylpropyl]-8-(2-methylpyrimidin-5-yl)-9H-purin-6-amine;

9-ethyl-N-[2-methyl-3-oxo-3-pyrrolidin-1-ylpropyl]-8-(2-methylpyrimidin-5-yl)-9H-purin-6-amine;

9-ethyl-N-[(2R)-2-methyl-3-oxo-3-pyrrolidin-1-ylpropyl]-8-(2-methylpyrimidin-5-yl)-9H-purin-6-amine;

9-ethyl-N-[(2S)-2-methyl-3-oxo-3-pyrrolidin-1-ylpropyl]-8-(2-methylpyrimidin-5-yl)-9H-purin-6-amine;

9-ethyl-8-(2-methylpyrimidin-5-yl)-N-{[1-(pyrrolidin-1-ylcarbonyl)cyclopropyl]methyl}-9H-purin-6-amine;

9-ethyl-N-[1-(1-methylethyl)-3-oxo-3-pyrrolidin-1-ylpropyl]-8-(2-methylpyrimidin-5-yl)-9H-purin-6-amine;

9-ethyl-N-[(1R)-1-(1-methylethyl)-3-oxo-3-pyrrolidin-1-ylpropyl]-8-(2-methylpyrimidin-5-yl)-9H-purin-6-amine;

9-ethyl-N-[(1S)-1-(1-methylethyl)-3-oxo-3-pyrrolidin-1-ylpropyl]-8-(2-methylpyrimidin-5-yl)-9H-purin-6-amine;

N-[1-{[2,6-dimethylmorpholin-4-yl]carbonyl}propyl]-3-ethyl-2-(2-methylpyrimidin-5-yl)-3H-imidazo[4,5-b]pyridin-7-amine;

N-[(1S)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine;

N-[(1R)-1-{[(cis)-2,6-dimethylmorpholin-4-yl]carbonyl}propyl]-3-ethyl-2-(2-methylpyrimidin-5-yl)-3H-imidazo[4,5-b]pyridin-7-amine;

N-[1-{[2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[(1S)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[(1R)-1-{[(cis)-2,6-dimethylmorpholin-4-yl]carbonyl}propyl]-3-ethyl-2-[6-(trifluoromethyl)pyridin-3-yl]-3H-imidazo[4,5-b]pyridin-7-amine;

N-[1-{[2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2S)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1S,2S)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-[(1R,2R)-1-{[(cis)-2,6-dimethylmorpholin-4-yl]carbonyl}-2-methoxypropyl]-3-ethyl-2-(2-methylpyrimidin-5-yl)-3H-imidazo[4,5-b]pyridin-7-amine;

N-{1-cyclopropyl-2-[2,6-dimethylmorpholin-4-yl]-2-oxoethyl}-3-ethyl-2-(2-methylpyrimidin-5-yl)-3H-imidazo[4,5-b]pyridin-7-amine;

N-{(R)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine;

N—{(S)-1-cyclopropyl-2-[(cis)-2,6-dimethylmorpholin-4-yl]-2-oxoethyl}-3-ethyl-2-(2-methylpyrimidin-5-yl)-3H-imidazo[4,5-b]pyridin-7-amine;

3-cyclopropyl-1-(2-{[9-ethyl-8-(2-methylpyrimidin-5-yl)-9H-purin-6-yl]amino}butanoyl)azetidin-3-ol;

(S)-3-cyclopropyl-1-(2-{[9-ethyl-8-(2-methylpyrimidin-5-yl)-9H-purin-6-yl]amino}butanoyl)azetidin-3-ol;

(R)-3-cyclopropyl-1-(2-{[9-ethyl-8-(2-methylpyrimidin-5-yl)-9H-purin-6-yl]amino}butanoyl)azetidin-3-ol;

N-[1-{[4-acetyl-3,5-dimethylpiperazin-1-yl]carbonyl}propyl]-9-ethyl-8-(2-methylpyrimidin-5-yl)-9H-purin-6-amine;

N-[(1S)-1-{[cis-4-acetyl-3,5-dimethylpiperazin-1-yl]carbonyl}propyl]-9-ethyl-8-(2-methylpyrimidin-5-yl)-9H-purin-6-amine;

N-[(1R)-1-{[cis-4-acetyl-3,5-dimethylpiperazin-1-yl]carbonyl}propyl]-9-ethyl-8-(2-methylpyrimidin-5-yl)-9H-purin-6-amine;

9-ethyl-8-(2-methylpyrimidin-5-yl)-N-[1-{[3,4,5-trimethylpiperazin-1-yl]carbonyl}propyl]-9H-purin-6-amine;

9-ethyl-8-(2-methylpyrimidin-5-yl)-N-[(1S)-1-{[cis-3,4,5-trimethylpiperazin-1-yl]carbonyl}propyl]-9H-purin-6-amine;

9-ethyl-8-(2-methylpyrimidin-5-yl)-N-[(1R)-1-{[cis-3,4,5-trimethylpiperazin-1-yl]carbonyl}propyl]-9H-purin-6-amine;

N-[1-{[4,4-difluoro-3,5-dimethylpiperidin-1-yl]carbonyl)}propyl]-9-ethyl-8-(2-methylpyrimidin-5-yl)-9H-purin-6-amine;

N-[(1S)-1-{[cis-4,4-difluoro-3,5-dimethylpiperidin-1-yl]carbonyl}propyl]-9-ethyl-8-(2-methylpyrimidin-5-yl)-9H-purin-6-amine;

N-[(1R)-1-{[cis-4,4-difluoro-3,5-dimethylpiperidin-1-yl]carbonyl}propyl]-9-ethyl-8-(2-methylpyrimidin-5-yl)-9H-purin-6-amine;

4-[2-{[9-ethyl-8-(2-methylpyrimidin-5-yl)-9H-purin-6-yl]amino}butanoyl]-1,6-dimethylpiperazin-2-one;

(S)-4-[(2S)-2-{[9-ethyl-8-(2-methylpyrimidin-5-yl)-9H-purin-6-yl]amino}butanoyl]-1,6-dimethylpiperazin-2-one;

(R)-4-[(2S)-2-{[9-ethyl-8-(2-methylpyrimidin-5-yl)-9H-purin-6-yl]amino}butanoyl]-1,6-dimethylpiperazin-2-one;

(S)-4-[(2R)-2-{[9-ethyl-8-(2-methylpyrimidin-5-yl)-9H-purin-6-yl]amino}butanoyl]-1,6-dimethylpiperazin-2-one;

(R)-4-[(2R)-2-{[9-ethyl-8-(2-methylpyrimidin-5-yl)-9H-purin-6-yl]amino}butanoyl]-1,6-dimethylpiperazin-2-one;

4-[(2-{[9-ethyl-8-(2-methylpyrimidin-5-yl)-9H-purin-6-yl]amino}butanoyl]-6,6-dimethylpiperazin-2-one;

4-[(2S)-2-{[9-ethyl-8-(2-methylpyrimidin-5-yl)-9H-purin-6-yl]amino}butanoyl]-6,6-dimethylpiperazin-2-one;

4-[(2R)-2-{[9-ethyl-8-(2-methylpyrimidin-5-yl)-9H-purin-6-yl]amino}butanoyl]-6,6-dimethylpiperazin-2-one;

9-ethyl-N-(1-{[3-(2-methylpropyl)-5,6-dihydro[1,2,4]triazolo[4,3-a]pyrazin-7(8H)-yl]carbonyl}propyl)-8-(2-methylpyrimidin-5-yl)-9H-purin-6-amine;

(S)-9-ethyl-N-(1-{[1-methyl-3-(1-methylethyl)-1,4,6,7-tetrahydro-5H-pyrazolo[4,3-c]pyridin-5-yl]carbonyl}propyl)-8-(2-methylpyrimidin-5-yl)-9H-purin-6-amine;

(R)-9-ethyl-N-(1-{[3-(2-methylpropyl)-5,6-dihydro[1,2,4]triazolo[4,3-a]pyrazin-7(8H)-yl]carbonyl}propyl)-8-(2-methylpyrimidin-5-yl)-9H-purin-6-amine; and 9-ethyl-N-(1-{[1-methyl-3-(1-methylethyl)-1,4,6,7-tetrahydro-5H-pyrazolo[4,3-c]pyridin-5-yl]carbonyl}propyl)-8-(2-methylpyrimidin-5-yl)-9H-purin-6-amine.

14. The pharmaceutical composition comprising a compound of claim 1 or a pharmaceutically acceptable salt or stereoisomer thereof and a pharmaceutically acceptable carrier.

15. The pharmaceutical composition according to claim 9, further comprising one or more other therapeutic agents.

* * * * *